United States Patent [19]
Chee et al.

[11] Patent Number: 5,837,832
[45] Date of Patent: Nov. 17, 1998

[54] ARRAYS OF NUCLEIC ACID PROBES ON BIOLOGICAL CHIPS

[75] Inventors: Mark Chee, Palo Alto; Maureen T. Cronin, Los Altos; Stephen P. A. Fodor, Palo Alto; Xiaohua X. Huang; Earl A. Hubbell, both of Mt. View; Robert J. Lipshutz; Peter E. Lobban, both of Palo Alto; MacDonald S. Morris, San Jose; Edward L. Sheldon, Menlo Park, all of Calif.

[73] Assignee: Affymetrix, Inc., Santa Clara, Calif.

[21] Appl. No.: 441,887

[22] Filed: May 16, 1995

Related U.S. Application Data

[63] Continuation of Ser. No. 143,312, Oct. 26, 1993, abandoned, which is a continuation-in-part of Ser. No. 82,937, Jun. 25, 1993, abandoned.

[51] Int. Cl.[6] ............................................. C12Q 1/68
[52] U.S. Cl. ........................ 536/22.1; 435/6; 435/91.1; 436/501; 536/23.1; 536/24.1; 536/24.3; 536/24.31; 536/24.32; 536/24.33; 536/25.3; 422/68.1; 935/77; 935/78; 935/88
[58] Field of Search ............................. 435/6, 91.1, 810; 436/501; 536/22.1, 23.1, 24.1, 24.3–24.33, 25, 3; 935/77, 78, 88; 422/68.1

[56] References Cited

U.S. PATENT DOCUMENTS

| | | | |
|---|---|---|---|
| 4,656,127 | 4/1987 | Mundy | 435/6 |
| 4,683,195 | 7/1987 | Mallis et al. | 435/6 |
| 5,002,867 | 3/1991 | Macevicz | 435/6 |
| 5,143,854 | 9/1992 | Pirrung et al. | 436/518 |
| 5,202,231 | 4/1993 | Drmanac et al. | 435/6 |
| 5,273,632 | 12/1993 | Stockham et al. | 204/180.1 |
| 5,527,681 | 6/1996 | Homes | 435/6 |

FOREIGN PATENT DOCUMENTS

| | | | |
|---|---|---|---|
| WO 89/10977 | 11/1989 | WIPO | C12Q 1/68 |
| WO 89/11548 | 11/1989 | WIPO | C12Q 1/68 |
| WO 90/00626 | 1/1990 | WIPO | C12Q 1/68 |
| WO 90/03382 | 4/1990 | WIPO | C07H 21/00 |
| WO 92/10092 | 6/1992 | WIPO | A01N 1/02 |
| WO 92/10588 | 6/1992 | WIPO | C12Q 1/68 |
| WO 93/10588 | 6/1992 | WIPO | C12Q 1/68 |
| WO 93/17126 | 9/1993 | WIPO | C12Q 1/68 |

OTHER PUBLICATIONS

Maram et al. (1980) Methods in Enzymology, vol. 65, pp. 449–559.

Sambrook et al., Molecular Cloning, Cold Spring Harbor Laboratory Press, 1989, pp. 1145–1147

Stratagene 1988 Catalog, pp. 39.

Elder, J.K., "Analysis of DNA oligonucleotide hybridization data by maximum entropy," *Maximum Entropy and Bayesian Methods*, pp. 1–10, Paris (1992).

Lipshutz, Robert J., "Likelihood DNA sequencing by hybridization," *J. of Biomolecular Structure & Dynamics* 11:637–653 (1993).

Ying Luo et al., "Cellular protein modulates effects of human immunodeficiency virus type 1 rev," *J. of Virology* 68:3850–3856 (1994).

Querat et al., "Nucleotide sequence analysis of SA–OMVV, a Visna–related ovine lentivirus: phylogenetic history of lentiviruses," *Virology* 175:434–447 (1990).

Ratner et al., "Complete nucleotide sequence of the AIDS virus, HTLV–III," *Nature* 313:277–284 (1985).

(List continued on next page.)

*Primary Examiner*—Ardin H. Marschel
*Attorney, Agent, or Firm*—Townsend & Townsend & Crew

[57] ABSTRACT

DNA chips containing arrays of oligonucleotide probes can be used to determine whether a target nucleic acid has a nucleotide sequence identical to or different from a specific reference sequence. The array of probes comprises probes exactly complementary to the reference sequence, as well as probes that differ by one or more bases from the exactly complementary probes.

18 Claims, 40 Drawing Sheets

OTHER PUBLICATIONS

Wain–Hobson et al., "Nucleotide sequence of the AIDS virus, LAV," *Cell* 40:9–17 (1985).

Southern et al., "Analyzing and Comparing Nucleic Acid Sequences by Hybridization to Arrays of Oligonucleotides: Evaluation Using Experimental Models," *Genomics* (1992) 13:1008–1017.

Sanger et al., "DNA sequencing with chain–terminating inhibitors," *Proc. Natl. Acad. Sci. USA* (1977) 74:5463–5467.

M. Cronin et al., Hybridization to Arrays of Oligonucleotides, Poster Presentation: Nucleic Acids In Medical Applications Conference sponsored by AACC, Jan. 1993, published in conference syllabus, Cancun, Mexico.

M.S. Chee et al., Towards Sequencing Mitochondrial DNA Polymorphisms by Hybridization to a Custom Oligonucleotide Probe Array, American Society of Human Genetics 43rd Annual Meeting, Oct. 5–9, 1993, New Orleans, LA.

M.S. Chee et al., Genetic Analysis by Hybridization to Sequence–Specific DNA Arrays, Genome Sequencing and Analysis Conference V, Oct. 23–27, 1993, Hilton Head, SC.

P.E. Lobban et al., DNA Chips for Genetic Analysis, Genome Sequencing and Analysis Conference V, Oct. 23–27, 1993, Hilton Head, SC.

R. Lipshutz et al., Oligonucleotide Arrays for Hybridization Analysis, Genome Sequencing and Analysis Conference V, Oct. 23–27, 1993, Hilton Head, SC.

3' - CCGACTGCAGTCGTT
3' - CCGACTACAGTCGTT
3' - CCGACTCCAGTCGTT
3' - CCGACTGCAGTCGTT
3' - CCGACTTCAGTCGTT

WT ("G" Substitution)
Target 12-mer

"A" Substitution 12-mer Target

"T" Substitution Target 12-mer

"C" Substitution Target 12-mer

Fig. 27

DIMERS:

IN POLYNOMIAL NOTATION:
$(T + C + A + G)^2 = $ ALL DIMERS

TRIMERS:

ARRAYS OF NUCLEIC ACID PROBES ON BIOLOGICAL CHIPS

CROSS-REFERENCE TO RELATED APPLICATION

This is a Continuation of application Ser. No. 08/143,312, filed Oct. 26, 1993, now abandoned, which is a continuation in part of U.S. patent application Ser. No. 082,937, filed 25 Jun. 1993, now abandoned, incorporated herein by reference.

Research leading to the invention was funded in part by NIH grant No. 1R01HG00813-01 and DOE grant No. DE-FG03-92-ER81275, and the government may have certain rights to the invention.

BACKGROUND OF THE INVENTION

1. Field of the Invention

The present invention provides arrays of oligonucleotide probes immobilized in microfabricated patterns on silica chips for analyzing molecular interactions of biological interest. The invention therefore relates to diverse fields impacted by the nature of molecular interaction, including chemistry, biology, medicine, and medical diagnostics.

2. Description of Related Art

Oligonucleotide probes have long been used to detect complementary nucleic acid sequences in a nucleic acid of interest (the "target" nucleic acid). In some assay formats, the oligonucleotide probe is tethered, i.e., by covalent attachment, to a solid support, and arrays of oligonucleotide probes immobilized on solid supports have been used to detect specific nucleic acid sequences in a target nucleic acid. See, e.g., PCT patent publication Nos. WO 89/10977 and 89/11548. Others have proposed the use of large numbers of oligonucleotide probes to provide the complete nucleic acid sequence of a target nucleic but failed to provide an enabling method for using arrays of immobilized probes for this purpose. See U.S. Pat. Nos. 5,202,231 and 5,002,867 and PCT patent publication No. WO 93/17126.

The development of VLSIPS™ technology has provided methods for making very large arrays of oligonucleotide probes in very small arrays. See U.S. Pat. No. 5,143,854 and PCT patent publication Nos. WO 90/15070 and 92/10092, each of which is incorporated herein by reference. U.S. patent application Ser. No. 082,937, filed Jun. 25, 1993, describes methods for making arrays of oligonucleotide probes that can be used to provide the complete sequence of a target nucleic acid and to detect the presence of a nucleic acid containing a specific nucleotide sequence.

Microfabricated arrays of large numbers of oligonucleotide probes, called "DNA chips" offer great promise for a wide variety of applications. New methods and reagents are required to realize this promise, and the present invention helps meet that need.

SUMMARY OF THE INVENTION

The present invention provides methods for making high-density arrays of oligonucleotide probes on silica chips and for using those probe arrays to detect specific nucleic acid sequences contained in a target nucleic acid in a sample. The invention also provides arrays of oligonucleotide probes on DNA chips, in which the probes have specific sequences and locations in the array to facilitate identification of a specific target nucleic acid. In another aspect, the invention provides methods for detecting whether one or more specific sequences of a target nucleic acid in a sample varies from a previously characterized sequence or reference sequence. The methods of the invention can be used to detect variations between a target and reference sequence, including single or multiple base substitutions, and deletions and insertions of bases, as well as detecting the presence, location, and sequence of other more complex variations between a target and reference sequence in a nucleic acid.

The present invention provides arrays of oligonucleotide probes immobilized on a solid support. The arrays are preferably synthesized directly on the support using VLSIPS™ technology, but other synthesis methods and immobilization of pre-synthesized oligonucleotide probes can be used to make the oligonucleotide probe arrays, called "DNA chips", of the invention. In general, these arrays comprise a set of oligonucleotide probes such that, for each base in a specific reference sequence, the set includes a probe (called the "wild-type" or "WT" probe) that is exactly complementary to a section of the reference sequence including the base of interest and four additional probes (called "substitution probes"), which are identical to the WT probe except that the base of interest has been replaced by one of a predetermined set (typically 4) of nucleotides. In the preferred embodiment, one of the four substitution probes is identical to the wild type probe; the other three are complementary to targets that have a single-base substitution at this position.

In another aspect, the invention relates to the arrangement of individual probes in the array. In one embodiment, the probes are arranged on the chip so that probes for a given position in the sequence are adjacent, and probes for adjacent positions in the reference sequence are also adjacent to one another on the chip. One method arranges the probes for a single base in a short column (alternately row) and arranges the columns in the order of the base position to form horizontal (alternately vertical) stripes. The wild-type and each of the substitution probes have specified positions within the column so that all the probes corresponding to an A substitution, for example, are in a single row. The stripes may be separated on the chip by a blank row or column.

The DNA chips of the invention can be made in a wide number of variations. For some applications, leaving out the wild-type row, leaving out unimportant bases, pooling bases, including insertion and deletion probes, varying the length of the probes within a set to make the probes have the same or similar Tm relative to the target or to avoid secondary structure, varying the mutation position, using multiple probes for a single mutation, providing replicate probes or arrays, placing blank "streets" (no probe) between rows, columns, or individual probes, and using control probes may be appropriate.

The present invention also provides DNA chips for detecting mutations associated with cystic fibrosis, including mutations in exons 4, 7, 9, 10, 11, 20, and 21 of the CFTR gene. The invention also provides DNA chips for detecting mutations in the p53 gene, a gene in which mutations are known to be associated with a wide variety of cancers. Other DNA chips of the invention provide probe arrays for detecting specific sequences of mitochondrial DNA, useful for identification and forensic purposes. The invention also provides DNA chips for detecting specific sequences of nucleotides or mutations associated with the acquisition of a drug resistant phenotype in an infectious organism, such as rifampicin or other drug resistant TB strains and HIV, in which mutations in an RNA polymerase gene are known to give rise to drug resistance.

In the figure, the target is a DNA molecule, the probes are single-stranded nucleic acids 16 nucleotides in length, and only a portion of the probes defined by the method is shown.

Figure 2:
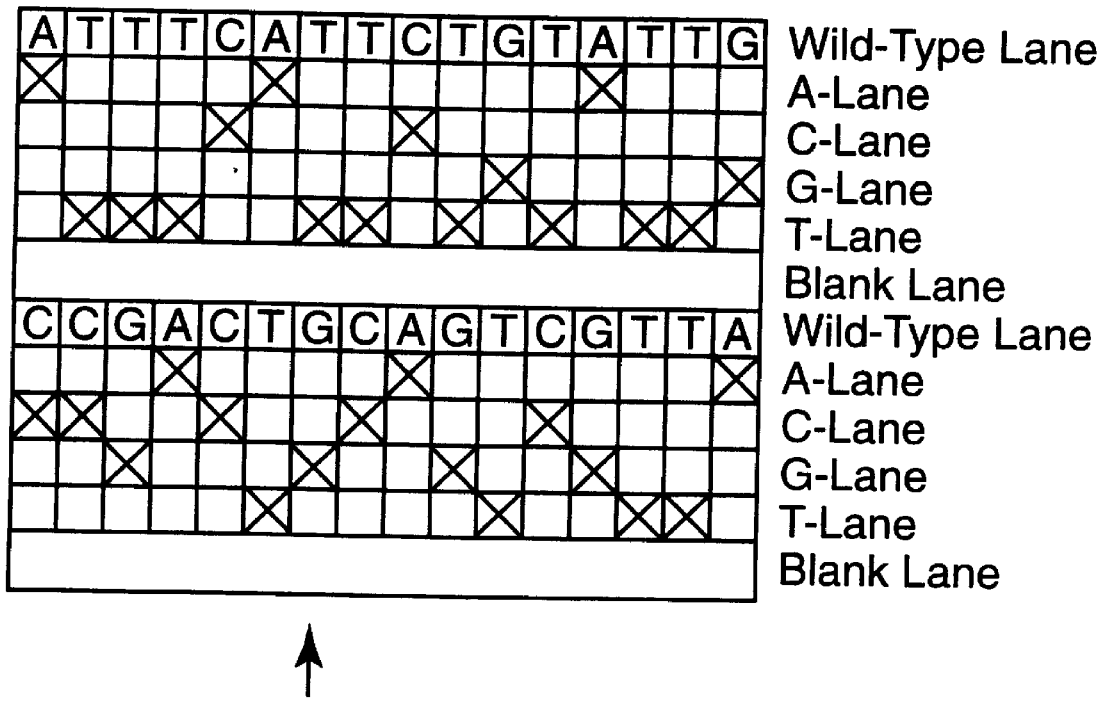

FIG. 2 shows an illustrative tiled array of the invention with probes for the detection of point mutations. The base at the position of substitution in each of the wild-type probes is shown in the wild-type lane, and the shading shows the location of the substitution probe having the wild-type sequence. The SEQ ID. NOS. corresponding to the two peptide sequences shown in the top portion of FIG. 2 are 311 and 312, respectively. The SEQ ID. NOS. corresponding to the five peptide sequences listed at the bottom of FIG. 2 are 313, 314, 315, 313, and 316, respectively.

Figure 3:
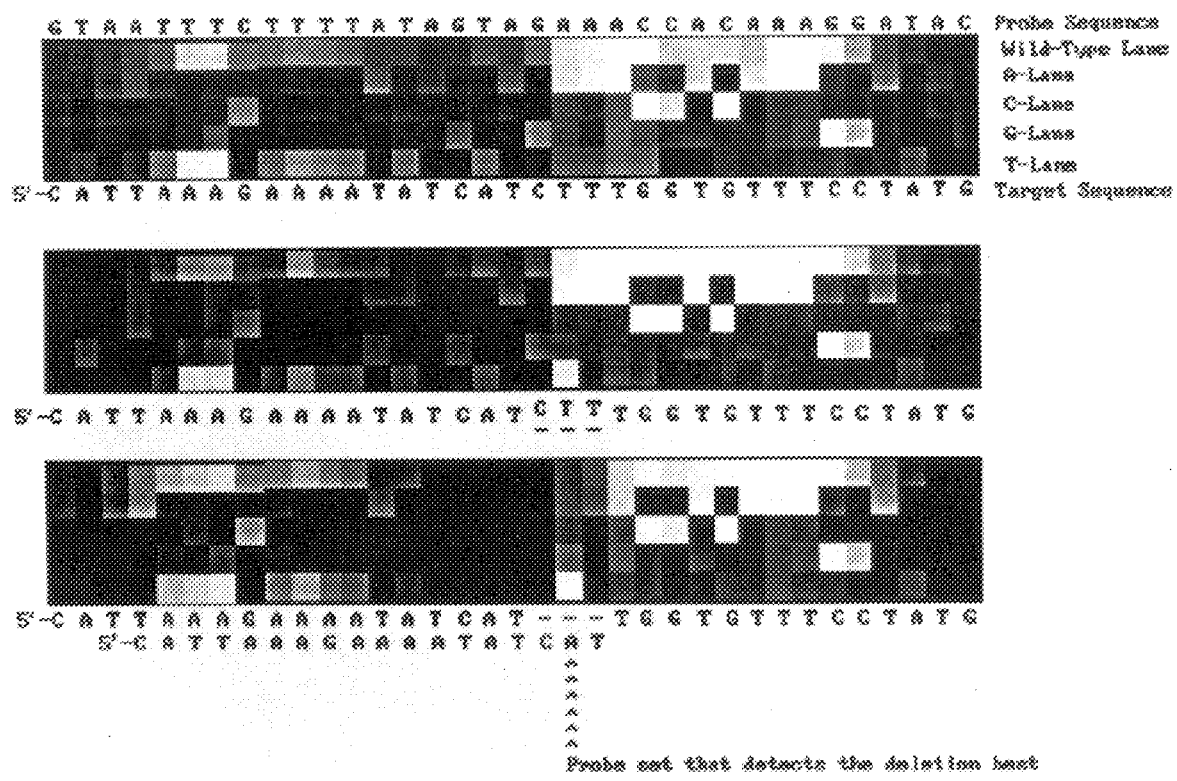

FIG. 3, in panels A, B, and C, shows an image made from the region of a DNA chip containing CFTR exon 10 probes; in panel A, the chip was hybridized to a wild-type target; in panel C, the chip was hybridized to a mutant ΔF508 target; and in panel B, the chip was hybridized to a mixture of the wild-type and mutant targets. The SEQ ID. NOS. corresponding to the four peptide sequences shown in FIG. 3 are 317–320, respectively.

Figure 4A:
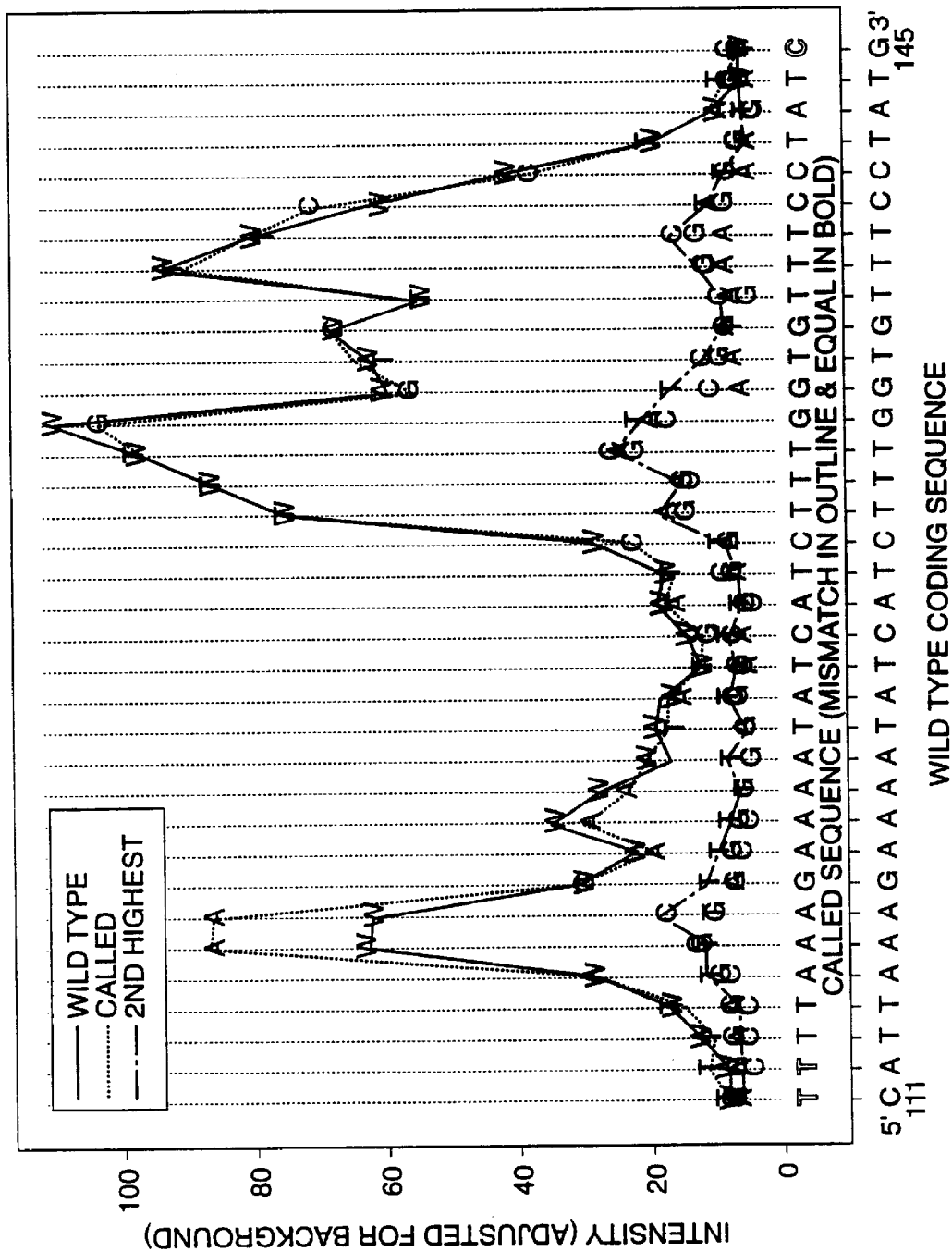
Figure 4B:
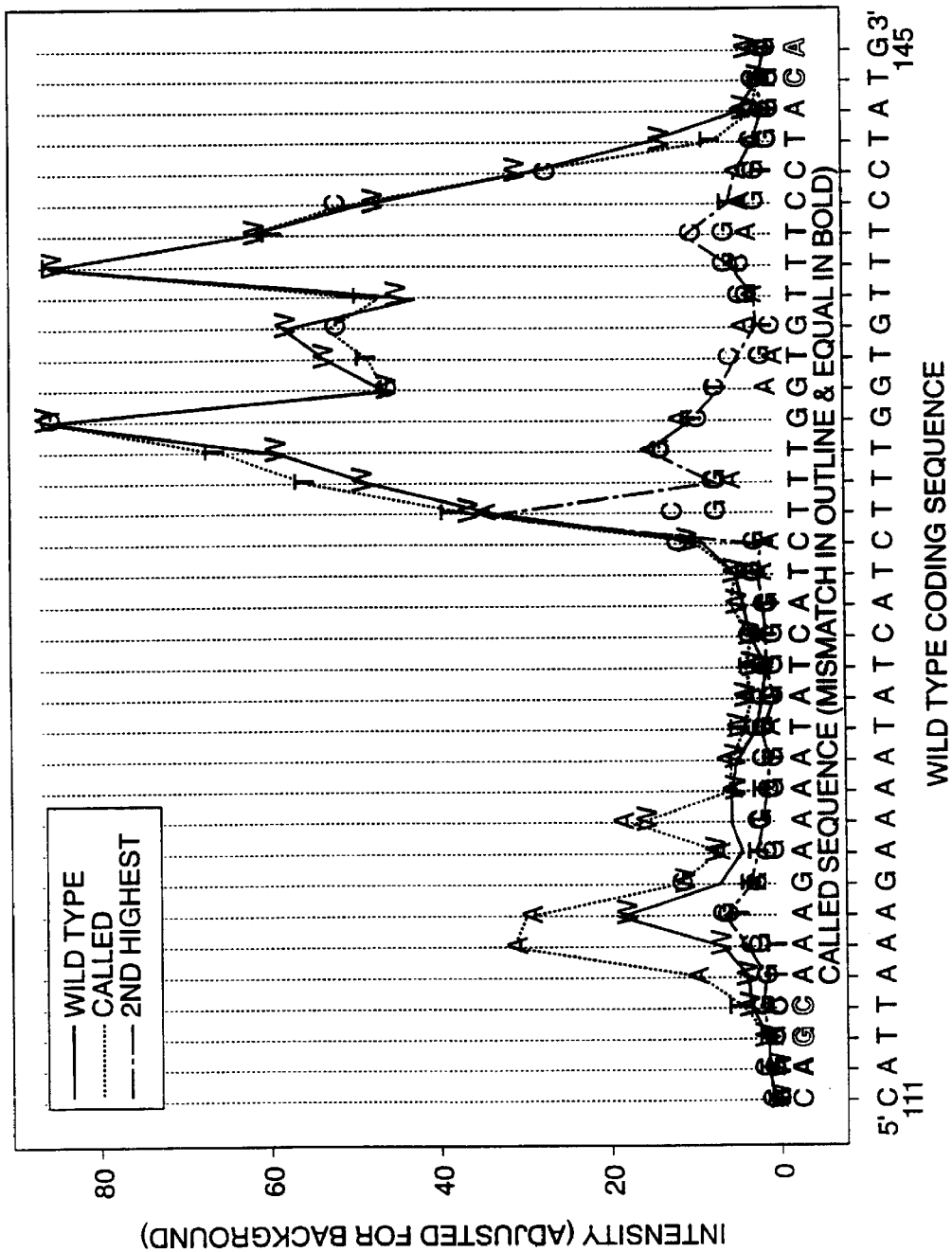
Figure 4C:
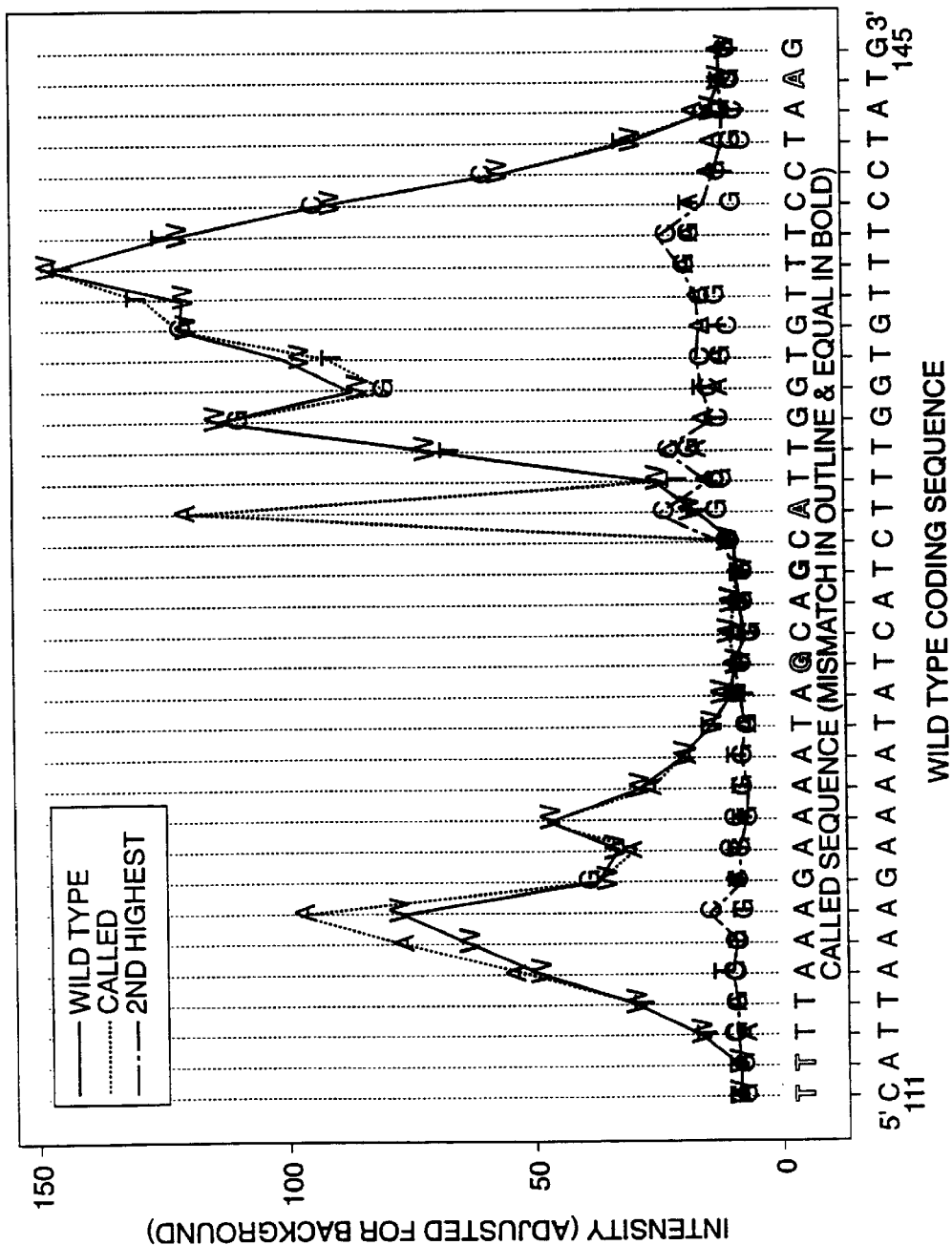

FIG. 4, in sheets 1–3, corresponding to panels A, B, and C of FIG. 3, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest"). The SEQ ID. NOS. corresponding to the two peptide sequences shown in sheet 1 of FIG. 4 are 321 and 318, respectively; the SEQ ID. NOS. corresponding to the two peptide sequences shown in sheet 2 of FIG. 4 are 322 and 318, respectively; and the SEQ ID. NOS. corresponding to the two peptide sequences shown in sheet 3 of FIG. 4 are 323 and 318, respectively.

Figure 5:
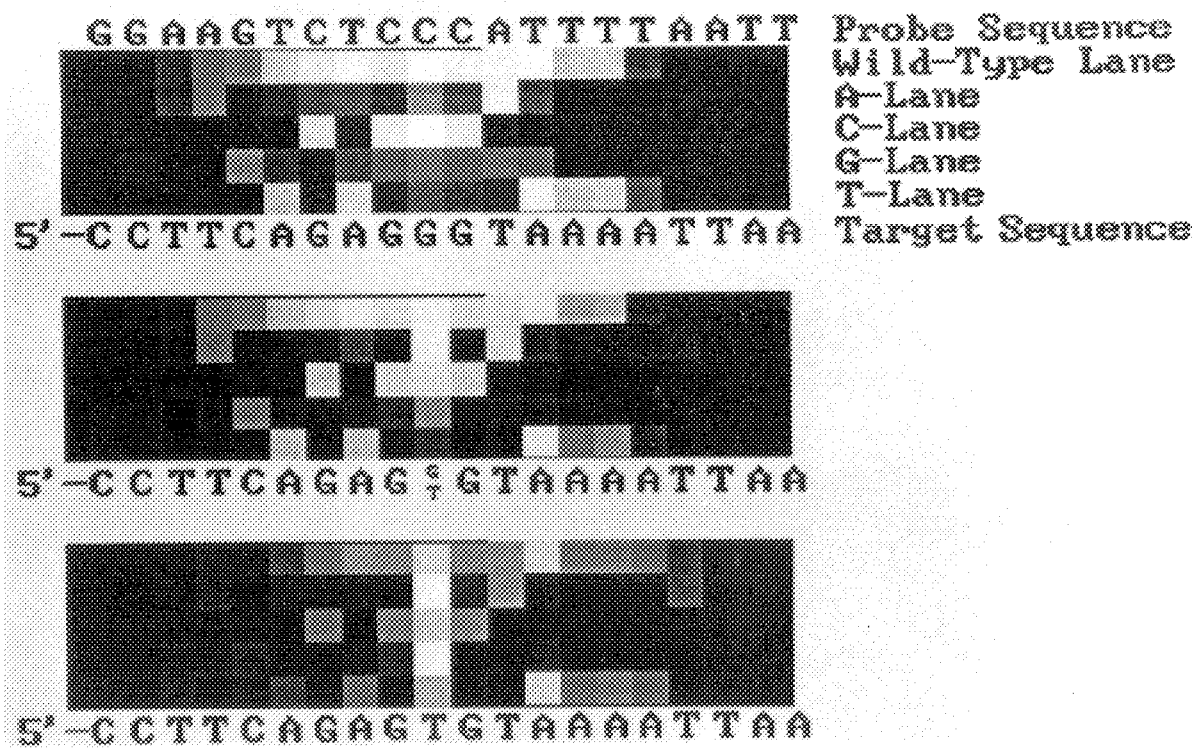

FIG. 5, in panels A, B, and C, shows an image made from a region of a DNA chip containing CFTR exon 10 probes; in panel A, the chip was hybridized to the wt480 target; in panel C, the chip was hybridized to the mu480 target; and in panel B, the chip was hybridized to a mixture of the wild-type and mutant targets. The SEQ ID. NOS. corresponding to the peptide sequences shown in FIG. 5 are 324–327, respectively.

Figure 6A:
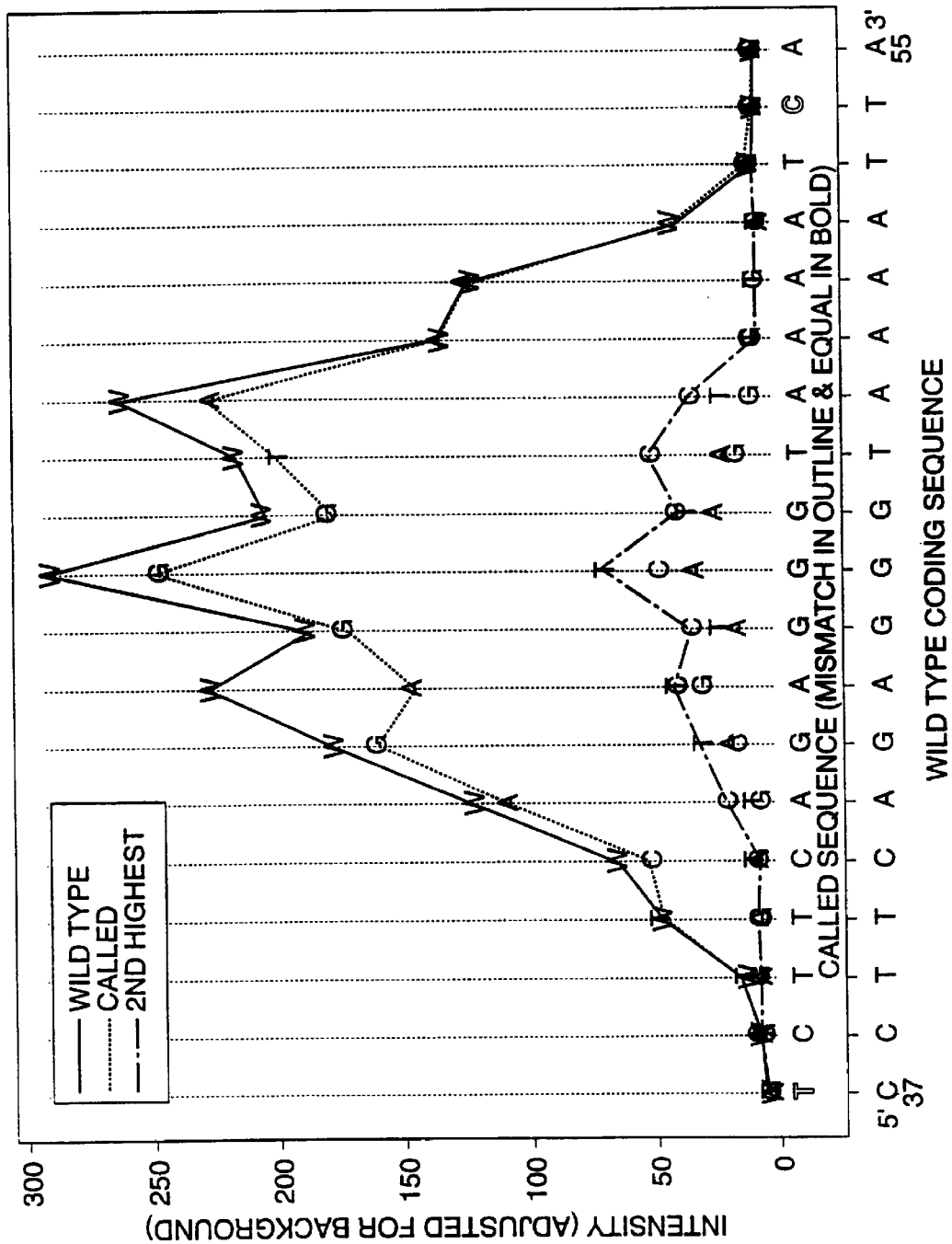
Figure 6B:
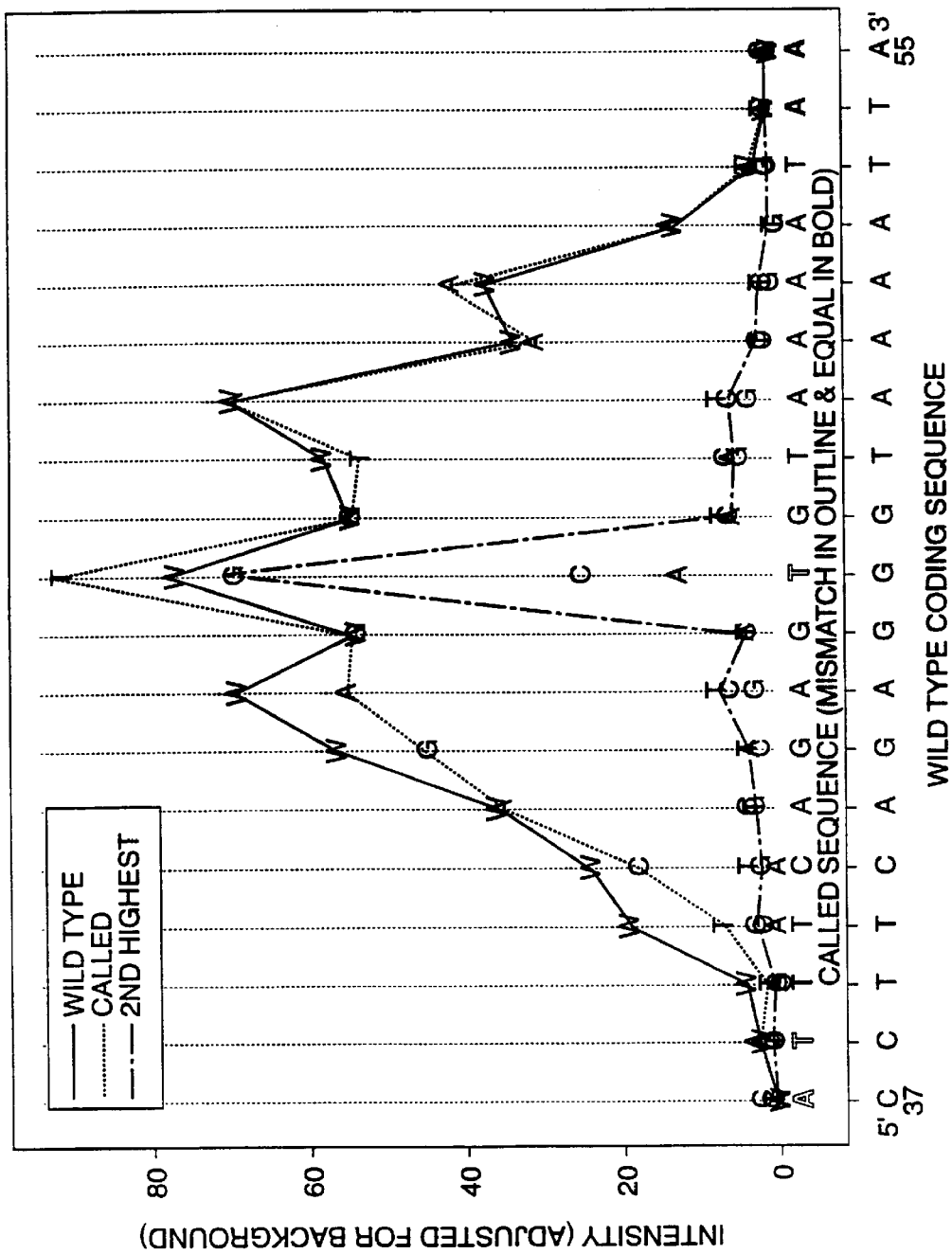
Figure 6C:
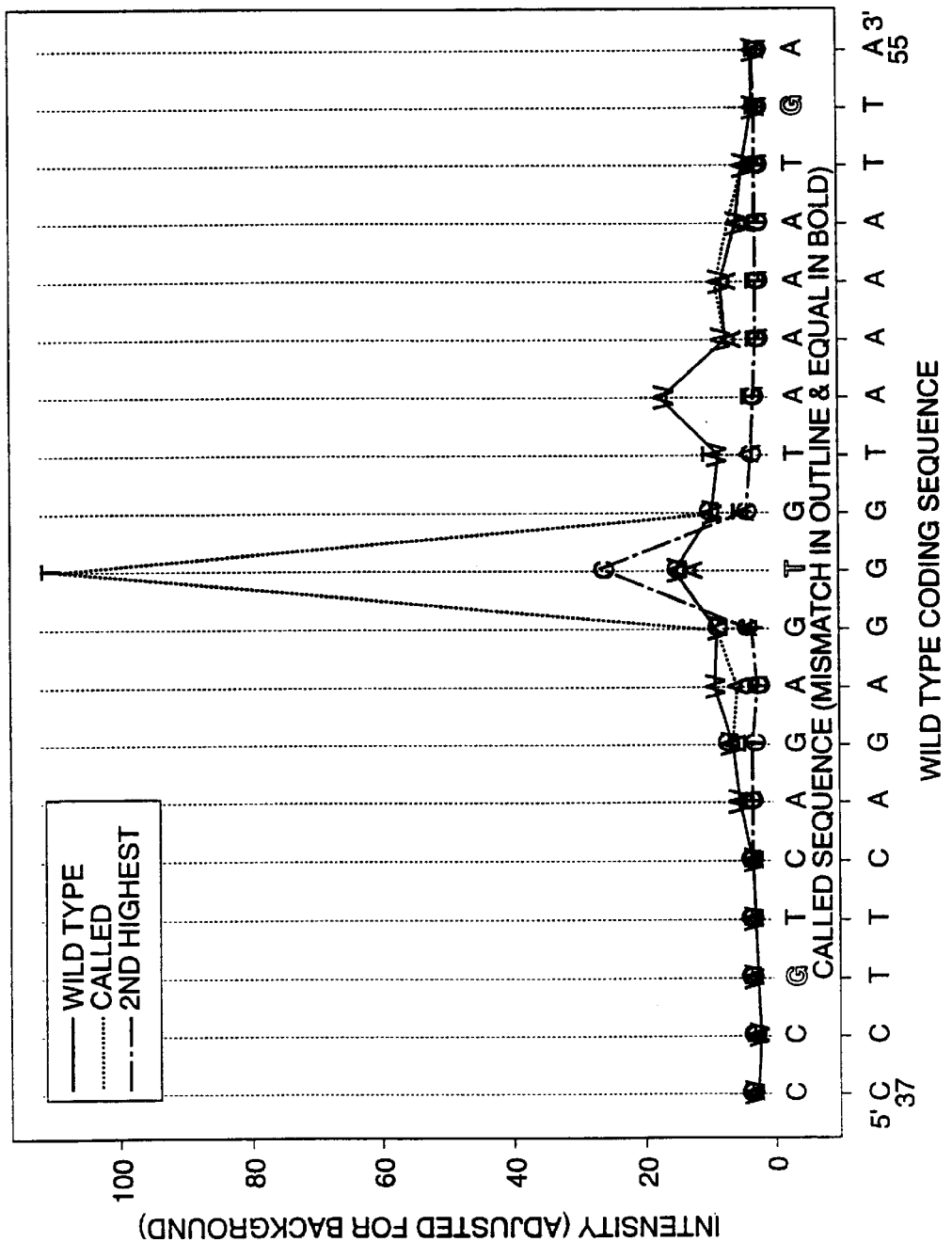

FIG. 6, in sheets 1–3, corresponding to panels A, B, and C of FIG. 5, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest"). The SEQ ID. NOS. corresponding to the two peptide sequences shown in sheet 1 of FIG. 6 are 328 and 329, respectively; the SEQ ID. NOS. corresponding to the two peptide sequences shown in sheet 2 of FIG. 6 are 330 and 329, respectively; and the SEQ ID. NOS. corresponding to the two peptide sequences shown in sheet 3 of FIG. 6 are 331 and 329, respectively.

Figure 7:
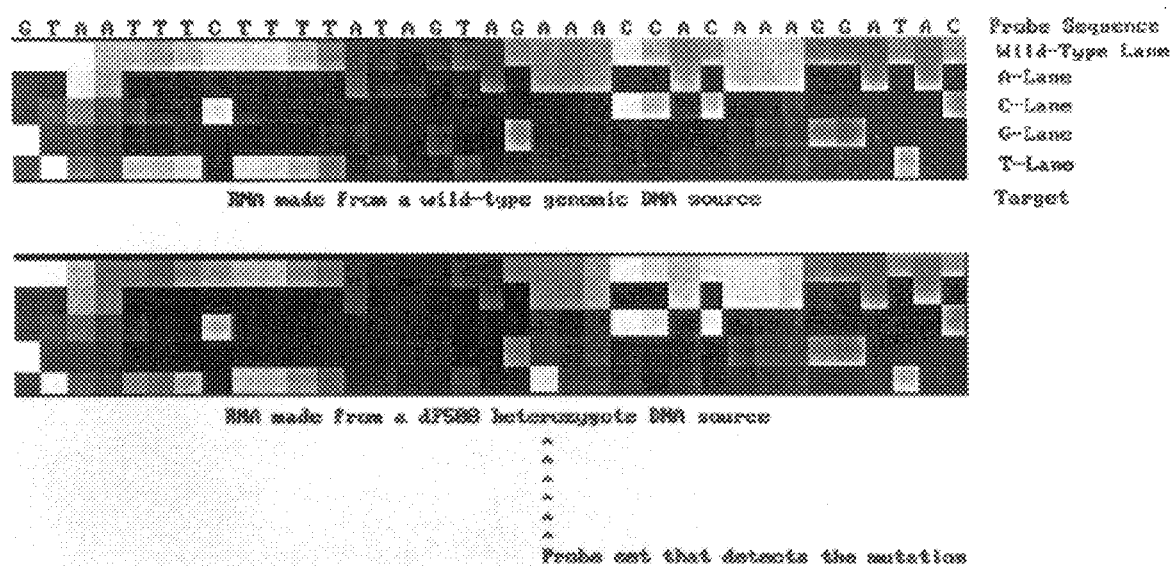

FIG. 7, in panels A and B, shows an image made from a region of a DNA chip containing CFTR exon 10 probes; in panel A, the chip was hybridized to nucleic acid derived from the genomic DNA of an individual with wild-type ΔF508 sequences; in panel B, the target nucleic acid originated from a heterozygous (with respect to the ΔF508 mutation) individual.

Figure 8A:
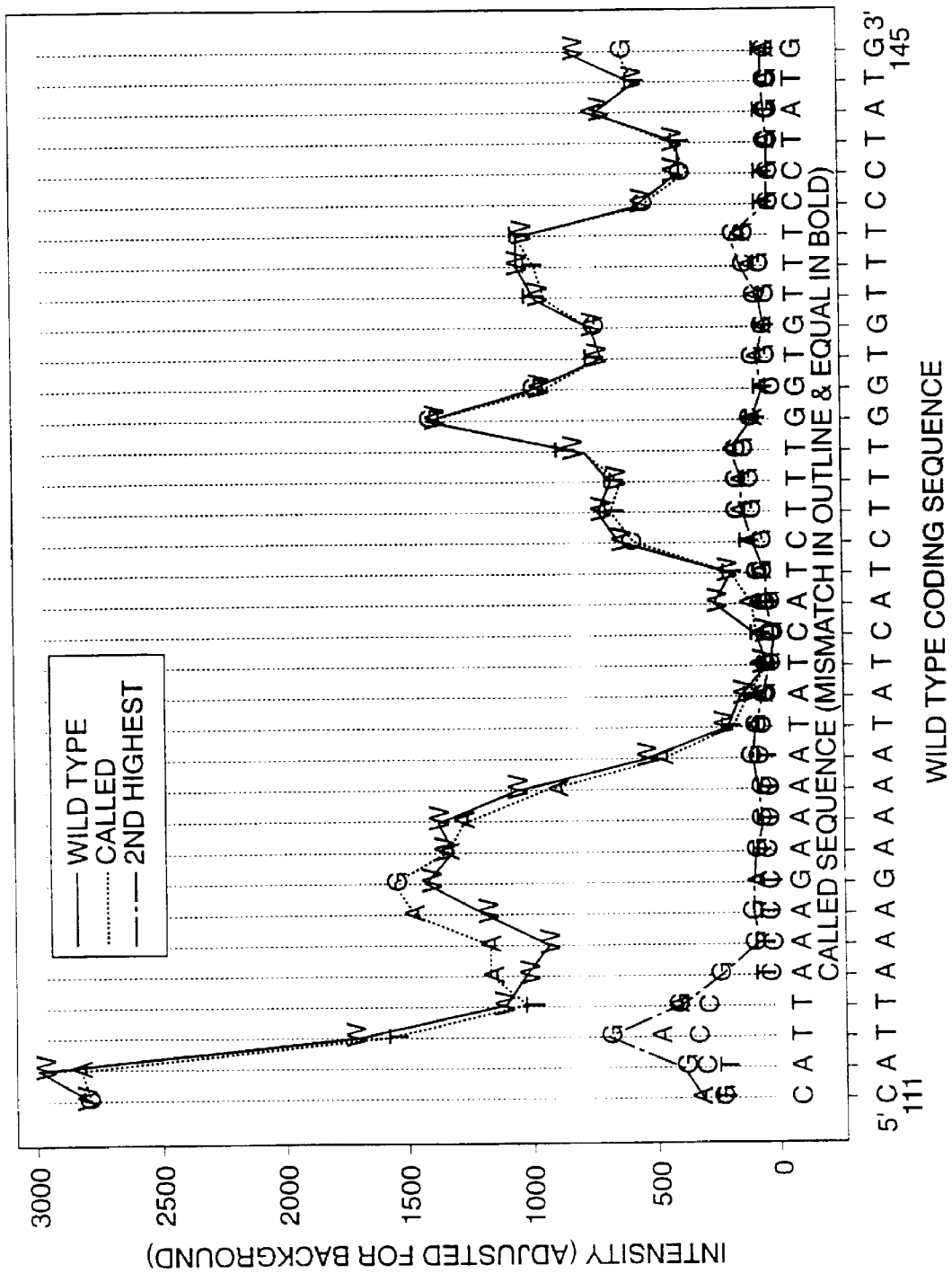
Figure 8B:
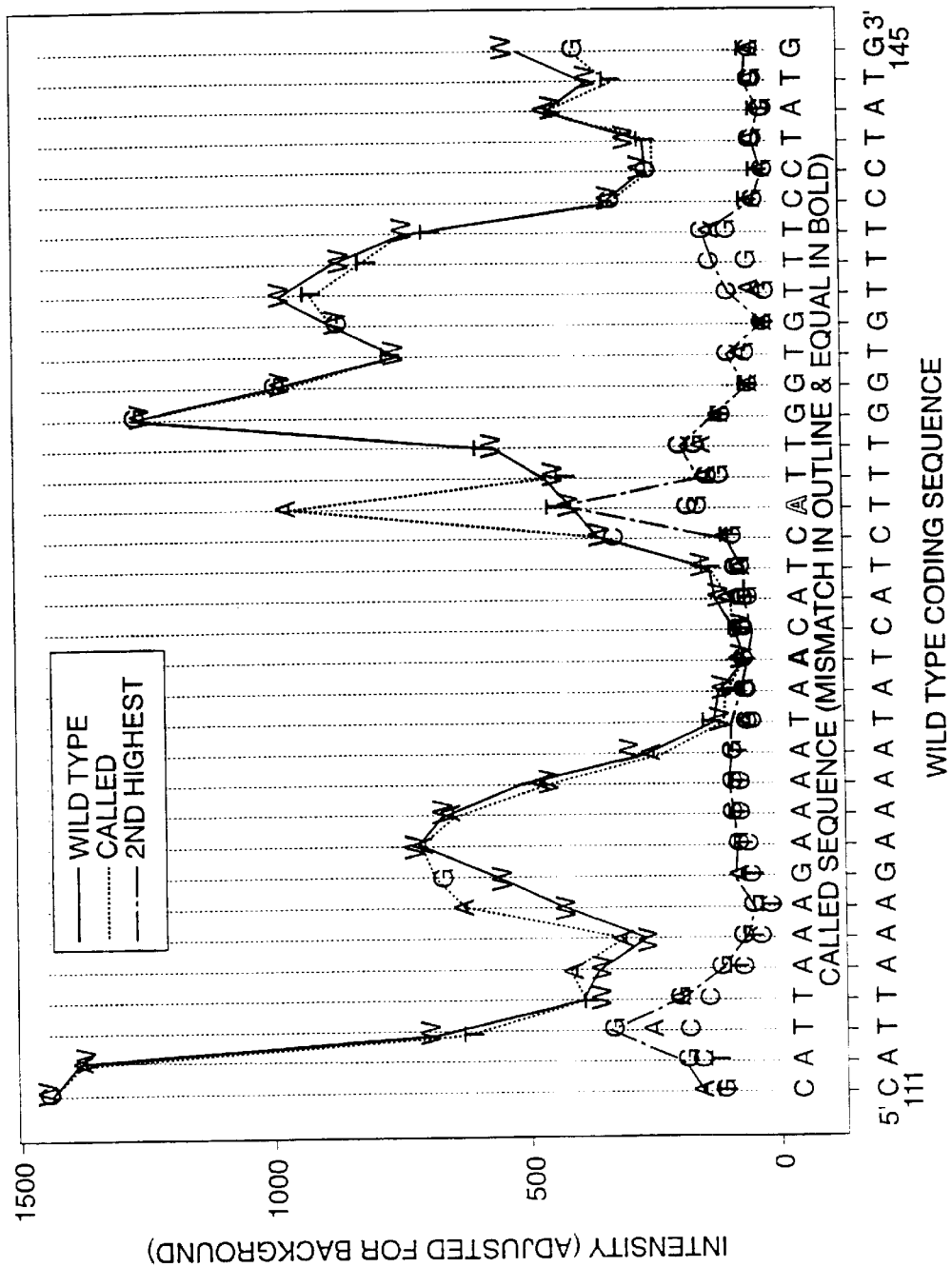

FIG. 8, in sheets 1 and 2, corresponding to panels A and B of FIG. 7, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest"). The SEQ ID NOS. corresponding to the two peptide sequences shown in sheet 2 of FIG. 8 are 332 and 318, respectively.

Figure 9:
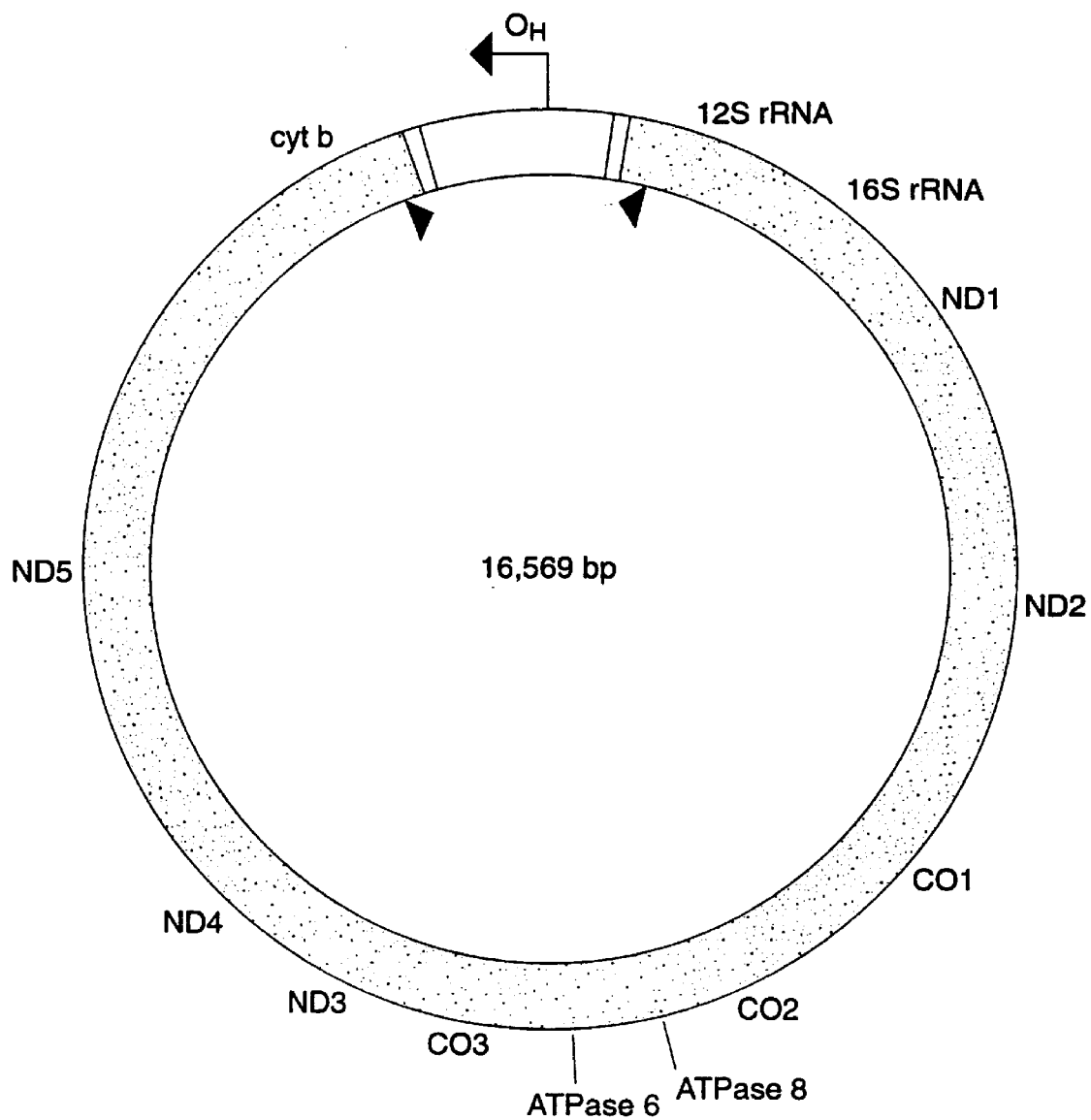

FIG. 9 shows the human mitochondrial genome; "$O_H$" is the H strand origin of replication, and arrows indicate the cloned unshaded sequence.

Figure 10:
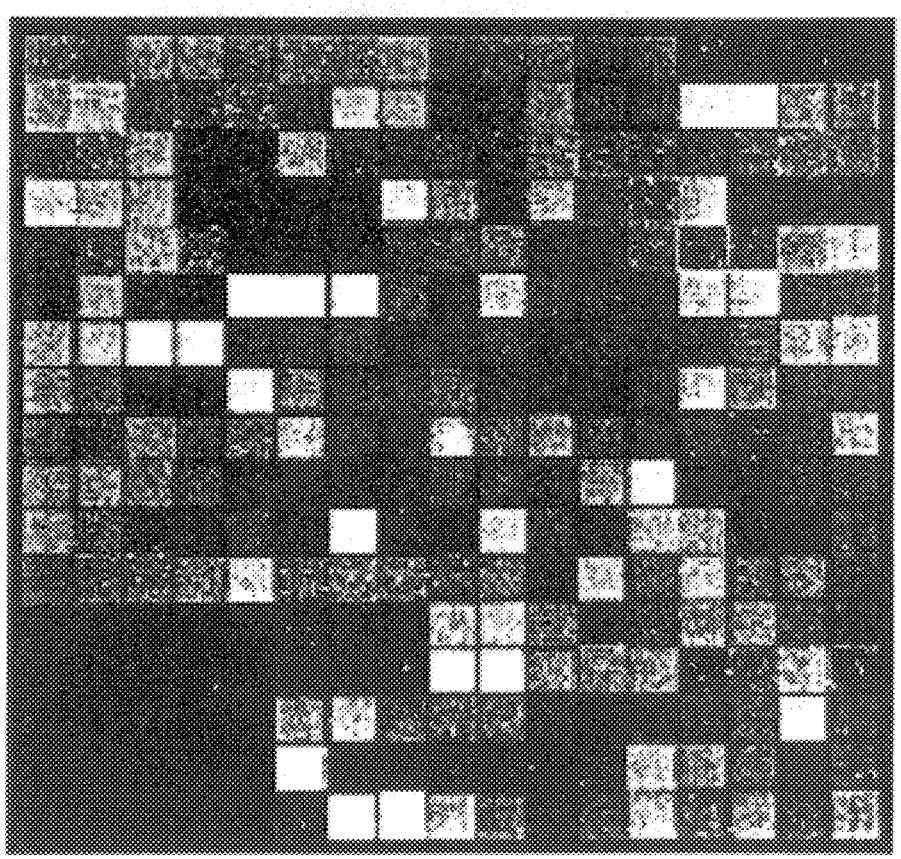

FIG. 10 shows the image observed from application of a sample of mitochondrial DNA derived nucleic acid (from the mt4 sample) on a DNA chip.

Figure 11:
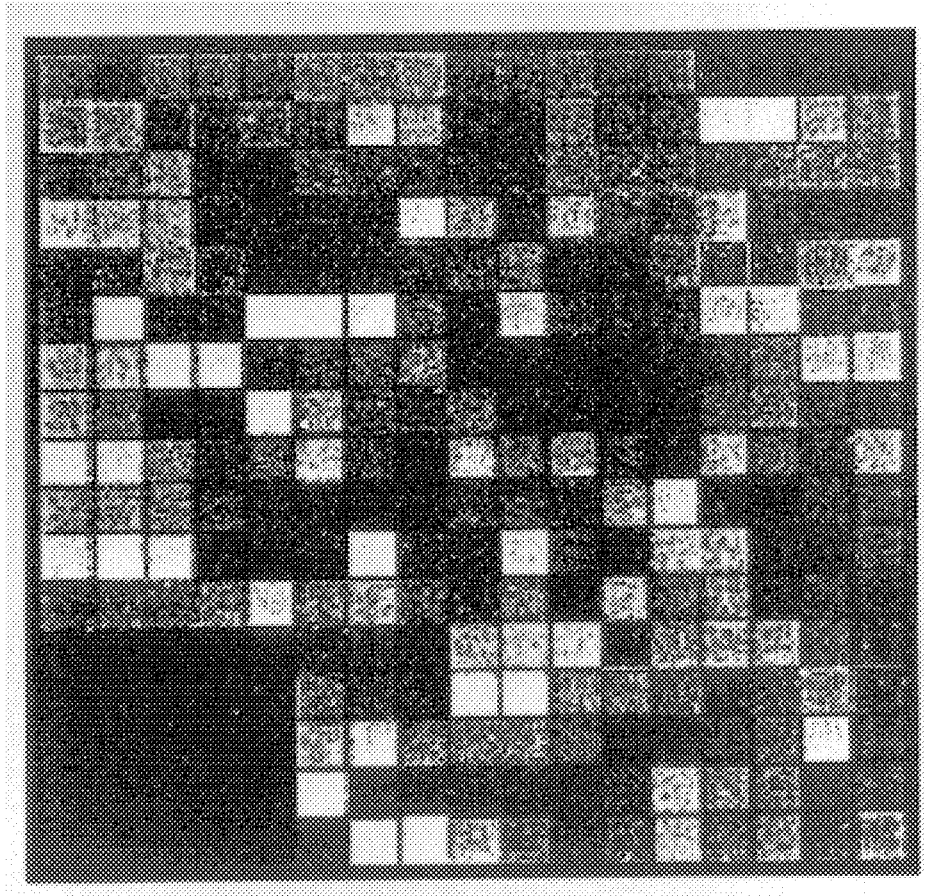

FIG. 11 is similar to FIG. 10 but shows the image observed from the mt5 sample.

Figure 12:
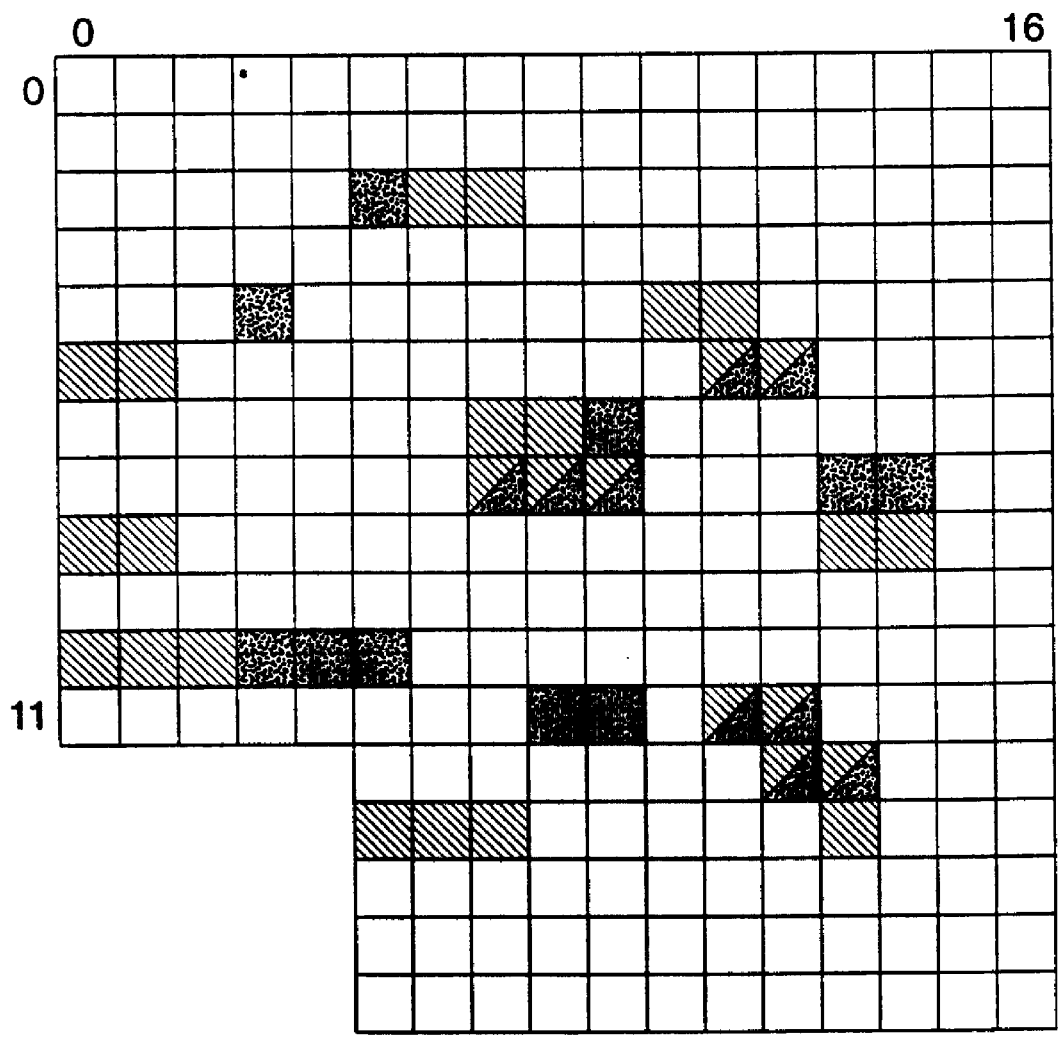

FIG. 12 shows the predicted difference image between the mt4 and mt5 samples on the DNA chip based on mismatches between the two samples and the reference sequence.

Figure 13:
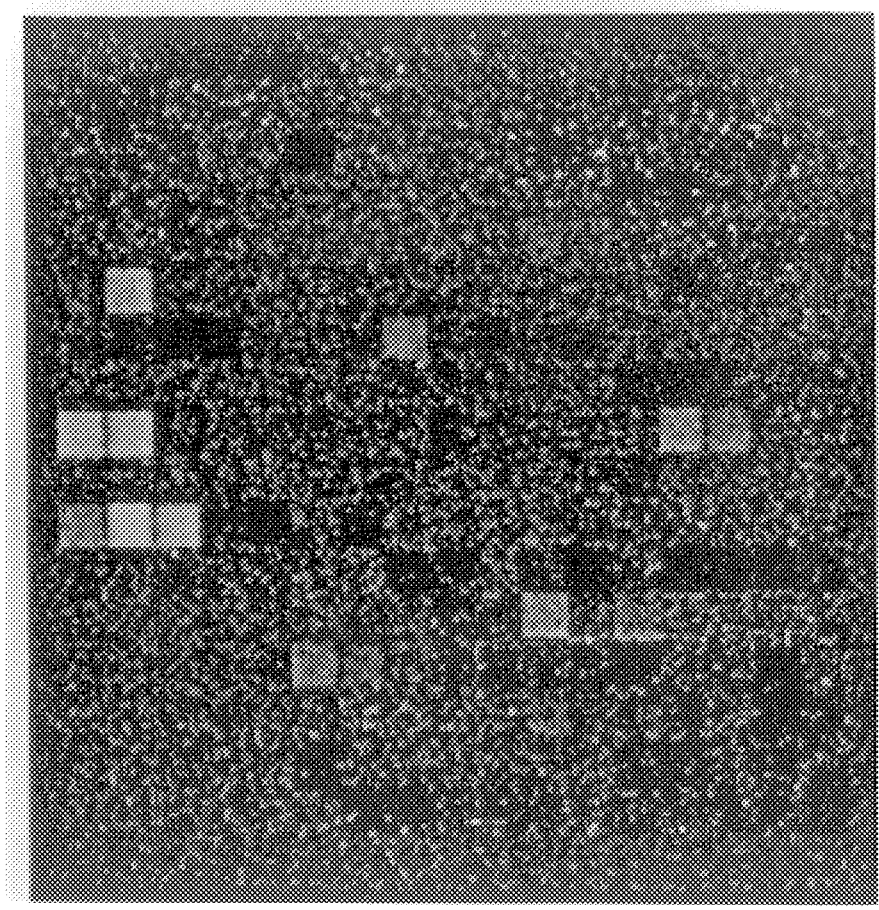

FIG. 13 shows the actual difference image observed for the mt4 and mt5 samples.

Figure 14A:
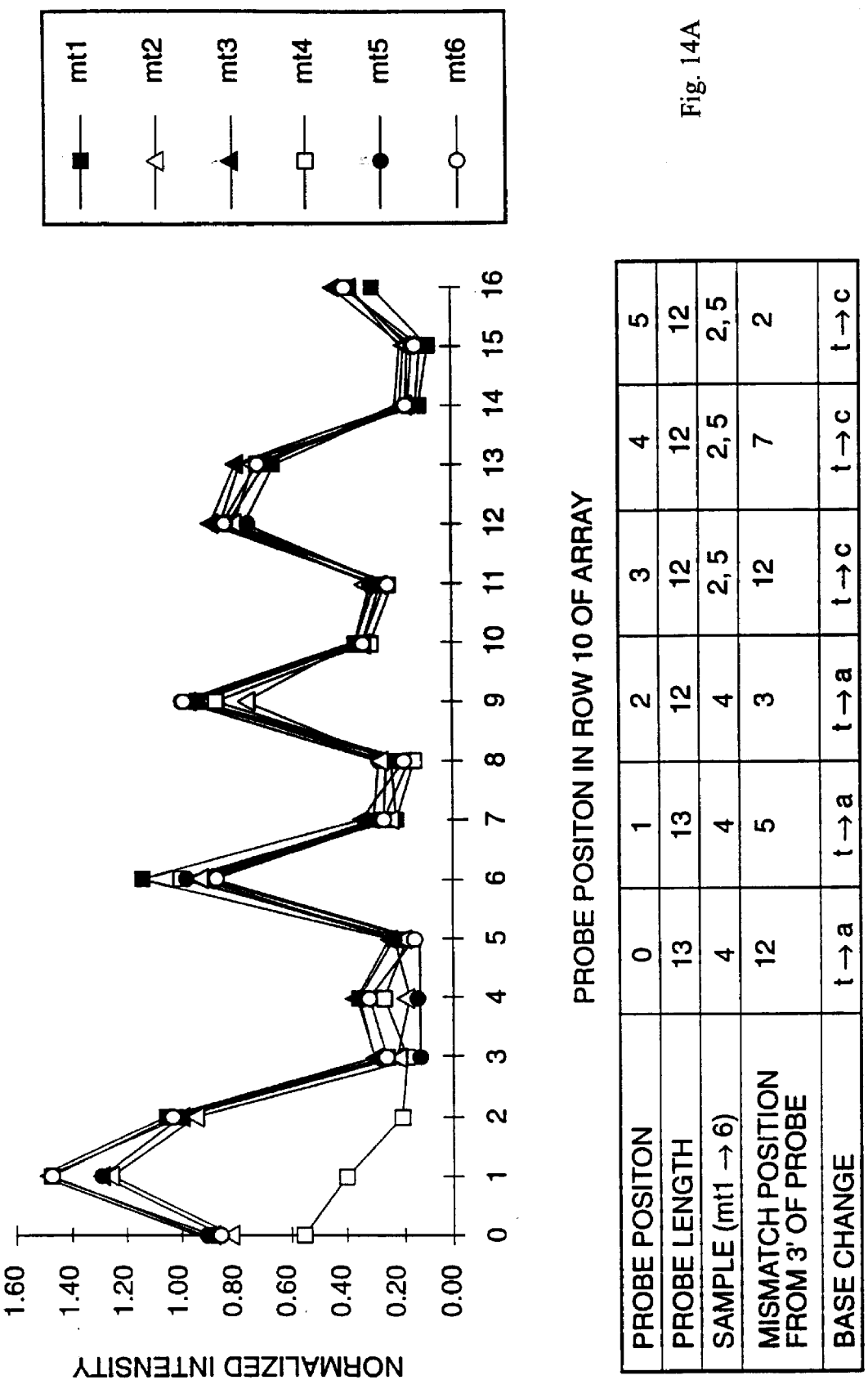
Figure 14B:
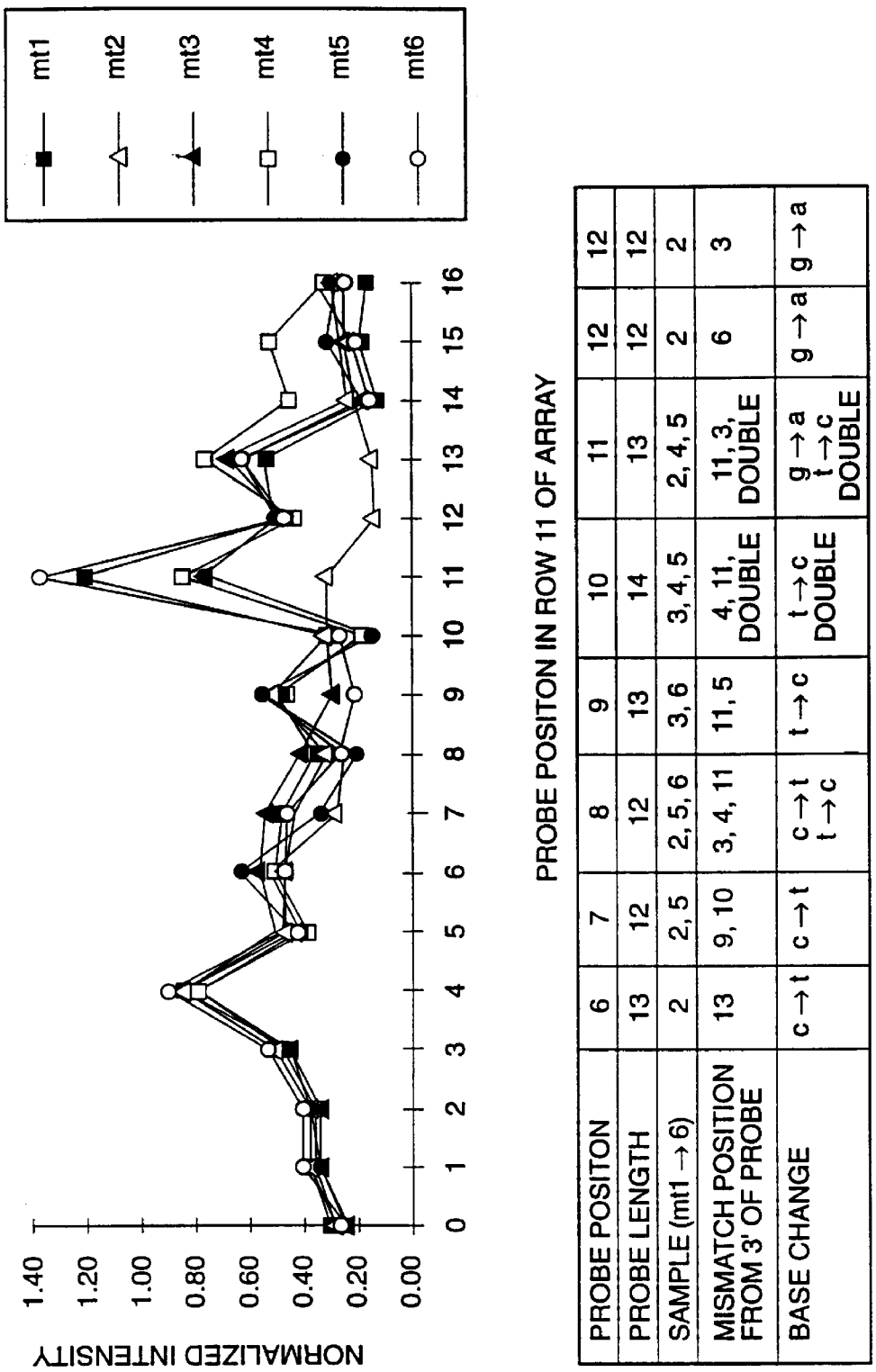

FIG. 14, in sheets 1 and 2, shows a plot of normalized intensities across rows 10 and 11 of the array and a tabulation of the mutations detected.

Figure 15:
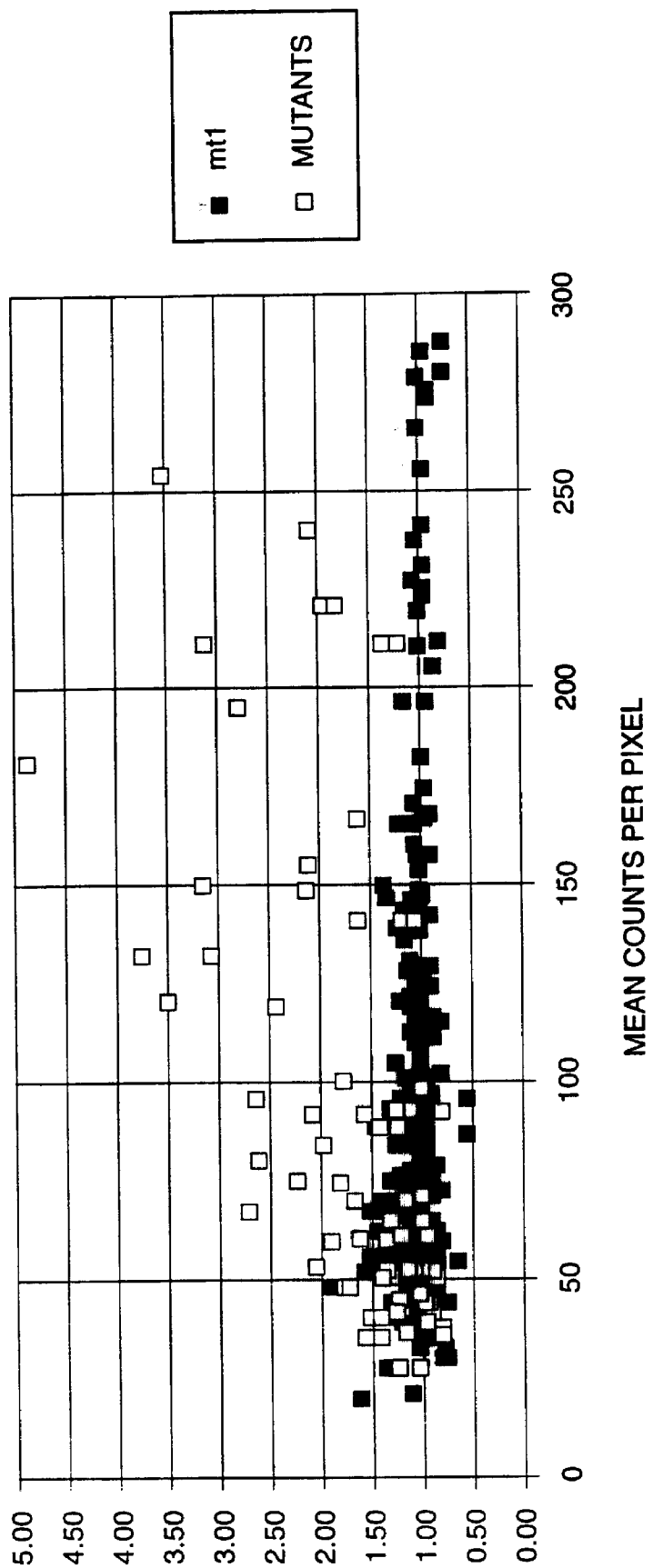

FIG. 15 shows the discrimination between wild-type and mutant hybrids obtained with the chip. A median of the six normalized hybridization scores for each probe was taken; the graph plots the ratio of the median score to the normalized hybridization score versus mean counts. A ratio of 1.6 and mean counts above 50 yield no false positives.

Figure 16:
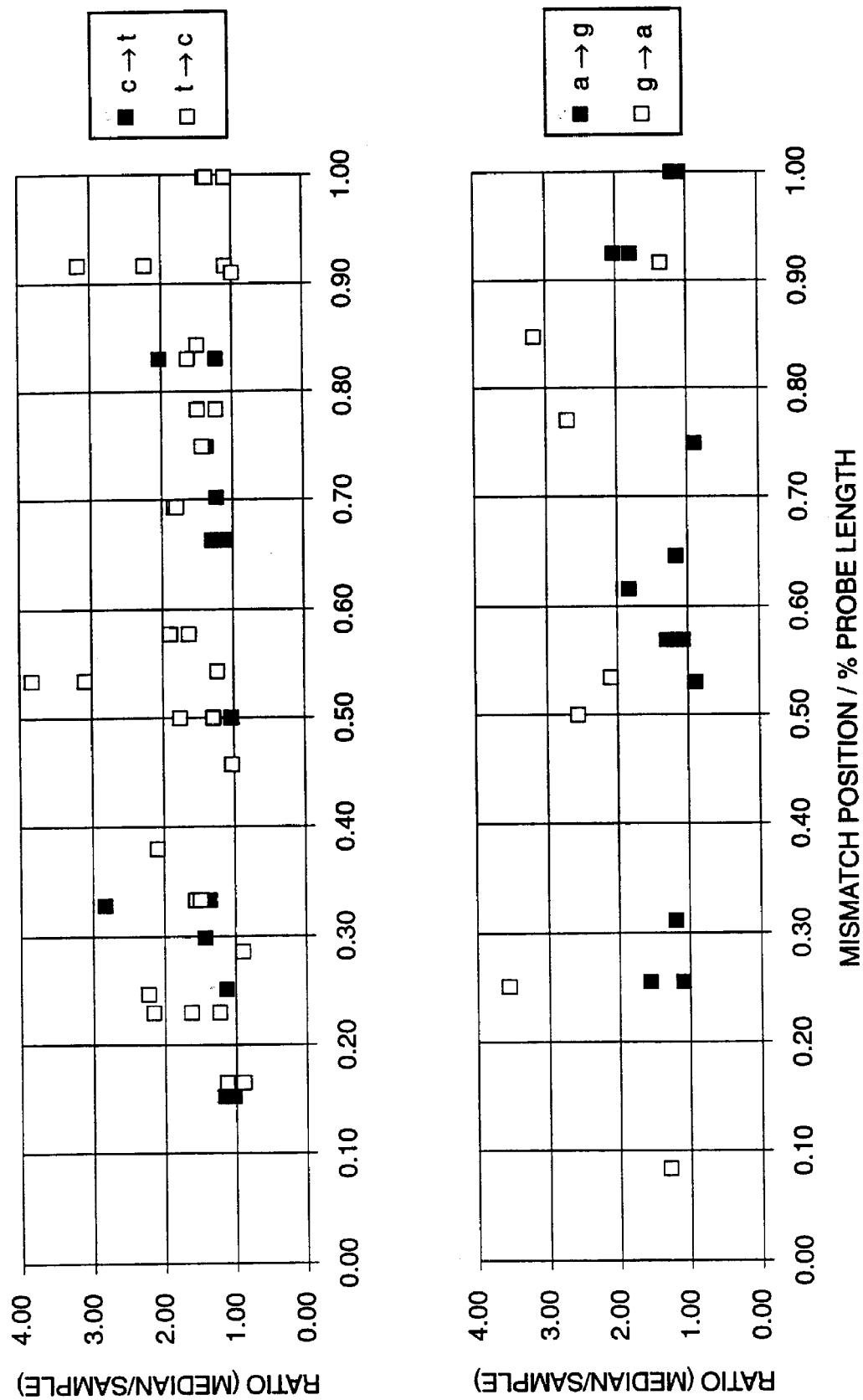

FIG. 16 illustrates how the identity of the base mismatch may influence the ability to discriminate mutant and wild-type sequences more than the position of the mismatch within an oligonucleotide probe. The mismatch position is expressed as % of probe length from the 3'-end. The base change is indicated on the graph.

FIG. 17 provides a 5' to 3' sequence listing of one target corresponding to the probes on the chip. X is a control probe. Positions that differ in the target (i.e., are mismatched with the probe at the designated site) are in bold. The SEQ ID. NO. corresponding to the peptide sequence shown in FIG. 17 is 333.

Figure 18:
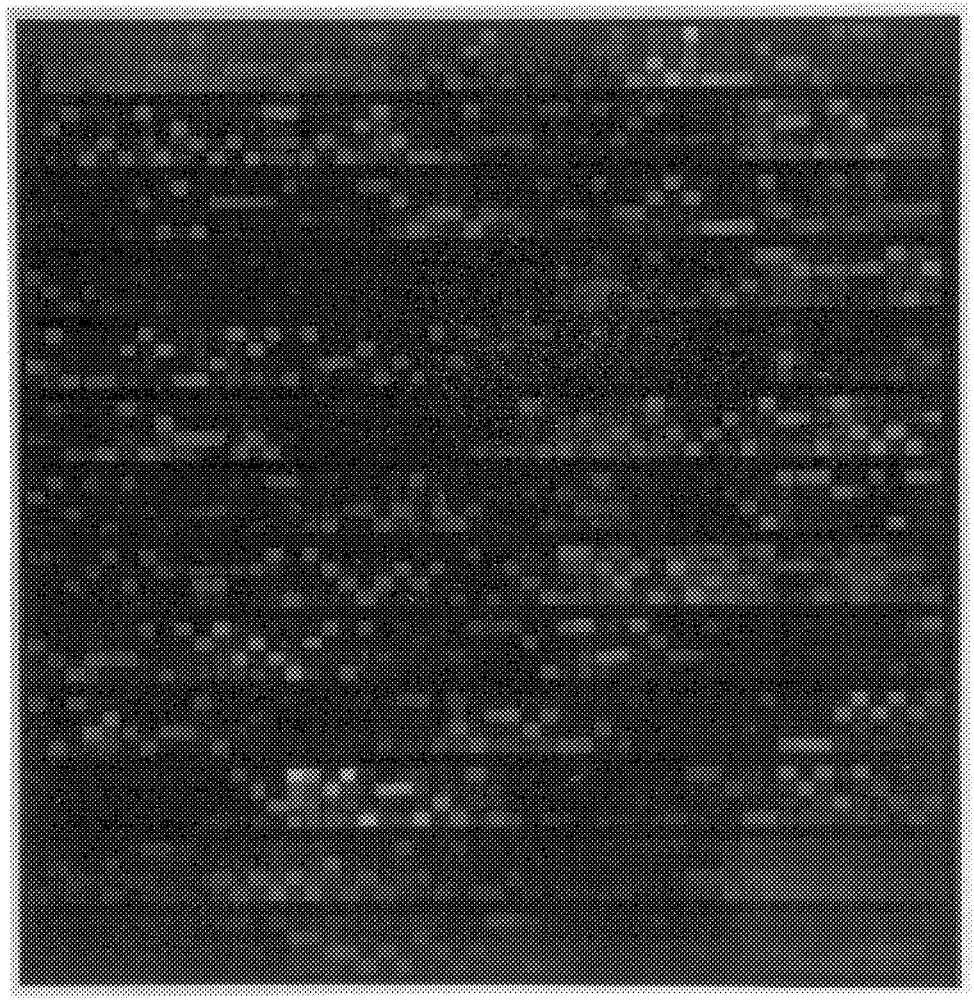

FIG. 18 shows the fluorescence image produced by scanning the chip described in FIG. 17 when hybridized to a sample.

Figure 19:
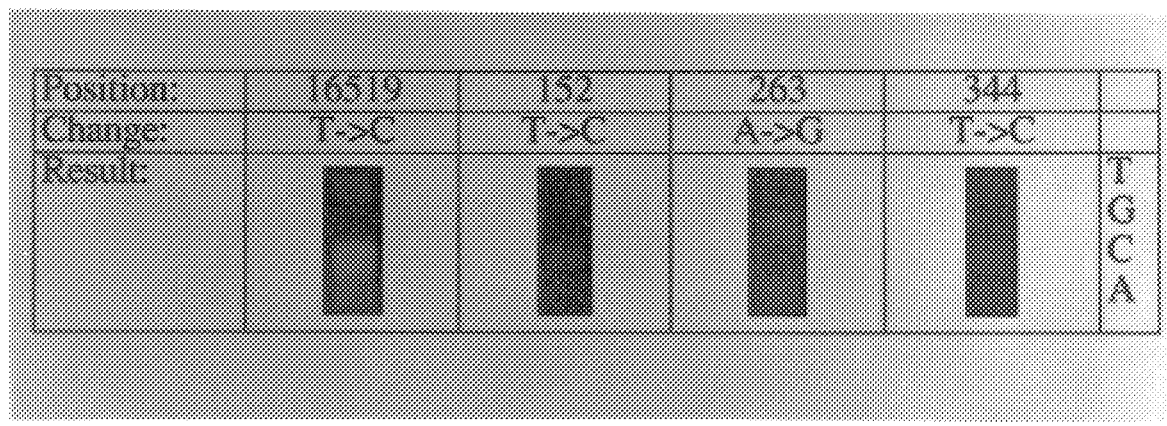

FIG. 19 illustrates the detection of 4 transitions in the target sequence relative to the wild-type probes on the chip in FIG. 18.

Figures 20, 21:
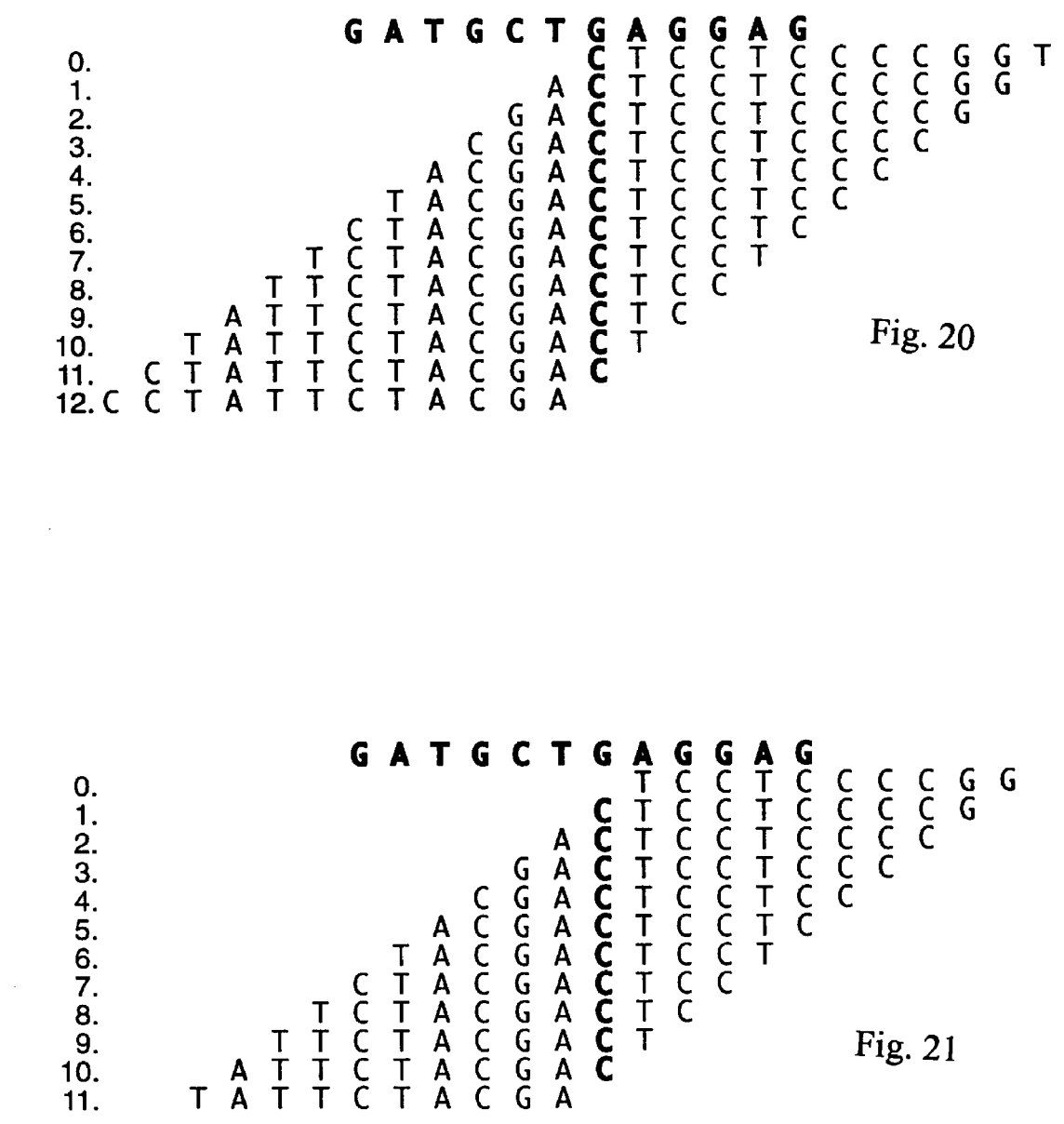

FIG. 20 shows the alignment of some of the probes on a $p^{53}$ DNA chip with a 12-mer model target nucleic acid. The SEQ ID. NOS. corresponding to the fourteen peptide sequences shown in FIG. 20 are 334–347, respectively.

FIG. 21 shows a set of 10-mer probes for a p53 exon 6 DNA chip. The SEQ ID. NOS. corresponding to the thirteen peptide sequences shown in FIG. 21 are 334 and 348–359, respectively.

Figure 22:
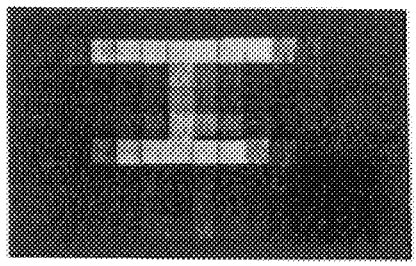
Figure 22:
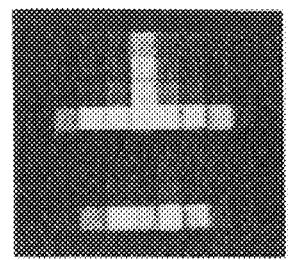
Figure 22:
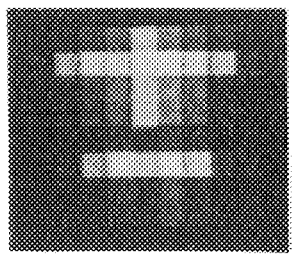
Figure 22:
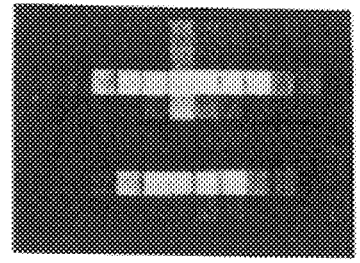
Figure 23A:
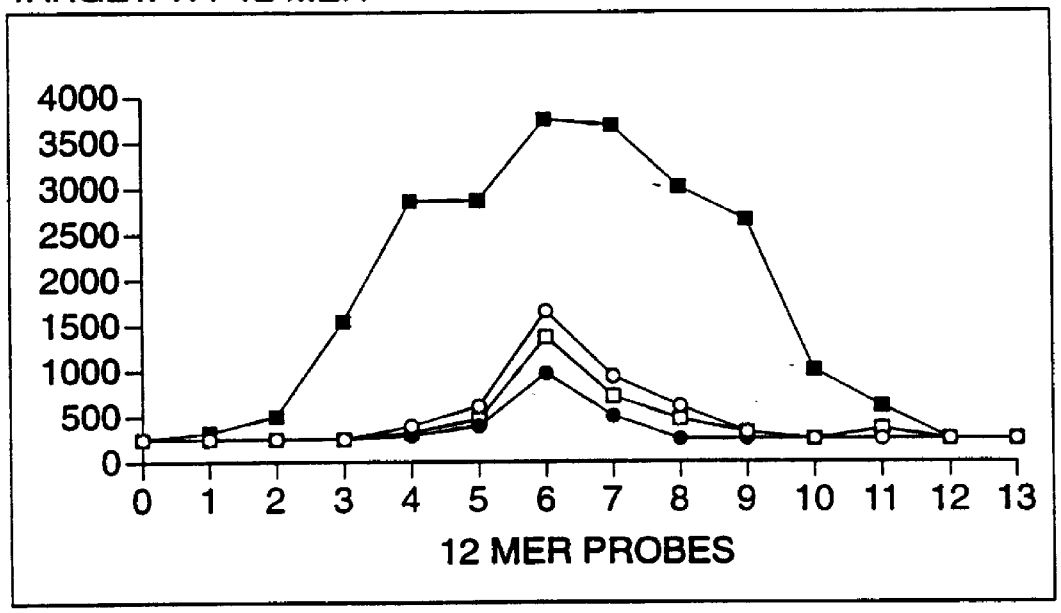
Figure 23A:
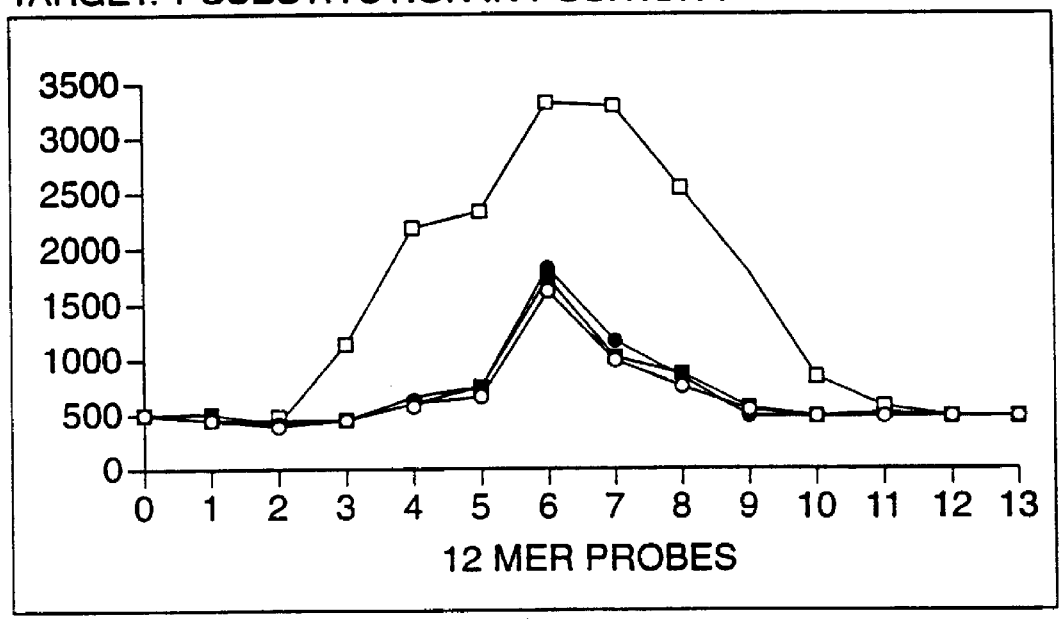
Figure 23B:
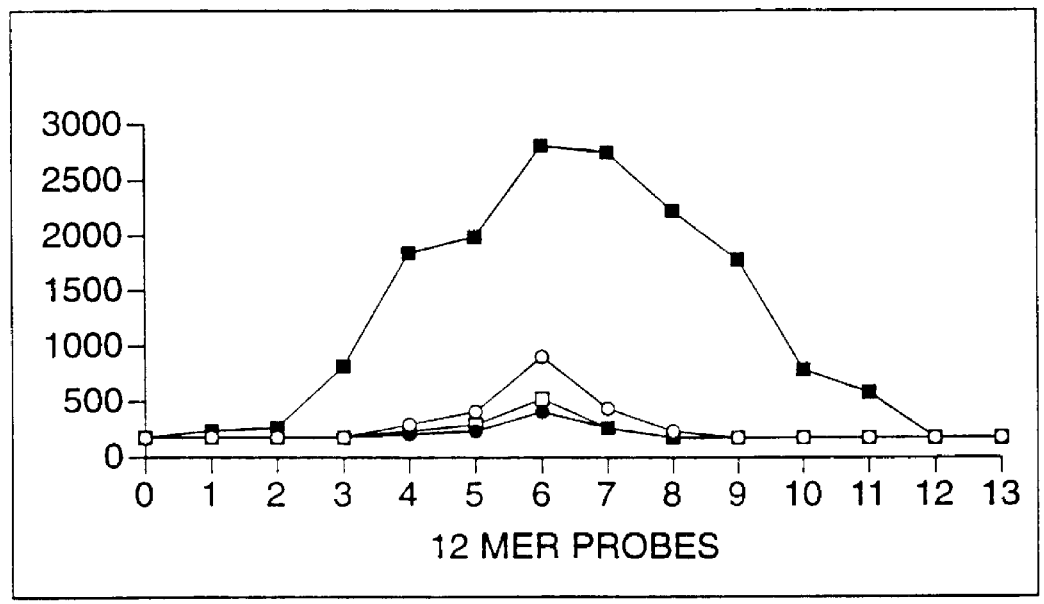
Figure 23B:
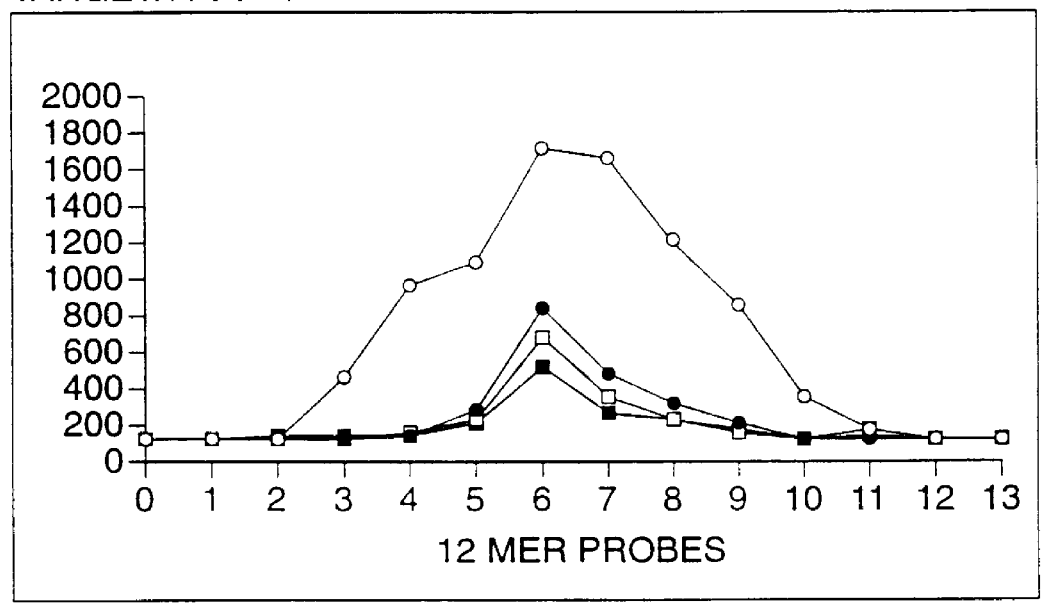

FIG. 22 shows that very distinct patterns are observed after hybridization of p53 DNA chips with targets having different 1 base substitutions. In the first image in FIG. 22, the 12-mer probes that form perfect matches with the wild-type target are in the first row (top). The 12-mer probes with single base mismatches are located in the second, third, and fourth rows and have much lower signals.

FIG. 23, in graphs 2, 3, and 4, graphically depicts the data in FIG. 22. On each graph, the X ordinate is the position of the probe in its row on the chip, and the Y ordinate is the signal at that probe site after hybridization.

Figure 24:
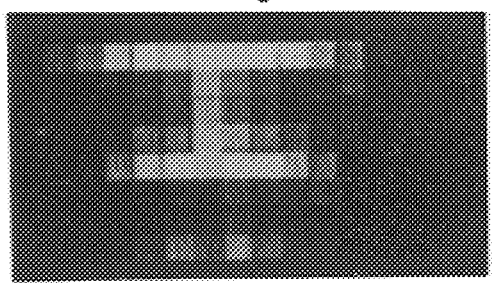
Figure 25A:
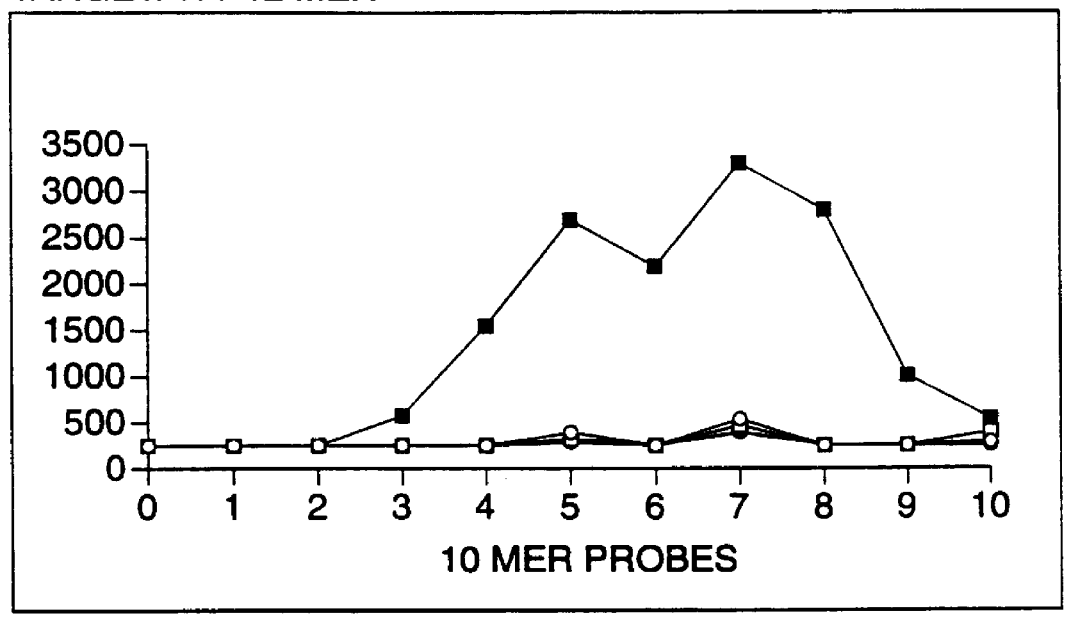
Figure 25A:
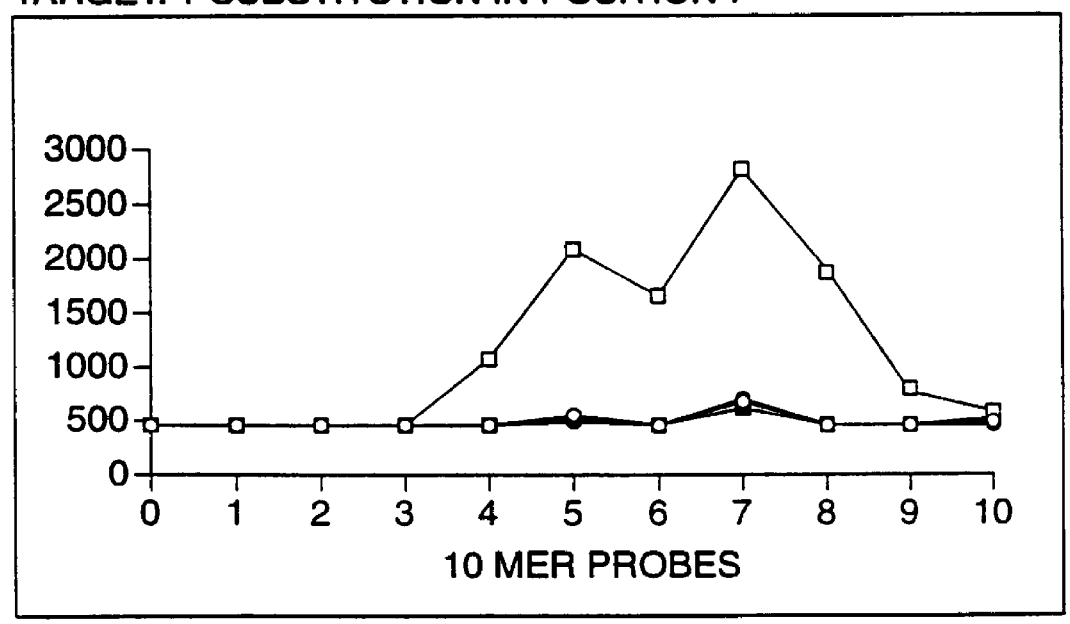
Figure 25B:
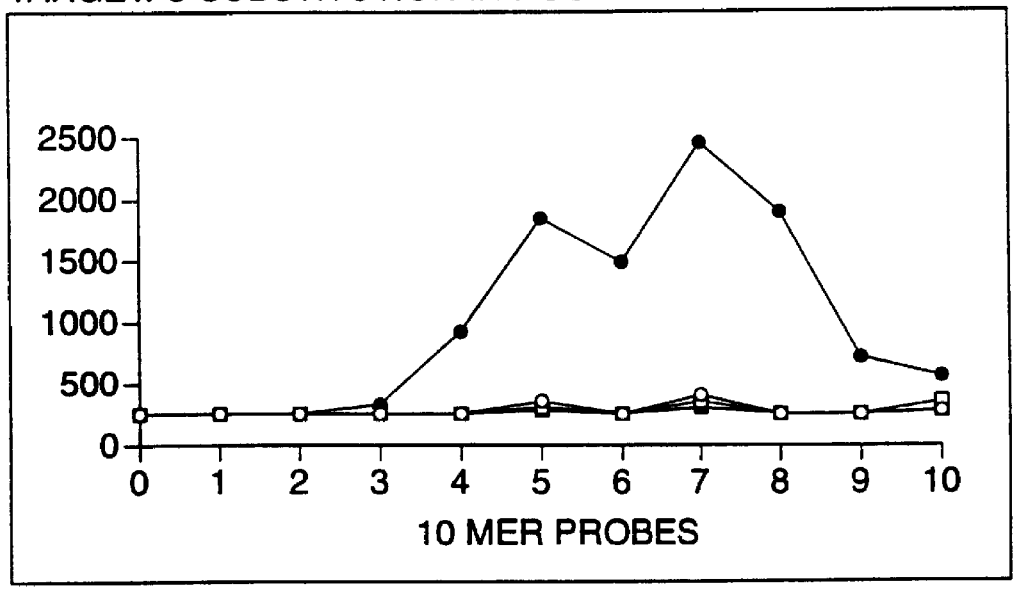
Figure 25B:
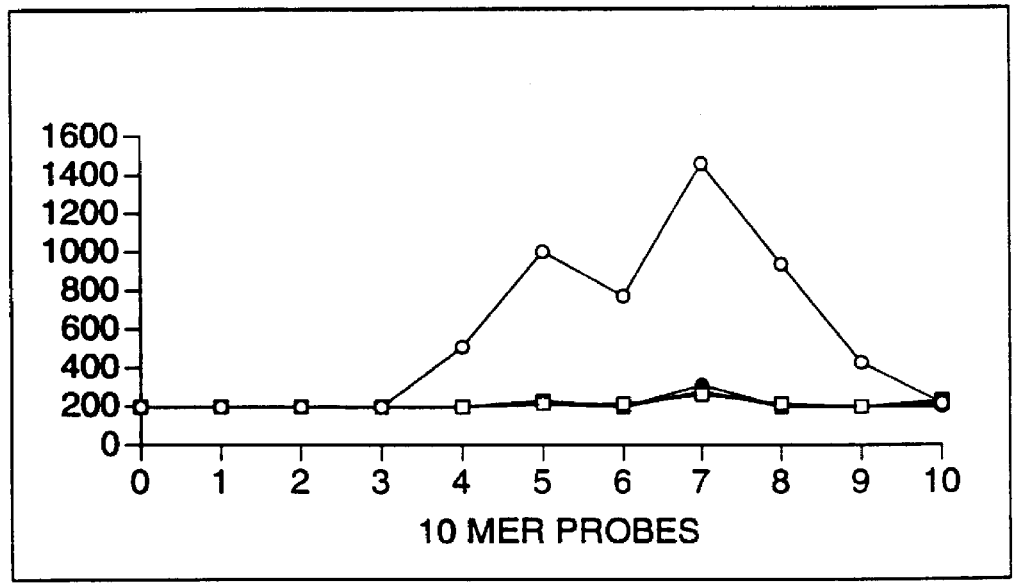

FIG. 24 shows the results of hybridizing mixed target populations of WT and mutant p53 genes to the p53 DNA chip.

Figure 26:
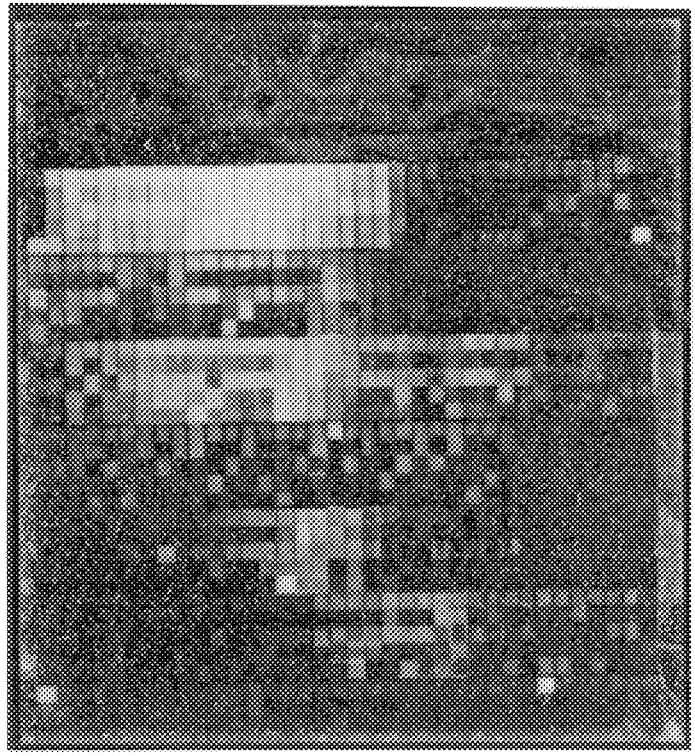

FIG. 25, in graphs 1–4, shows (see FIG. 23 as well) the hybridization efficiency of a 10-mer probe array as compared to a 12-mer probe array FIG. 26 shows an image of a p53 DNA chip hybridized to a target DNA.

Figure 27:
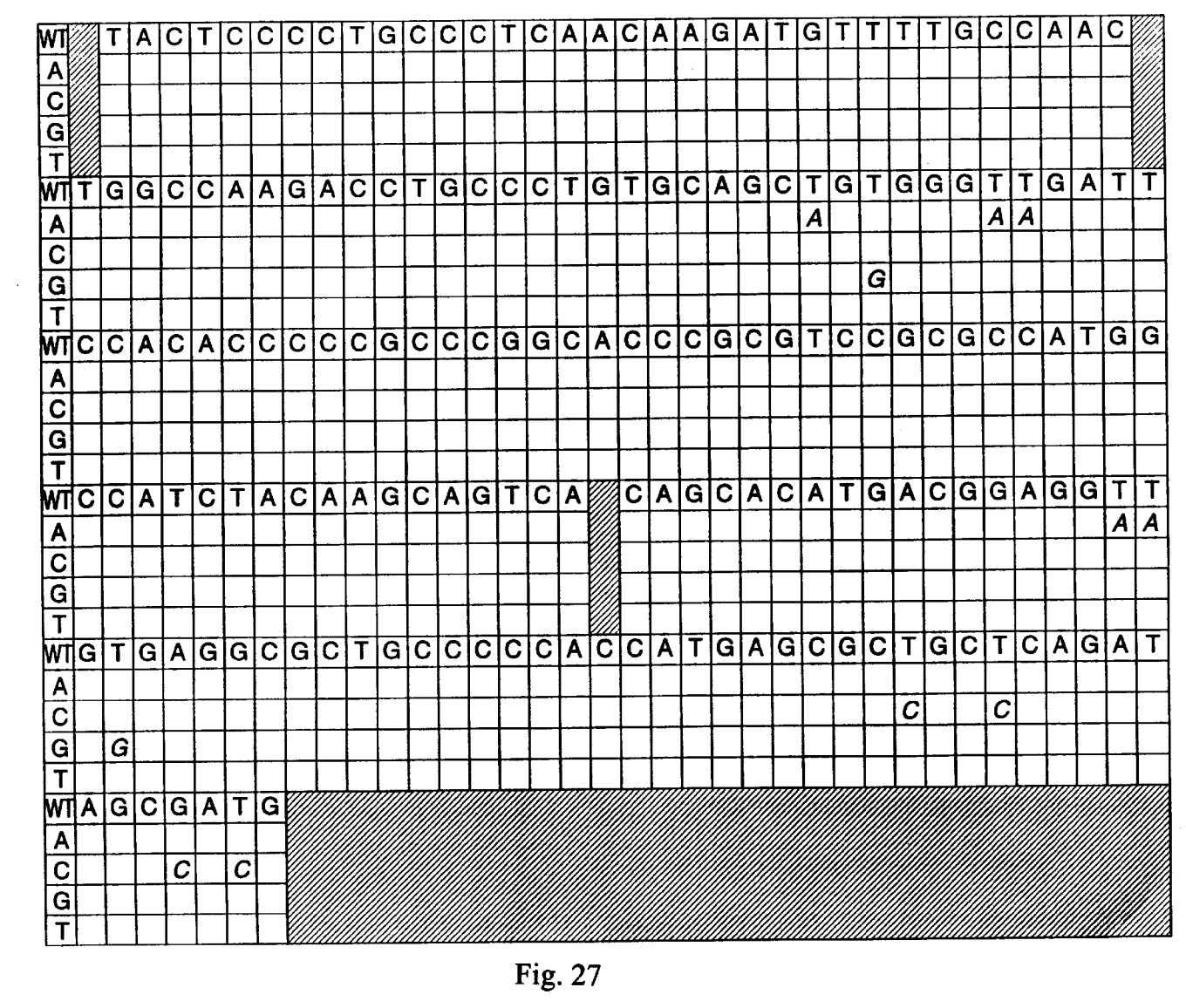

FIG. 27 illustrates how the actual sequence was read from the chip shown in FIG. 26. Gaps in the sequence of letters in the WT rows correspond to control probes or sites. Positions at which bases are miscalled are represented by letters in italic type in cells corresponding to probes in which the WT bases have been substituted by other bases. The SEQ ID. NO. corresponding to the peptide sequence shown in FIG. 27 is 360.

Figure 28:
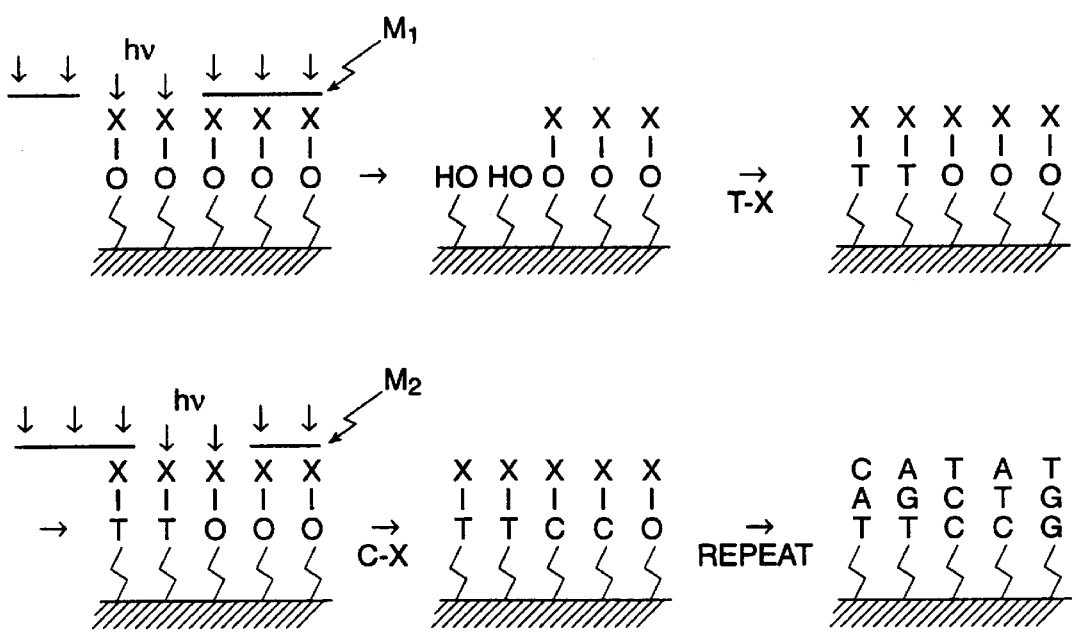

FIG. 28 illustrates the VLSIPS™ technology as applied to the light directed synthesis of oligonucleotides. Light (hv) is shone through a mask ($M_1$) to activate functional groups (—OH) on a surface by removal of a protecting group (X). Nucleoside building blocks protected with photoremovable protecting groups (T-X, C-X) are coupled to the activated areas. By repeating the irradiation and coupling steps, very complex arrays of oligonucleotides can be prepared.

Figure 29:
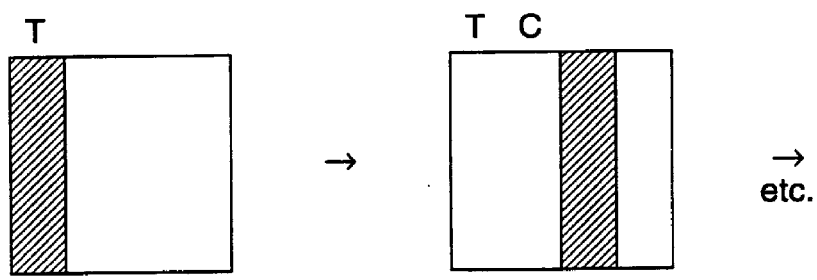
Figure 29:
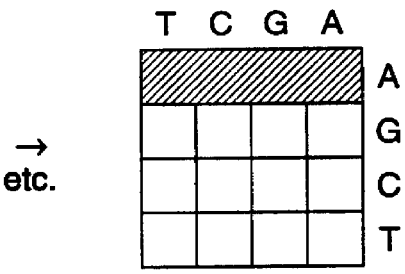
Figure 29:
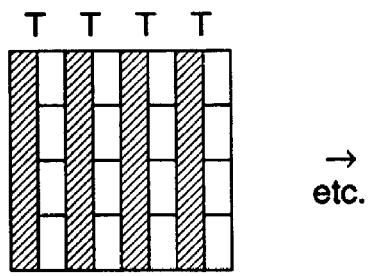

FIG. 29 illustrates how the VLSIPS™ process can be used to prepare "nucleoside combinatorials" or oligonucleotides synthesized by coupling all four nucleosides to form dimers, trimers, etc.

Figure 30:
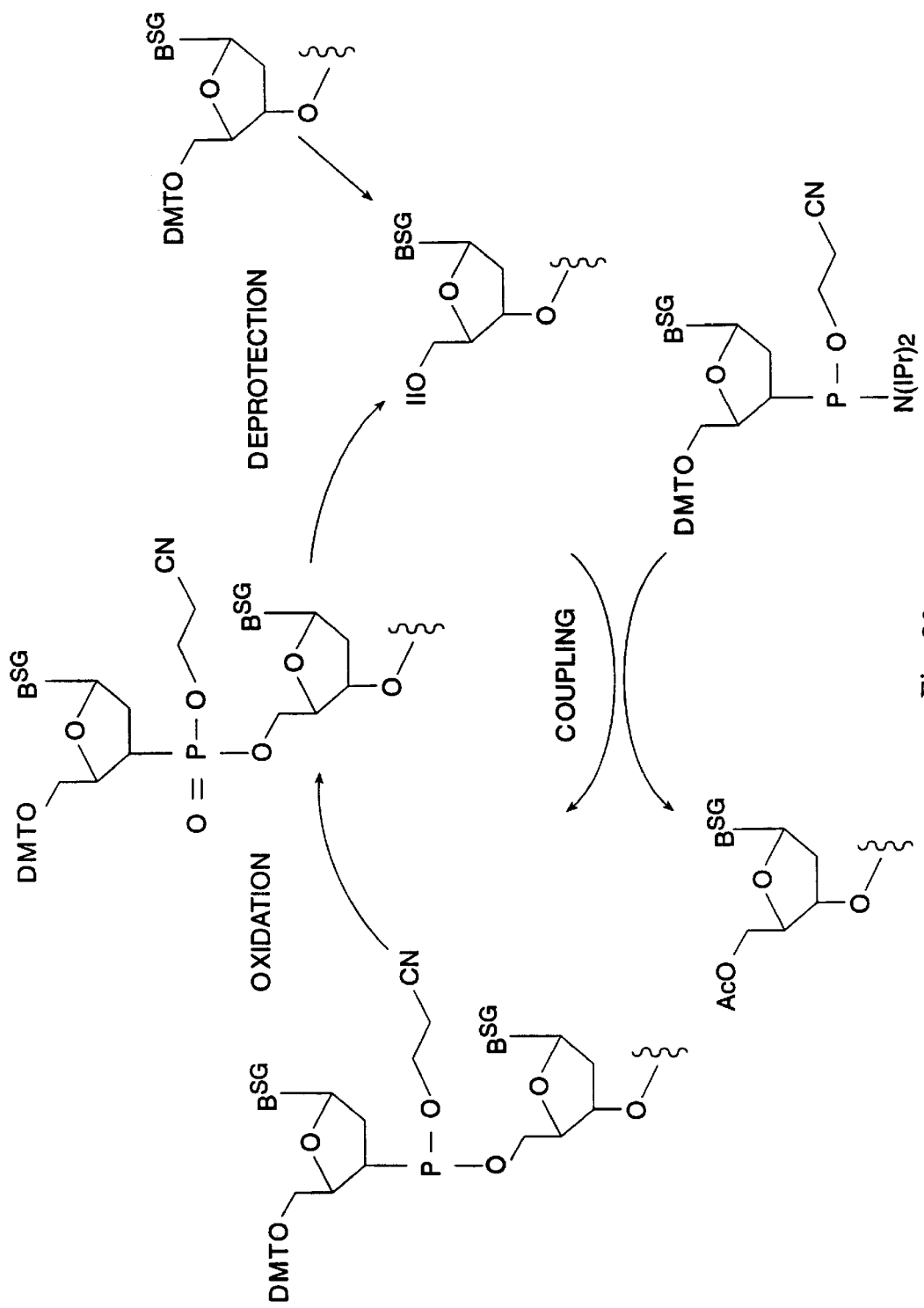

FIG. 30 shows the deprotection, coupling, and oxidation steps of a solid phase DNA synthesis method.

Figure 31:
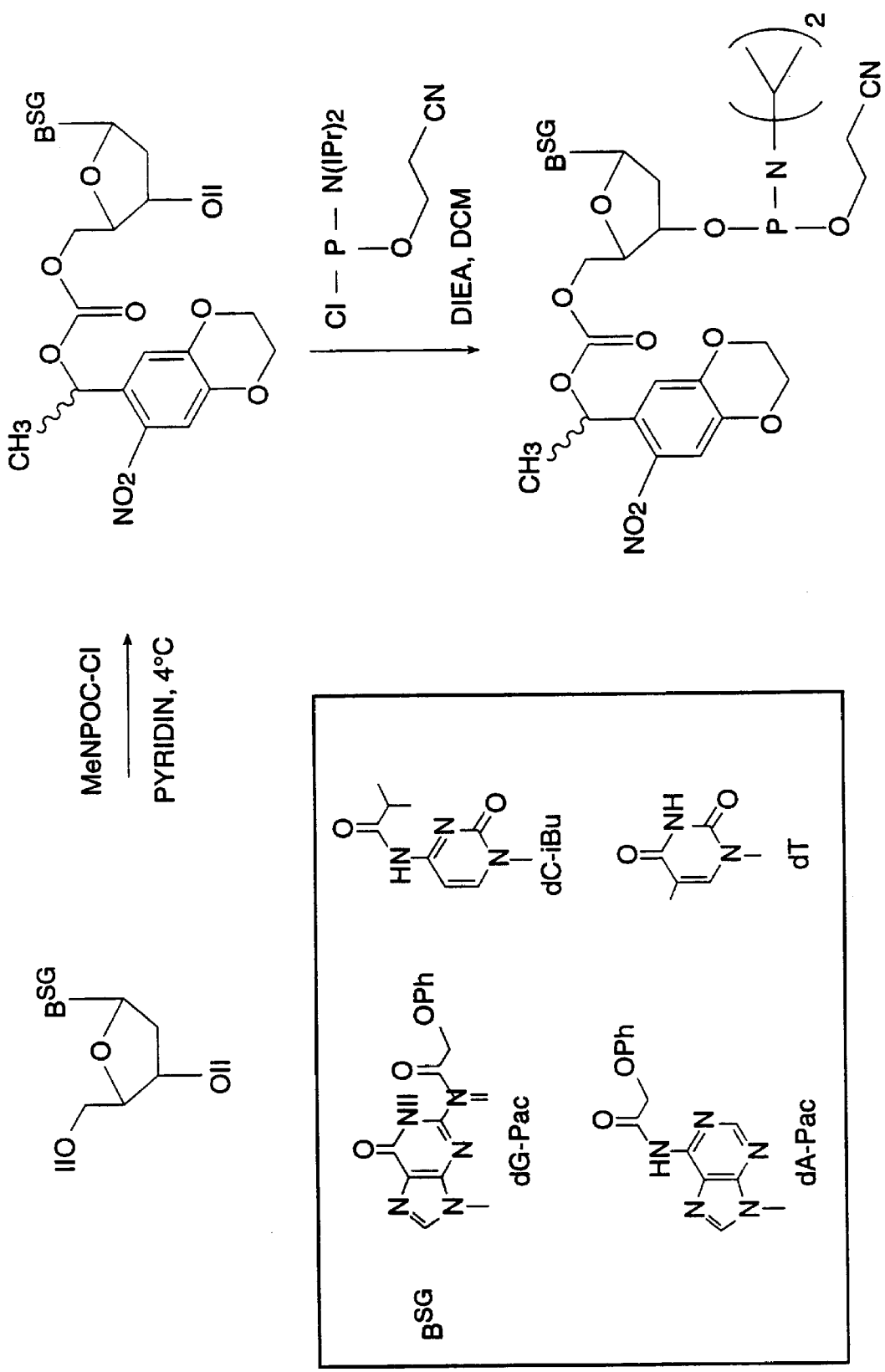

FIG. 31 shows an illustrative synthesis route for the nucleoside building blocks used in the VLSIPS™ method.

Figure 32:
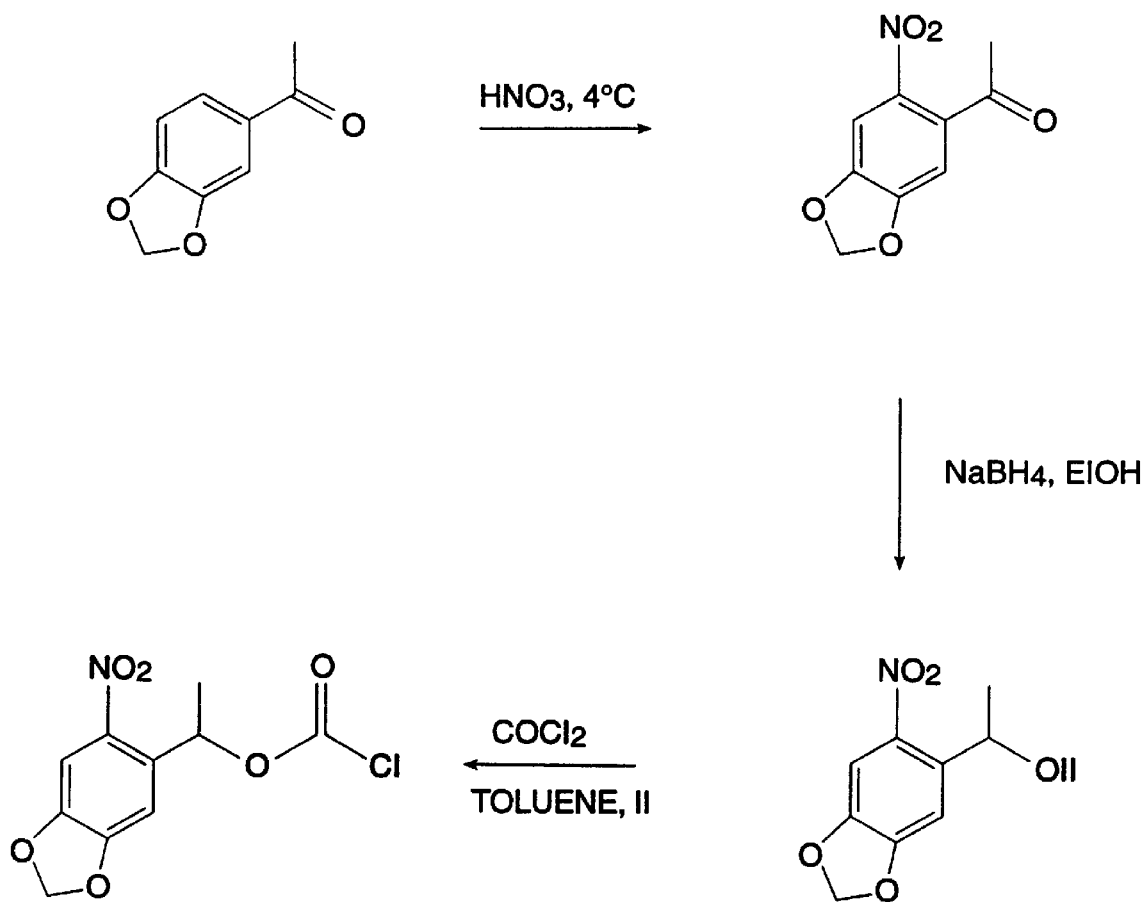

FIG. 32 shows a preferred photoremovable protecting group, MeNPOC, and how to prepare the group in active form.

Figure 33:
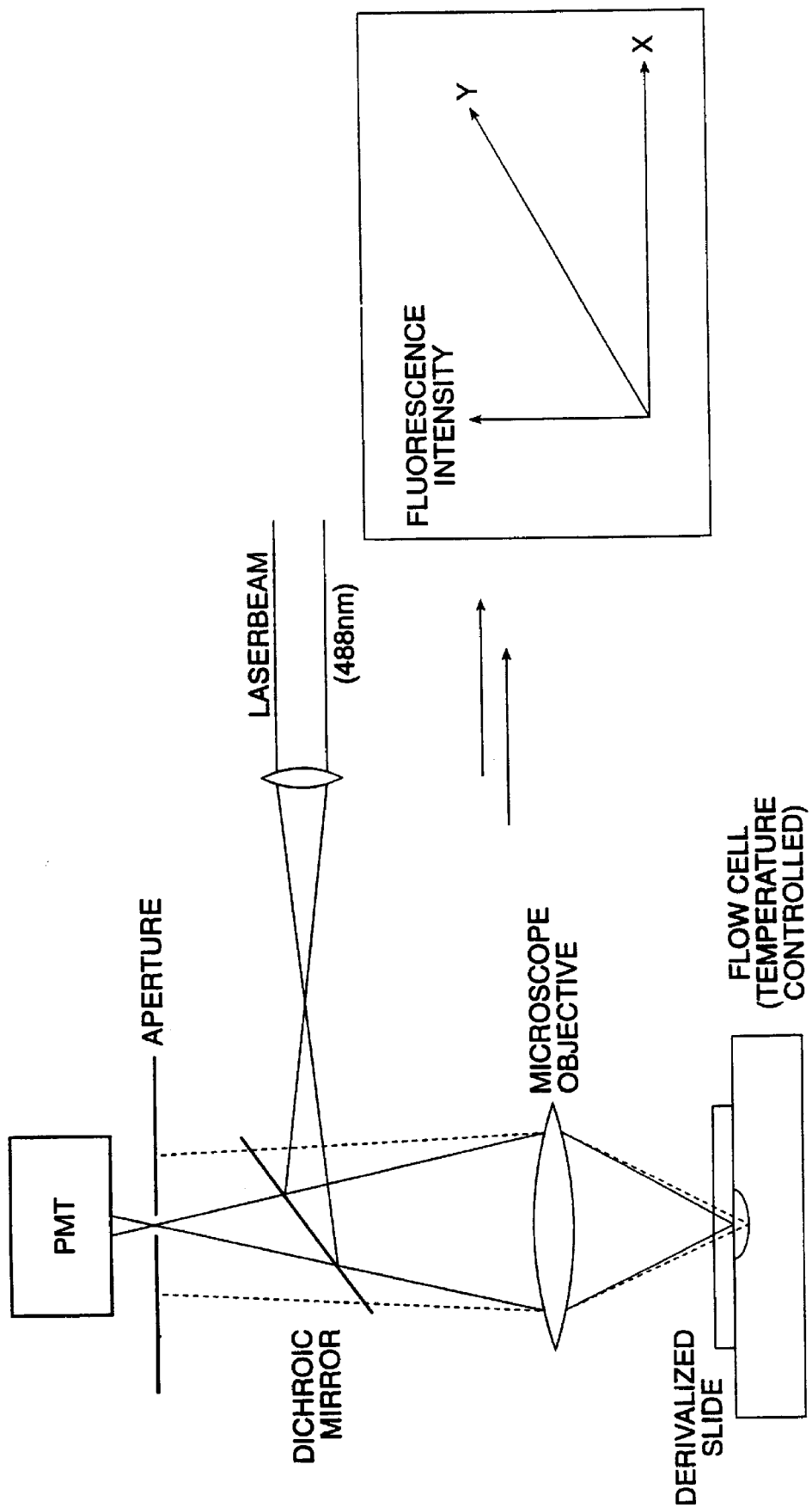

FIG. 33 illustrates an illustrative detection system for scanning a DNA chip.

DETAILED DESCRIPTION OF THE INVENTION

Using the VLSIPS™ method, one can synthesize arrays of many thousands of oligonucleotide probes on a substrate, such as a glass slide or chip. The method can be used, for instance, to synthesize "combinatorial" arrays consisting of, for example, all possible octanucleotides. Such arrays can be used for primary sequencing-by-hybridization on genomic DNA fragments or other nucleic acids or to detect mutations in a target nucleic acid for which the normal or "wild-type" nucleotide sequence is already known. Using the preferred method of the invention, one employs a strategy called "tiling" to synthesize specific sets of probes or at spatially-defined locations on a substrate, creating the novel probe arrays and "DNA chips" of the invention.

Figure 1:
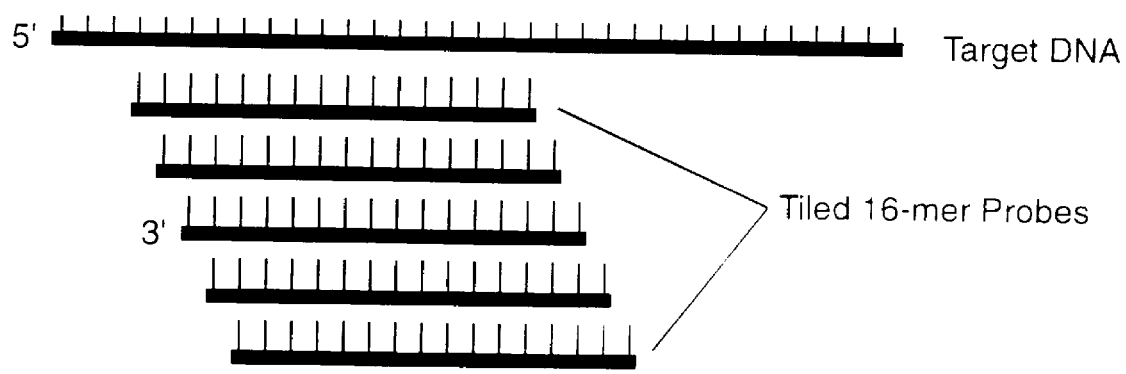
FIG. 1 shows how the tiling method of the invention defines a set of DNA probes relative to a target nucleic acid.

To illustrate the tiling method of the invention, consider the problem of detecting mutations at one or more position in the nucleotide sequence of a target nucleic acid with oligonucleotide probes of defined length. The length (L) of the probe is typically expressed as the number of nucleotides or bases in a single-stranded nucleic acid probe. For purposes of the present invention, lengths ranging from 12 to 18 bases are preferred, although shorter and longer lengths can also be employed. To employ the tiling method, one synthesizes a set of probes defined by the particular nucleotide sequence of interest in the target nucleic acid. For each base in the target DNA segment, one synthesizes a probe complementary to the subsequence of the target nucleic acid beginning at that base and ending L-1 bases to the 3'-side (see FIG. 1).

In a preferred embodiment of the invention, the probes are arranged (either by immobilization, typically by covalent attachment, of a pre-synthesized probe or by synthesis of the probe on the substrate) on the substrate or chips in lanes stretching across the chip and separated, and these lanes are in turned arranged in blocks of preferably 5 lanes, although blocks of other sizes will have useful application, as will be apparent from the following illustration. The first of these five lanes, called the "wild-type lane", contains probes arranged in order of sequence, and all of the probes are complementary to a specified wild-type nucleic acid sequence. The other four lanes contain probe sets for detecting all possible single-base mutations in the defined sequence; in turn, these probe sets are defined by a position of potential non-complementarity in the probe relative to the target (i.e., a single base mismatch) and the identity of the nucleotide in the probe at that position (i.e., whether the nucleotide is an A, C, G, or T nucleotide). The position of mismatch, also called the position of substitution, is preferably selected to be near the center of the probes, i.e., position 7 of a probe of L=15.

For each probe in the wild-type lane, one synthesizes four probes (one for each of the lanes other than the wild-type lane), Three of these four probes is identical to the corresponding wild-type probe but for the base at the position of substitution, and the remaining probe is identical to the wild-type probe. This set of four substitution probes is preferably placed in a column directly below (or above) the corresponding wild-type probe, thus creating an A-lane, a C-lane, a G-lane, and a T-lane. FIG. 2 shows an illustrative tiled array of the invention with probes for the detection of point mutations. The base at the position of substitution in each of the wild-type probes is shown in the wild-type lane, and the shading shows the location of the substitution probe having the wild-type sequence. Below are the probes that would be placed in the column marked by the arrow if the probe length were 15 and the position of substitution were 7.

3'-CCGACTGCAGTCGTT (SEQ. ID. NO:1)
3'-CCGACTACAGTCGTT (SEQ. ID. NO:2)
3'-CCGACTCCAGTCGTT (SEQ. ID. NO:3)
3'-CCGACTGCAGTCGTT (SEQ. ID. NO:1)
3'-CCGACTTCAGTCGTT (SEQ. ID. NO:4)

Thus, the substitution lanes occupy four of the five lanes separating successive wild-type lanes on the chip; the blocks of five lanes can be separated by a sixth lane for measurement of background signals.

The DNA chips of the invention have a wide variety of applications. In one embodiment, the DNA chip is used to select an optimal probe from an array of probes. In this embodiment, an array of probes of variable length and sequences is synthesized and then hybridized to a target nucleic acid of known sequence. The pattern of hybridization reveals the optimal length and sequence composition of probes to detect a particular mutation or other specific sequence of nucleotides. In some circumstances, i.e., target nucleic acids with repeated sequences or with high G/C content, very long probes may be required for optimal detection. In one embodiment for detecting specific sequences in a target nucleic acid with a DNA chip, repeat sequences are detected as follows. The chip comprises probes of length sufficient to extend into the repeat region varying distances from each end. The sample, prior to hybridization, is treated with a labeled oligonucleotide that is complementary to a repeat region but shorter than the full length of the repeat. The target nucleic is labeled with a second, distinct label. After hybridization, the chip is scanned for probes that have bound both the labeled target and the labeled oligonucleotide probe; the presence of such bound probes shows that at least two repeat sequences are present.

A variety of methods can be used to enhance detection of labeled targets bound to a probe on the array. In one embodiment, the protein MutS (from *E. coli*) or equivalent proteins such as yeast MSH1, MSH2, and MSH3; mouse Rep-3, and Streptococcus Hex-A, is used in conjunction with target hybridization to detect probe-target complex that contain mismatched base pairs. The protein, labeled directly or indirectly, can be added to the chip during or after hybridization of target nucleic acid, and differentially binds to homo- and heteroduplex nucleic acid. A wide variety of dyes and other labels can be used for similar purposes. For instance, the dye YOYO-1 is known to bind preferentially to nucleic acids containing sequences comprising runs of 3 or more G residues.

The DNA chips produced by the methods of the invention can be used to study and detect mutations in exons of human genes of clinical interest, including point mutations and deletions. In the following sections, the method of the invention is illustrated by the detection of mutations in a variety of clinically and medically significant human nucleic acid sequences. Thus, the invention is illustrated first with respect to the preparation of DNA chips for the detection of mutations associated with cystic fibrosis, then with DNA chips for the detection of human mitochondrial DNA sequences, then with DNA chips for the detection of mutations in the human p53 gene associated with cancer, and finally with respect to the detection of mutations in the HIV RT gene associated with drug resistance.

Detection of Cystic Fibrosis Mutations with DNA Chips

A number of years ago, cystic fibrosis, the most common severe autosomal recessive disorder in humans, was shown to be associated with mutations in a gene thereafter named the Cystic Fibrosis Transmembrane Conductance Regulator (CFTR) gene. The sequences of the exons and parts of the introns in the gene are known, as are the changes corresponding to several hundred known mutations. Several tests have been developed for detecting the most frequent of these mutations. The present invention provides CFTR gene oligonucleotide arrays (DNA chips) that can be used to identify mutations in the CFTR gene rapidly and efficiently.

The methods used to make the high-density DNA chips of the invention allow probes for long stretches of DNA coding regions to be directly "written" onto the chips in the form of sets of overlapping oligonucleotides. These methods have been used to develop a number of useful CFTR gene chips, one illustrative chip bears an array of 1296 probes covering the full length of exon 10 of the CFTR gene arranged in a 36×36 array of 356 λm elements. The probes in the array can have any length, preferably in the range of from 10 to 18 residues and can be used to detect and sequence any single-base substitution and any deletion within the 192-base exon, including the three-base deletion known as ΔF508. As described in detail below, hybridization of sub-nanomolar concentrations of wild-type and ΔF508 oligonucleotide target nucleic acids labeled with fluorescein to these arrays produces highly specific signals (detected with confocal scanning fluorescence microscopy) that permit discrimination between mutant and wild-type target sequences in both homozygous and heterozygous cases. The method and chips of the invention can also be used to detect other known mutations in the CFTR gene, as described in detail below.

The most common cystic fibrosis mutation is known as ΔF508, because the mutation is a three-base deletion that results in the removal of amino acid #508 from the CFTR protein. The present invention provides DNA chips for detecting ΔF508, one such chip results from applying the tiling method to exon 10 of the CFTR gene, the exon to which ΔF508 has been mapped. The tiling method involved the synthesis of a set of probes of a selected length in the range of from 10 to 18 bases and complementary to subsequences of the known wild-type CFTR sequence starting at a position a few bases into the intron on the 5'-side of exon 10 and ending a few bases into the intron on the 3'-side. There was a probe for each possible subsequence of the given segment of the gene, and the probes were organized into a "lane" in such a way that traversing the lane from the upper left-hand corner of the chip to the lower righthand corner corresponded to traversing the gene segment base-by-base from the 5'-end. The lane containing that set of probes is, as noted above, called the "wild-type lane."

Relative to the wild-type lane, a "substitution" lane, called the "A-lane", was synthesized on the chip. The A-lane probes were identical in sequence to an adjacent (immediately below the corresponding) wild-type probe but contained, regardless of the sequence of the wild-type probe, a dA residue at position 7 (counting from the 3'-end). In similar fashion, substitution lanes with replacement bases dC, dG, and dT were placed onto the chip in a "C-lane," a "G-lane," and a "T-lane," respectively. A sixth lane on the chip consisted of probes identical to those in the wild-type lane but for the deletion of the base in position 7 and restoration of the original probe length by addition to the 5'-end the base complementary to the gene at that position.

The four substitution lanes enable one to deduce the sequence of a target exon 10 nucleic acid from the relative intensities with which the target hybridizes to the probes in the various lanes. The probe organization on the chip can be conveniently columnar, and the set of probes consisting of a wild-type probe and four corresponding substitution probes is referred to as a "column set." One and only one of the four substitution probes in a column set has exactly the same sequence as the wild-type probe in the set. Those of skill in the art will appreciate that, in other embodiments of the invention, one could delete one or more lanes or columns and still benefit from the invention. Various versions of such exon 10 DNA chips were made as described above with probes 15 bases long, as well as chips with probes 10, 14, and 18 bases long. For the results described below, the probes were 15 bases long, and the position of substitution was 7 from the 3'-end.

To demonstrate the ability of the chip to distinguish the ΔF508 mutation from the wild-type, two synthetic target nucleic acids were made. The first, a 39-mer complementary to a subsequence of exon 10 of the CFTR gene having the three bases involved in the ΔF508 mutation near its center, is called the "wild-type" or wt508 target, corresponds to positions 111–149 of the exon, and has the sequence shown below:

5'-CATTAAAGAAAATATCATCTTTGGTGTTTCCTAT-
GATGA (SEQ. ID NO: 5).
The second, a 36-mer probe derived from the wild-type target by removing those same three bases, is called the "mutant" target or mu508 target and has the sequence shown below, first with dashes to indicate the deleted bases, and then without dashes but with one base underlined (to indicate the base detected by the T-lane probe, as discussed below):
5'-C A T T A A A G A A A A T A T C A T - - -
TGGTGTTTCCTATGATGA; (SEQ. ID NO:6)
5'-CATTAAAGAAAATATCATTGGTGTTTCCTATGATGA.
(SEQ. ID NO:7)
Both targets were labeled with fluorescein at the 5'-end.

In three separate experiments, the wild-type target, the mutant target, and an equimolar mixture of both targets was exposed (0.1 nM wt508, 0.1 nM mu508, and 0.1 nM wt508 plus 0.1 nM mu508, respectively, in a solution compatible with nucleic acid hybridization) to a CF chip. The hybridization mixture was incubated overnight at room temperature, and then the chip was scanned on a reader (a confocal fluorescence microscope in photon-counting mode; images of the chip were constructed from the photon counts) at several successively higher temperatures while still in contact with the target solution. After each temperature change, the chip was allowed to equilibrate for approximately one-half hour before being scanned. After each set of scans, the chip was exposed to denaturing solvent and conditions to wash, i.e., remove target that had bound, the chip so that the next experiment could be done with a clean chip.

The results of the experiments are shown in FIGS. 3, 4, 5, and 6. FIG. 3, in panels A, B, and C, shows an image made from the region of a DNA chip containing CFTR exon 10 probes; in panel A, the chip was hybridized to a wild-type target; in panel C, the chip was hybridized to a mutant delta 508 target; and in panel B, the chip was hybridized to a mixture of the wild-type and mutant targets. FIG. 4, in sheets 1–3, corresponding to panels A, B, and C of FIG. 3, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest").

These figures show that, for the wild-type target and the equimolar mixture of targets, the substitution probe with a nucleotide sequence identical to the corresponding wild-type probe bound the most target, allowing for an unambiguous assignment of target sequence as shown by letters near the points on the curve. The target wt508 thus hybridized to the probes in the wild-type lane of the chip, although the strength of the hybridization varied from probe-to-probe, probably due to differences in melting temperature. The sequence of most of the target can thus be read directly from the chip, by inference from the pattern of hybridization in the lanes of substitution probes (if the target hybridizes most intensely to the probe in the A-lane, then one infers that the target has a T in the position of substitution, and so on).

For the mutant target, the sequence could similarly be called on the 3'-side of the deletion. However, the intensity of binding declined precipitously as the point of substitution approached the site of the deletion from the 3'-end of the target, so that the binding intensity on the wild-type probe whose point of substitution corresponds to the T at the 3'-end of the deletion was very close to background. Following that pattern, the wild-type probe whose point of substitution corresponds to the middle base (also a T) of the deletion bound still less target. However, the probe in the T-lane of that column set bound the target very well.

Examination of the sequences of the two targets reveals that the deletion places an A at that position when the sequences are aligned at their 3'-ends and that the T-lane probe is complementary to the mutant target with but two mismatches near an end (shown below in lower-case letters, with the position of substitution underlined):
Target: 5'-CATTAAAGAAAATATCATTGGTGT-
TTCCTATGATGA
Probe: 3'-TagTAGTAACCACAA (SEQ. ID NO:8)
Thus the T-lane probe in that column set calls the correct base from the mutant sequence. Note that, in the graph for the equimolar mixture of the two targets, that T-lane probe binds almost as much target as does the A-lane probe in the same column set, whereas in the other column sets, the probes that do not have wild-type sequence do not bind target at all as well. Thus, that one column set, and in particular the T-lane probe within that set, detects the ΔF508 mutation under conditions that simulate the homozygous case and also conditions that simulate the heterozygous case.

The present invention thus provides individual probes, sets of probes, and arrays of probe sets on chips, in specific patterns, as the probes provide important benefits for detecting the presence of specific exon 10 sequences. The sequences of several important probes of the invention are shown below. In each case, the letter "X" stands for the point of substitution in a given column set, so each of the sequences actually represents four probes, with A, C, G, and T, respectively, taking the place of the "X." Sets of shorter probes derived from the sets shown below by removing up to five bases from the 5'-end of each probe and sets of longer probes made from this set by adding up to three bases from the exon 10 sequence to the 5'-end of each probe, are also useful and provided by the invention.
3'-TTTATAXTAGAAACC (SEQ. ID NO:9)
3'-TTATAGXAGAAACCA (SEQ. ID NO:10)
3'-TATAGTXGAAACCAC (SEQ. ID NO:11)
3'-ATAGTAXAAACCACA (SEQ. ID NO:12)
3'-TAGTAGXAACCACAA (SEQ. ID NO:13)
3'-AGTAGAXACCACAAA (SEQ. ID NO:14)
3'-GTAGAAXCCACAAAG (SEQ. ID NO:15)
3'-TAGAAAXCACAAAGG (SEQ. ID NO:16)
3'-AGAAACXACAAAGGA (SEQ. ID NO:17)

Although in this example the sequence could not be reliably deduced near the ends of the target, where there is not enough overlap between target and probe to allow effective hybridization, and around the center of the target, where hybridization was weak for some other reason, perhaps high AT-content, the results show the method and the probes of the invention can be used to detect the mutation of interest. The mutant target gave a pattern of hybridization that was very similar to that of the wt508 target at the ends, where the two share a common sequence, and very different in the middle, where the deletion is located. As one scans the image from right to left, the intensity of hybridization of the target to the probes in the wild-type lane drops off much more rapidly near the center of the image for mu508 than for wt508; in addition, there is one probe in the T-lane that hybridizes intensely with mu508 and hardly at all with wt508. The results from the equimolar mixture of the two targets, which represents the case one would encounter in testing a heterozygous individual for the mutation, are a blend of the results for the separate targets, showing the power of the invention to distinguish a wild-type target sequence from one containing the ΔF508 mutation and to detect a mixture of the two sequences.

The results above clearly demonstrate how the DNA chips of the invention can be used to detect a deletion mutation, ΔF508; another model system was used to show that the chips can also be used to detect a point mutation as well. One of the more frequent mutations in the CFTR gene is G480C, which involves the replacement of the G in position 46 of exon 10 by a T, resulting in the substitution of a cysteine for the glycine normally in position #480 of the CFTR protein. The model target sequences included the 21-mer probe wt480 to represent the wild-type sequence at positions 37–55 of exon 10: 5'-CCTTCAGAGGGTAAAATTAAG (SEQ. ID NO:18) and the 21-mer probe mu480 to represent the mutant sequence: 5'-CCTTCAGAGTGTAAAATTAAG (SEQ. ID NO:19).

terns. The wild-type sequence could easily be read from the chip, but the probe that bound the mu480 target so well when only the mu480 target was present also bound it well when both the mutant and wild-type targets were present in a mixture, making the hybridization pattern easily distinguishable from that of the wild-type target alone. These results again show the power of the DNA chips of the invention to detect point mutations in both homo- and heterozygous individuals.

To demonstrate clinical application of the DNA chips of the invention, the chips were used to study and detect mutations in nucleic acids from genomic samples. Genomic samples from a individual carrying only the wild-type gene and an individual heterozygous for ΔF508 were amplified by PCR using exon 10 primers containing the promoter for T7 RNA polymerase. Illustrative primers of the invention are shown below.

| Exon | Name | Sequence | |
|---|---|---|---|
| 10 | CFi9-T7 | TAATACGACTCACTATAGGGAGatgacctaataatgatgggttt | (SEQ. ID. NO:20) |
| 10 | CFi10c-T7 | TAATACGACTCACTATAGGGAGtagtgtgaagggttcatatgc | (SEQ. ID. NO:21) |
| 10 | CFi10c-T3 | CTCGGAATTAACCCTCACTAAAGGtagtgtgaagggttcatatg | (SEQ. ID. NO:22) |
| 10, 11 | CFi10-T7 | TAATACGACTCACTATAGGGAGagcatactaaaagtgactctc | (SEQ. ID. NO:23) |
| 11 | CFi11c-T7 | TAATACGACTCACTATAGGGAGacatgaatgacatttacagcaa | (SEQ. ID. NO:24) |
| 11 | CFi11c-T3 | CGGAATTAACCCTCACTAAAGGacatgaatgacatttacagcaa | (SEQ. ID. NO:25) |

In separate experiments, a DNA chip was hybridized to each of the targets wt480 and mu480, respectively, and then scanned with a confocal microscope. FIG. 5, in panels A, B, and C, shows an image made from the region of a DNA chip containing CFTR exon 10 probes; in panel A, the chip was hybridized to the wt480 target; in panel C, the chip was hybridized to the mu480 target; and in panel B, the chip was hybridized to a mixture of the wild-type and mutant targets. FIG. 6, in sheets 1–3, corresponding to panels A, B, and C of FIG. 5, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest").

These figures show that the chip could be used to sequence a 16-base stretch from the center of the target wt480 and that discrimination against mismatches is quite good throughout the sequenced region. When the DNA chip was exposed to the target mu480, only one probe in the portion of the chip shown bound the target well: the probe in the set of probes devoted to identifying the base at position 46 in exon 10 and that has an A in the position of substitution and so is fully complementary to the central portion of the mutant target. All other probes in that region of the chip have at least one mismatch with the mutant target and therefore bind much less of it. In spite of that fact, the sequence of mu480 for several positions to both sides of the mutation can be read from the chip, albeit with much-reduced intensities from those observed with the wild-type target.

The results also show that, when the two targets were mixed together and exposed to the chip, the hybridization pattern observed was a combination of the other two pat- These primers can be used to amplify exon 10 or exon 11 sequences; in another embodiment, multiplex PCR is employed, using two or more pairs of primers to amplify more than one exon at a time.

The product of amplification was then used as a template for the RNA polymerase, with fluoresceinated UTP present to label the RNA product. After sufficient RNA was made, it was fragmented and applied to an exon 10 DNA chip for 15 minutes, after which the chip was washed with hybridization buffer and scanned with the fluorescence microscope. A useful positive control included on many CF exon 10 chips is the 8-mer 3'-CGCCGCCG-5'. FIG. 7, in panels A and B, shows an image made from a region of a DNA chip containing CFTR exon 10 probes; in panel A, the chip was hybridized to nucleic acid derived from the genomic DNA of an individual with wild-type ΔF508 sequences; in panel B, the target nucleic acid originated from a heterozygous (with respect to the ΔF508 mutation) individual. FIG. 8, in sheets 1 and 2, corresponding to panels A and B of FIG. 7, shows graphs of fluorescence intensity versus tiling position.

These figures show that the sequence of the wild-type RNA can be called for most of the bases near the mutation. In the case of the ΔF508 heterozygous carrier, one particular probe, the same one that distinguished so clearly between the wild-type and mutant oligonucleotide targets in the model system described above, in the T-lane binds a large amount of RNA, while the same probe binds little RNA from the wild-type individual. These results show that the DNA chips of the invention are capable of detecting the ΔF508 mutation in a heterozygous carrier.

Thus, the present invention provides methods for synthesizing large numbers of oligonucleotide probes on a glass substrate and unique probe sets in a defined array in which the probes are arranged in the array by the "tiling" method of the invention. The DNA chips produced by the method can be used to detect mutations in particular sequences of a target nucleic acid, such as genomic DNA or RNA produced from transcription of an amplified genomic DNA. These chips can be used to detect both point mutations and small deletions. Moreover, the pattern of hybridization to the chip allows inferences to be drawn about the sequences of the mutant DNAs.

For example, in the model system involving the cystic fibrosis point mutation G480C, the A-lane probe whose position of substitution corresponds to the position of the mutation does not bind much wild-type target, because in the wild-type sequence, a G occupies that position. However, it binds mutant target very well, allowing one to infer correctly that the mutation involves a change of that G to a T. Similarly, in the case of the three-base deletion in cystic fibrosis known as ΔF508, the T-lane probe that binds mutant target so intensely is responding to the fact that the deletion has brought a CAT sequence into the position occupied by a CTT sequence in the wild-type target. The DNA chips of the invention can be used to detect and sequence not only known mutations in an organism's genome but also new mutations not previously characterized. The DNA chips and methods of the invention can also be used to detect specific sequences in other CFTR exons as well as other human genes for purposes of research and clinical genetic analysis, as demonstrated below.

Detection of Specific Human Mitochondrial DNA Sequences with DNA Chips

As noted above, the present invention provides DNA chips on which a known DNA sequence is represented as an array of overlapping oligonucleotides on a solid support. This set of oligonucleotides is used to probe a target nucleic acid comprising the known sequence, allowing mutations to be detected. As also noted above, there are advantages in some applications to using a minimal set of oligonucleotides specific to the sequence of interest, rather than a set of all possible N-mers. Some of these advantages include: (i) each position in the array is highly informative, whether or not hybridization occurs; (ii) nonspecific hybridization is minimized; (iii) it is straightforward to correlate hybridization differences with sequence differences, particularly with reference to the hybridization pattern of a known standard; and (iv) the ability to address each probe independently during synthesis, using high resolution photolithography, allows the array to be designed and optimized for any sequence. For example the length of any probe can be varied independently of the others.

The present invention illustrates these advantages by providing DNA chips and analytical methods for detecting specific sequences of human mitochondrial DNA. In one preferred embodiment, the invention provides a DNA chip for analyzing sequences contained in a 1.3 kb fragment of human mitochondrial DNA from the "D-loop" region, the most polymorphic region of human mitochondrial DNA. One such chip comprises a set of 269 overlapping oligonucleotide probes of varying length in the range of 9→14 nucleotides with varying overlaps arranged in ~600×600 micron features or synthesis sites in an array 1 cm×1 cm in size. The probes on the chip are shown in columnar form below. An illustrative mitochondrial DNA chip of the invention comprises the following probes (X, Y coordinates are shown, followed by the sequence; "DL3" represents the 3'-end of the probe, which is covalently attached to the chip surface.)

| X | Y | Probe | SEQ ID | X | Y | Probe | SEQ ID |
|---|---|---|---|---|---|---|---|
| 0 | 0 | DL3AGTGGGGTATTT | (SEQ ID. NO:26) | 9 | 2 | DL3GGTAGGATGGGT | (SEQ ID. NO:67) |
| 1 | 0 | DL3GGGTATTTAGTT | (SEQ ID. NO:27) | 10 | 2 | DL3GGATGGGTCGTG | (SEQ ID. NO:68) |
| 2 | 0 | DL3TTAGTTTATCCAA | (SEQ ID. NO:28) | 11 | 2 | DL3GGTCGTGTGTGT | (SEQ ID. NO:69) |
| 3 | 0 | DL3ATCCAAACCAGG | (SEQ ID. NO:29) | 12 | 2 | DL3GTGTGTGTGGCG | (SEQ ID. NO:70) |
| 4 | 0 | DL3ACCAGGATCGGA | (SEQ ID. NO:30) | 13 | 2 | DL3TGTGGCGACGAT | (SEQ ID. NO:71) |
| 5 | 0 | DL3CGTGTGTGTGTGG | (SEQ ID. NO:31) | 14 | 2 | DL3GACGATTGGGGT | (SEQ ID. NO:72) |
| 6 | 0 | DL3CGTGTGTGTGTGGC | (SEQ ID. NO:32) | 15 | 2 | DL3ATTGGGGTATGG | (SEQ ID. NO:73) |
| 7 | 0 | DL3TCGTGTGTGTGTGG | (SEQ ID. NO:33) | 16 | 2 | DL3GTATGGGGCTTG | (SEQ ID. NO:74) |
| 8 | 0 | DL3GTAGGATGGGTC | (SEQ ID. NO:34) | 0 | 3 | DL3GGATTGTGGTCG | (SEQ ID. NO:75) |
| 9 | 0 | DL3AGGATGGGTCGT | (SEQ ID. NO:35) | 1 | 3 | DL3TGGTCGGATTGG | (SEQ ID. NO:76) |
| 10 | 0 | DL3GATGGGTCGTGT | (SEQ ID. NO:36) | 2 | 3 | DL3GGATTGGTCTAAA | (SEQ ID. NO:77) |
| 11 | 0 | DL3TGGCGACGATTG | (SEQ ID. NO:37) | 3 | 3 | DL3TCTAAAGTTTAAA | (SEQ ID. NO:78) |
| 12 | 0 | DL3GCGACGATTGGG | (SEQ ID. NO:38) | 4 | 3 | DL3GTTTAAAATAGAA | (SEQ ID. NO:79) |
| 13 | 0 | DL3TGGGGGGGA | | 5 | 3 | DL3ATAGAAAAACCG | (SEQ ID. NO:80) |
| 14 | 0 | DL3GAGGGGGCG | | 6 | 3 | DL3AGAAAAACCGC | (SEQ ID. NO:81) |
| 15 | 0 | DL3GGAGGGGGCGA | (SEQ ID. NO:39) | 7 | 3 | DL3AACCGCCATAC | (SEQ ID. NO:82) |
| 16 | 0 | DL3GAGGGGGCGA | (SEQ ID. NO:40) | 8 | 3 | DL3CCATACGTGAAAA | (SEQ ID. NO:83) |
| 0 | 1 | DL3GGCTTGGTTGG | (SEQ ID. NO:41) | 9 | 3 | DL3ACGTGAAAATTGT | (SEQ ID. NO:84) |
| 1 | 1 | DL3GGTTGGTTTGGG | (SEQ ID. NO:42) | 10 | 3 | DL3AATTGTCAGTGGG | (SEQ ID. NO:85) |
| 2 | 1 | DL3TGGGGTTTCTAG | (SEQ ID. NO:43) | 11 | 3 | DL3TGTCAGTGGGGG | (SEQ ID. NO:86) |
| 3 | 1 | DL3GTTTCTAGTGGG | (SEQ ID. NO:44) | 12 | 3 | DL3TGGGGTTGA | (SEQ ID. NO:87) |
| 4 | 1 | DL3AGTGGGGGGTGT | (SEQ ID. NO:45) | 13 | 3 | DL3GGGTTGATTGTGT | (SEQ ID. NO:88) |
| 5 | 1 | DL3GGGGTGTCAAAT | (SEQ ID. NO:46) | 14 | 3 | DL3TTGTGTAATAAAA | (SEQ ID. NO:89) |
| 6 | 1 | DL3GTCAAATACATCG | (SEQ ID. NO:47) | 15 | 3 | DL3AATAAAAGGGGA | (SEQ ID. NO:90) |
| 7 | 1 | DL3ACATCGAATGGAG | (SEQ ID. NO:48) | 16 | 3 | DL3TAAAAGGGGAGG | (SEQ ID. NO:91) |
| 8 | 1 | DL3CGAATGGAGGAG | (SEQ ID. NO:49) | 0 | 4 | DL3GTTTTTTAAAGG | (SEQ ID. NO:92) |
| 9 | 1 | DL3GAGGAGTTTCGT | (SEQ ID. NO:50) | 1 | 4 | DL3TTTTAAAGGTGG | (SEQ ID. NO:93) |
| 10 | 1 | DL3TTTCGTTATGTGA | (SEQ ID. NO:51) | 2 | 4 | DL3AGGTGGTTTGG | (SEQ ID. NO:94) |
| 11 | 1 | DL3ATGTGACTTTTAC | (SEQ ID. NO:52) | 3 | 4 | DL3TTGGGGGGGAG | (SEQ ID. NO:95) |
| 12 | 1 | DL3GACTTTTACAAAT | (SEQ ID. NO:53) | 4 | 4 | DL3GGAGGGGGCG | (SEQ ID. NO:96) |
| 13 | 1 | DL3AAATCTGCCCGA | (SEQ ID. NO:54) | 5 | 4 | DL3GGGGCGAAGAC | (SEQ ID. NO:97) |
| 14 | 1 | DL3AATCTGCCCGAG | (SEQ ID. NO:55) | 6 | 4 | DL3GAAGACCGGATG | (SEQ ID. NO:98) |
| 15 | 1 | DL3CCCGAGTGTAGT | (SEQ ID. NO:56) | 7 | 4 | DL3CCGGATGTCGTG | (SEQ ID. NO:99) |
| 16 | 1 | DL3AGTGTAGTGGGG | (SEQ ID. NO:57) | 8 | 4 | DL3GTCGTGAATTTGT | (SEQ ID. NO:100) |
| 0 | 2 | DL3GGGAGGGTGAG | (SEQ ID. NO:58) | 9 | 4 | DL3CGTGAATTTGTGT | (SEQ ID. NO:101) |
| 1 | 2 | DL3GGTGAGGGTATG | (SEQ ID. NO:59) | 10 | 4 | DL3TTGTGTAGAGACG | (SEQ ID. NO:102) |
| 2 | 2 | DL3GGTATGATGATTAG | (SEQ ID. NO:60) | 11 | 4 | DL3TAGAGACGGTTT | (SEQ ID. NO:103) |
| 3 | 2 | DL3GATTAGAGTAAGT | (SEQ ID. NO:61) | 12 | 4 | DL3ACGGTTTGGGG | (SEQ ID. NO:104) |
| 4 | 2 | DL3TTAGAGTAAGTTA | (SEQ ID. NO:62) | 13 | 4 | DL3TGGGGTTTTTGT | (SEQ ID. NO:105) |
| | | | | 14 | 4 | DL3GGGTTTTTGTTT | (SEQ ID. NO:106) |

-continued

| | | | | | | | |
|---|---|---|---|---|---|---|---|
| 5 | 2 | DL3AAGTTATGTTGGG | (SEQ ID. NO:63) | 15 | 4 | DL3TTGTTTCTTGGG | (SEQ ID. NO:107) |
| 6 | 2 | DL3GTTGGGGGCG | (SEQ ID. NO:64) | 16 | 4 | DL3TCTTGGGATTGTG | (SEQ ID. NO:108) |
| 7 | 2 | DL3GGGGGGGGTA | (SEQ ID. NO:65) | 0 | 5 | DL3TGTATGAATGATTT | (SEQ ID. NO:109) |
| 8 | 2 | DL3GCGGGTAGGAT | (SEQ ID. NO:66) | 1 | 5 | DL3TGATTTCACACAA | (SEQ ID. NO:110) |
| 2 | 5 | DL3ACACAATTAATTAA | (SEQ ID. NO:111) | 14 | 7 | DL3CTCTGCGACCTC | (SEQ ID. NO:157) |
| 3 | 5 | DL3AATTAATTACGAA | (SEQ ID. NO:112) | 15 | 7 | DL3GACCTCGGCCT | (SEQ ID. NO:158) |
| 4 | 5 | DL3TACGAACATCCTG | (SEQ ID. NO:113) | 16 | 7 | DL3TCGGCCTCGTG | (SEQ ID. NO:159) |
| 5 | 5 | DL3ACGAACATCCTGT | (SEQ ID. NO:114) | 0 | 8 | DL3GATGAAGTCCCAG | (SEQ ID. NO:160) |
| 6 | 5 | DL3TCCTGTATTATTA | (SEQ ID. NO:115) | 1 | 8 | DL3AGTCCCAGTATTT | (SEQ ID. NO:161) |
| 7 | 5 | DL3GTATTATTATTGTT | (SEQ ID. NO:116) | 2 | 8 | DL3GTATTTCGGATTT | (SEQ ID. NO:162) |
| 8 | 5 | DL3ATTGTTAAACTTA | (SEQ ID. NO:117) | 3 | 8 | DL3TCGGATTTATCG | (SEQ ID. NO:163) |
| 9 | 5 | DL3AAACTTACAGACG | (SEQ ID. NO:118) | 4 | 8 | DL3GATTTATCGGGT | (SEQ ID. NO:164) |
| 10 | 5 | DL3ACAGACGTGTCG | (SEQ ID. NO:119) | 5 | 8 | DL3ATCGGGTGTGCA | (SEQ ID. NO:165) |
| 11 | 5 | DL3GTGTCGGTGAAA | (SEQ ID. NO:120) | 6 | 8 | DL3TGTGCAAGGGGA | (SEQ ID. NO:166) |
| 12 | 5 | DL3GTGAAAGGTGTGT | (SEQ ID. NO:121) | 7 | 8 | DL3CAAGGGGAATTT | (SEQ ID. NO:167) |
| 13 | 5 | DL3GGTGTGTCTGTAG | (SEQ ID. NO:122) | 8 | 8 | DL3GAATTTATTCTGTA | (SEQ ID. NO:168) |
| 14 | 5 | DL3TGTGTCTGTAGTA | (SEQ ID. NO:123) | 9 | 8 | DL3TCTGTAGTGCTAC | (SEQ ID. NO:169) |
| 15 | 5 | DL3GTAGTATTGTTTT | (SEQ ID. NO:124) | 10 | 8 | DL3GTAGTGCTACCT | (SEQ ID. NO:170) |
| 16 | 5 | DL3AGTATTGTTTTTT | (SEQ ID. NO:125) | 11 | 8 | DL3GCTACCTAGTAG | (SEQ ID. NO:171) |
| 0 | 6 | DL3CCTCGTGGGATA | (SEQ ID. NO:126) | 12 | 8 | DL3CTAGTAGTCCAGA | (SEQ ID. NO:172) |
| 1 | 6 | DL3TGGGATACAGCG | (SEQ ID. NO:127) | 13 | 8 | DL3TCCAGATA9TGGG | (SEQ ID. NO:173) |
| 2 | 6 | DL3GATACAGCGTCAT | (SEQ ID. NO:128) | 14 | 8 | DL3AGATAGTGGGATA | (SEQ ID. NO:174) |
| 3 | 6 | DL3GCGTCATAGACAG | (SEQ ID. NO:129) | 15 | 8 | DL3GGGATAATTGGT | (SEQ ID. NO:175) |
| 4 | 6 | DL3AGACAGAAACTAA | (SEQ ID. NO:130) | 16 | 8 | DL3TAATTGGTGAGTG | (SEQ ID. NO:176) |
| 5 | 6 | DL3CAGAAACTAAGGA | (SEQ ID. NO:131) | 0 | 9 | DL3TATAGGGCGTGT | (SEQ ID. NO:177) |
| 6 | 6 | DL3TAAGGACGGAGT | (SEQ ID. NO:132) | 1 | 9 | DL3GGGCGTGTTCTCA | (SEQ ID. NO:178) |
| 7 | 6 | DL3GACGGAGTAGGA | (SEQ ID. NO:133) | 2 | 9 | DL3GTGTTCTCACGAT | (SEQ ID. NO:179) |
| 8 | 6 | DL3GTAGGATAATAAA | (SEQ ID. NO:134) | 3 | 9 | DL3TCACGATGAGAGG | (SEQ ID. NO:180) |
| 9 | 6 | DL3TAATAAATAGCG | (SEQ ID. NO:135) | 4 | 9 | DL3ATGAGAGGAGCG | (SEQ ID. NO:181) |
| 10 | 6 | DL3ATAGCGTAGGAT | (SEQ ID. NO:136) | 5 | 9 | DL3AGGAGCGAGGC | (SEQ ID. NO:182) |
| 11 | 6 | DL3TAGCGTAGGATG | (SEQ ID. NO:137) | 6 | 9 | DL3CGAGGCCCGG | (SEQ ID. NO:183) |
| 12 | 6 | DL3AGGATGCAAGTT | (SEQ ID. NO:138) | 7 | 9 | DL3GCCCGGGTATT | (SEQ ID. NO:184) |
| 13 | 6 | DL3ATGCAAGTTATAA | (SEQ ID. NO:139) | 8 | 9 | DL3CGGGTATTGTGA | (SEQ ID. NO:185) |
| 14 | 6 | DL3GTTATAATGTCCG | (SEQ ID. NO:140) | 9 | 9 | DL3GTGAACCCCAT | (SEQ ID. NO:186) |
| 15 | 6 | DL3ATGTCCGCTTGT | (SEQ ID. NO:141) | 10 | 9 | DL3CCCCATCGATTT | (SEQ ID. NO:187) |
| 16 | 6 | DL3TCCGCTTGTATG | (SEQ ID. NO:142) | 11 | 9 | DL3ATCGATTTCACTT | (SEQ ID. NO:188) |
| 0 | 7 | DL3GTGAGTGCCCTC | (SEQ ID. NO:143) | 12 | 9 | DL3TTTCACTTGACAT | (SEQ ID. NO:189) |
| 1 | 7 | DL3TGCCCTCGAGAG | (SEQ ID. NO:144) | 13 | 9 | DL3TTGACATAGAGCT | (SEQ ID. NO:190) |
| 2 | 7 | DL3CCTCGAGAGGTA | (SEQ ID. NO:145) | 14 | 9 | DL3TAGAGCTGTAGAC | (SEQ ID. NO:191) |
| 3 | 7 | DL3AGAGGTACGTAA | (SEQ ID. NO:146) | 15 | 9 | DL3GTAGACCAAGGA | (SEQ ID. NO:192) |
| 4 | 7 | DL3ACGTAAACCATA | (SEQ ID. NO:147) | 16 | 9 | DL3ACCAAGGATGAAG | (SEQ ID. NO:193) |
| 5 | 7 | DL3ACCATAAAAGCAG | (SEQ ID. NO:148) | 0 | 10 | DL3CGTGTAATGTCAG | (SEQ ID. NO:194) |
| 6 | 7 | DL3AAAGCAGACCC | (SEQ ID. NO:149) | 1 | 10 | DL3TGTCAGTTTAGGG | (SEQ ID. NO:195) |
| 7 | 7 | DL3AGACCCCCCAT | (SEQ ID. NO:150) | 2 | 10 | DL3TCAGTTTAGGGA | (SEQ ID. NO:196) |
| 8 | 7 | DL3CCCCCATACGT | (SEQ ID. NO:151) | 3 | 10 | DL3TAGGGAAGAGCA | (SEQ ID. NO:197) |
| 9 | 7 | DL3CATACGTGCGCT | (SEQ ID. NO:152) | 4 | 10 | DL3AAGAGCAGGGGT | (SEQ ID. NO:198) |
| 10 | 7 | DL3GTGCGCTATCAG | (SEQ ID. NO:153) | 5 | 10 | DL3CAGGGGTACCTA | (SEQ ID. NO:199) |
| 11 | 7 | DL3GCGCTATCAGTA | (SEQ ID. NO:154) | 6 | 10 | DL3GGTACCTACTGG | (SEQ ID. NO:200) |
| 12 | 7 | DL3TCAGTAACGCTC | (SEQ ID. NO:155) | 7 | 10 | DL3TACTGGGGGGA | (SEQ ID. NO:201) |
| 13 | 7 | DL3GTAACGCTCTGC | (SEQ ID. NO:156) | 8 | 10 | DL3GGGGGAGTCTAT | (SEQ ID. NO:202) |
| 9 | 10 | DL3AGTCTATCCCCA | (SEQ ID. NO:203) | 11 | 13 | DL3CATGTATTTTTGG | (SEQ ID. NO:246) |
| 10 | 10 | DL3ATCCCCAGGGA | (SEQ ID. NO:204) | 12 | 13 | DL3TTTTGGGTTAGG | (SEQ ID. NO:247) |
| 11 | 10 | DL3CAGGGAACTGGT | (SEQ ID. NO:205) | 13 | 13 | DL3GGGGTTAGGATGT | (SEQ ID. NO:248) |
| 12 | 10 | DL3ACTGGTGGTAGG | (SEQ ID. NO:206) | 14 | 13 | DL3GGATGTAGTTTTG | (SEQ ID. NO:249) |
| 13 | 10 | DL3CTGGTGGTAGGA | (SEQ ID. NO:207) | 15 | 13 | DL3TGTAGTTTTGGG | (SEQ ID. NO:250) |
| 14 | 10 | DL3GTAGGAGGCACA | (SEQ ID. NO:208) | 16 | 13 | DL3TTTGGGGGAGG | (SEQ ID. NO:251) |
| 15 | 10 | DL3GGCACATTTAGT | (SEQ ID. NO:209) | 5 | 14 | DL3GGGTTCATAACTG | (SEQ ID. NO:252) |
| 16 | 10 | DL3TTTAGTTATAGGG | (SEQ ID. NO:210) | 6 | 14 | DL3ATAACTGAGTGGG | (SEQ ID. NO:253) |
| 0 | 11 | DL3AGGTTTACGGTG | (SEQ ID. NO:211) | 7 | 14 | DL3AACTGAGTGGGT | (SEQ ID. NO:254) |
| 1 | 11 | DL3TACGGTGGGGA | (SEQ ID. NO:212) | 8 | 14 | DL3GTGGGTAGTTGT | (SEQ ID. NO:255) |
| 2 | 11 | DL3GTGGGGAGTGG | (SEQ ID. NO:213) | 9 | 14 | DL3GTAGTTGTTGGC | (SEQ ID. NO:256) |
| 3 | 11 | DL3GGGGAGTGGGTGA | (SEQ ID. NO:214) | 10 | 14 | DL3GTTGGCGATACA | (SEQ ID. NO:257) |
| 4 | 11 | DL3GGGTGATCCTATG | (SEQ ID. NO:215) | 11 | 14 | DL3CGATACATAAAAG | (SEQ ID. NO:258) |
| 5 | 11 | DL3CCTATGGTTGTTT | (SEQ ID. NO:216) | 12 | 14 | DL3TAAAAGCATGTAA | (SEQ ID. NO:259) |
| 6 | 11 | DL3GGTTGTTTGGATG | (SEQ ID. NO:217) | 13 | 14 | DL3GCATGTAATGACG | (SEQ ID. NO:260) |
| 7 | 11 | DL3GTTTGGATGGGT | (SEQ ID. NO:218) | 14 | 14 | DL3ATGACGCCTCGGT | (SEQ ID. NO:261) |
| 8 | 11 | DL3ATGGGTGGGAAT | (SEQ ID. NO:219) | 15 | 14 | DL3GTCGGTGGTACT | (SEQ ID. NO:262) |
| 9 | 11 | DL3GGGAATTGTCATG | (SEQ ID. NO:220) | 16 | 14 | DL3GGTACTTATAACA | (SEQ ID. NO:263) |
| 10 | 11 | DL3GTCATGTATCATGT | (SEQ ID. NO:221) | 5 | 15 | DL3TCGATTCTAAGAT | (SEQ ID. NO:264) |
| 11 | 11 | DL3TCATGTATTTCGG | (SEQ ID. NO:222) | 6 | 15 | DL3TAAGATTAAATTT | (SEQ ID. NO:265) |
| 12 | 11 | DL3TATTTCGGTAAA | (SEQ ID. NO:223) | 7 | 15 | DL3AAATTTGAATAAG | (SEQ ID. NO:266) |
| 13 | 11 | DL3TTCGGTAAATGG | (SEQ ID. NO:224) | 8 | 15 | DL3AATAAGAGACAAG | (SEQ ID. NO:267) |
| 14 | 11 | DL3GTAAATGGCATGT | (SEQ ID. NO:225) | 9 | 15 | DL3AAGAGACAAGAAA | (SEQ ID. NO:268) |
| 15 | 11 | DL3GCATGTAAAGTCGTG | (SEQ ID. NO:226) | 10 | 15 | DL3AAGAAAGTACCC | (SEQ ID. NO:269) |
| 16 | 11 | DL3GTAATCGTGTAAT | (SEQ ID. NO:227) | 11 | 15 | DL3AAAGTACCCCTT | (SEQ ID. NO:270) |
| 5 | 12 | DL3GGGAGGGGTAC | (SEQ ID. NO:228) | 12 | 15 | DL3CCCCTTCGTCTA | (SEQ ID. NO:271) |
| 6 | 12 | DL3GGGTACGAATGT | (SEQ ID. NO:229) | 13 | 15 | DL3CTTCGTCTAAAC | (SEQ ID. NO:272) |
| 7 | 12 | DL3ACGAATGTTCGTT | (SEQ ID. NO:230) | 14 | 15 | DL3CTAAACCCATGG | (SEQ ID. NO:273) |
| 8 | 12 | DL3TGTTCGTTCATGT | (SEQ ID. NO:231) | 15 | 15 | DL3AACCCATGGTGG | (SEQ ID. NO:274) |
| 9 | 12 | DL3CGTTCATGTCGTT | (SEQ ID. NO:232) | 16 | 15 | DL3TGGTGGGTTCAT | (SEQ ID. NO:275) |

-continued

| | | | | | | | |
|---|---|---|---|---|---|---|---|
| 10 | 12 | DL3GTCGTTAGTTGG | (SEQ ID. NO:233) | 5 | 16 | DL3TTGGAAAAAGGT | (SEQ ID. NO:276) |
| 11 | 12 | DL3TAGTTGGGAGTT | (SEQ ID. NO:234) | 6 | 16 | DL3AAAAGGTTCCTG | (SEQ ID. NO:277) |
| 12 | 12 | DL3GGAGTTGATAGTG | (SEQ ID. NO:235) | 7 | 16 | DL3GGTTCCTGTTTA | (SEQ ID. NO:278) |
| 13 | 12 | DL3ATAGTGTGTAGTT | (SEQ ID. NO:236) | 8 | 16 | DL3CCTGTTTAGTCTC | (SEQ ID. NO:279) |
| 14 | 12 | DL3GTFTAGTTGACGT | (SEQ ID. NO:237) | 9 | 16 | DL3TTAGTCTCTTTTT | (SEQ ID. NO:280) |
| 15 | 12 | DL3TGACGTTGAGGT | (SEQ ID. NO:238) | 10 | 16 | DL3CTTTTTCAGAAAT | (SEQ ID. NO:281) |
| 16 | 12 | DL3CGTTGAGGTTTA | (SEQ ID. NO:239) | 11 | 16 | DL3AGAAAATTGAGGTG | (SEQ ID. NO:282) |
| 5 | 13 | DL3TATAACATGCCAT | (SEQ ID. NO:240) | 12 | 16 | DL3AAAATTGAGGTGGT | (SEQ ID. NO:283) |
| 6 | 13 | DL3AACATGCCATGGT | (SEQ ID. NO:241) | 13 | 16 | DL3GGTGGTAATCGT | (SEQ ID. NO:284) |
| 7 | 13 | DL3CCATGGTATTAT | (SEQ ID. NO:242) | 14 | 16 | DL3TAATCGTGGGTT | (SEQ ID. NO:285) |
| 8 | 13 | DL3ATTTATGAACTGG | (SEQ ID. NO:243) | 15 | 16 | DL3GTGGGTTTCGAT | (SEQ ID. NO:286) |
| 9 | 13 | DL3AACTGGTGGACAT | (SEQ ID. NO:244) | 16 | 16 | DL3GGTTTCGATTCT | (SEQ ID. NO:287) |
| 10 | 13 | DL3TGGACATCATGTA | (SEQ ID. NO:245) | | | | |

No probes were present in positions X, Y=0, 12 to X, Y=4, 12; X, Y=0, 13 to X, Y=4, 13; X, Y=0, 14 to X, Y=4, 14; X, Y=0, 15 to X, Y=4, 15; X, Y=0, 16 to X, Y=4, 16; The length of each of the probes on the chip was variable to minimize differences in melting temperature and potential for cross-hybridization. Each position in the sequence is represented by at least one probe and most positions are represented by 2 or more probes. As noted above, the amount of overlap between the oligonucleotides varies from probe to probe. FIG. 9 shows the human mitochondrial genome; "$O_H$" is the H strand origin of replication, and arrows indicate the cloned unshaded sequence.

DNA was prepared from hair roots of six human donors (mt1 to mt6) and then amplified by PCR and cloned into M13; the resulting clones were sequenced using chain terminators to verify that the desired specific sequences were present. DNA from the sequenced M13 clones was amplified by PCR, transcribed in vitro, and labeled with fluorescein-UTP using T3 RNA polymerase. The 1.3 kb RNA transcripts were fragmented and hybridized to the chip. The results showed that each different individual had DNA that produced a unique hybridization fingerprint on the chip and that the differences in the observed patterns could be correlated with differences in the cloned genomic DNA sequence. The results also demonstrated that very long sequences of a target nucleic acid can be represented comprehensively as a specific set of overlapping oligonucleotides and that arrays of such probe sets can be usefully applied to genetic analysis.

The sample nucleic acid was hybridized to the chip in a solution composed of 6×SSPE, 0.1% Triton-X 100 for 60 minutes at 15° C. The chip was then scanned by confocal scanning fluorescence microscopy. The individual features on the chip were 588×588 microns, but the lower left 5×5 square features in the array did not contain probes. To quantitate the data, pixel counts were measured within each synthesis site. Pixels represent 50×50 microns. The fluorescence intensity for each feature was scaled to a mean determined from 27 bright features. After scanning, the chip was stripped and rehybridized; all six samples were hybridized to the same chip. FIG. 10 shows the image observed from the mt4 sample on the DNA chip. FIG. 11 shows the image observed from the mt5 sample on the DNA chip. FIG. 12 shows the predicted difference image between the mt4 and mt5 samples on the DNA chip based on mismatches between the two samples and the reference sequence (see Anderson et al., 1981, Nature 290: 457–465, incorporated herein by reference). FIG. 13 shows the actual difference image observed.

The results show that, in almost all cases, mismatched probe/target hybrids resulted in lower fluorescence intensity than perfectly matched hybrids. Nonetheless, some probes detected mutations (or specific sequences) better than others, and in several cases, the differences were within noise levels. Improvements can be realized by increasing the amount of overlap between probes and hence overall probe density and, for duplex DNA targets, using a second set of probes, either on the same or a separate chip, corresponding to the second strand of the target. FIG. 14, in sheets 1 and 2, shows a plot of normalized intensities across rows 10 and 11 of the array and a tabulation of the mutations detected.

FIG. 15 shows the discrimination between wild-type and mutant hybrids obtained with this chip. The median of the six normalized hybridization scores for each probe was taken. The graph plots the ratio of the median score to the normalized hybridization score versus mean counts. On this graph, a ratio of 1.6 and mean counts above 50 yield no false positives, and while it is clear that detection of some mutants can be improved, excellent discrimination is achieved, considering the small size of the array. FIG. 16 illustrates how the identity of the base mismatch may influence the ability to discriminate mutant and wild-type sequences more than the position of the mismatch within an oligonucleotide probe. The mismatch position is expressed as % of probe length from the 3'-end. The base change is indicated on the graph. These results show that the DNA chip increases the capacity of the standard reverse dot blot format by orders of magnitude, extending the power of that approach many fold and that the methods of the invention are more efficient and easier to automate than gel-based methods of nucleic acid sequence and mutation analysis.

These advantages become more apparent as chips with more and more probes are employed. To illustrate, the present invention provides a DNA chip for analyzing human mitochondrial DNA (mtDNA) that "tiles" through 648 nucleotides of human H strand mtDNA from positions 16280 to 356. The probes in the array are 15 nucleotides in length, and each position in the target sequence is represented by a set of 4 probes (A, C, G, T substitutions), which differed from one another at position 7 from the 3'-end. The array consists of 13 blocks of 4×50 probes: each block scans through 50 nucleotides of contiguous mtDNA sequence. The blocks are separated by blank rows. The 4 corner columns contain control probes; there are a total of 2600 probes in a 1.28 cm×1.28 cm square area (feature), and each area is 256×197 microns.

Labeled RNA target DNA was prepared by PCR amplification of a 1.3 kb region of human mtDNA spanning positions 15935 to 667, cloning into M13 (sequence verification was performed), and reamplification of the cloned sequences using primers tagged with T3 and T7 RNA polymerase promoter sequences and in vitro transcription to produce fluorescein-UTP labeled RNA. The RNA was fragmented and hybridized to the oligonucleotide array in a solution composed of 6×SSPE, 0.1% Triton X-100 for 60 minutes at 18° C. Unhybridized material was washed away with buffer, and the chip was scanned at 25 micron pixel resolution.

FIG. 17 provides a 5' to 3' sequence listing of one target corresponding to the probes on the chip. X is a control probe. Positions that differ in the target (i.e., are mismatched with the probe at the designated site) are in bold. FIG. 18 shows the fluorescence image produced by scanning the chip when hybridized to this sample. About 95% of the sequence could be read correctly from only one strand of the original duplex target nucleic acid. Although some probes did not provide excellent discrimination and some probes did not appear to hybridize to the target efficiently, excellent results were achieved. The target sequence differed from the probe set at six positions: 4 transitions and 2 insertions. All 4 transitions were detected, and specific probes could readily be incorporated into the array to detect insertions or deletions. FIG. 19 illustrates the detection of 4 transitions in the target sequence relative to the wild-type probes on the chip.

These results illustrate that longer sequences can be read using the DNA chips and methods of the invention, as compared to conventional sequencing methods, where reading length is limited by the resolution of gel electrophoresis. Similar results were observed when genomic DNA samples were prepared from human hair roots. Hybridization and signal detection require less than an hour and can be readily shortened by appropriate choice of buffers, temperatures, probes, and reagents. In principle, longer sequence reads can be obtained than by conventional sequencing, where reading length is limited by the resolution of gel electrophoresis.

P53 Sequencing and Diagnostic DNA Chips

P53 is a tumor suppressor gene that has been found to be mutated in most forms of cancer (see Levine et al, 1991, *Nature* 351: 453–456, and Hollstein et al., 1991, *Science* 253: 49–53, each of which is incorporated herein by reference). In addition, there is a hereditary syndrome, Li-Fraumeni, in which individuals inherit mutant alleles of p53 and tend to have cancer at relatively young ages (Frebourg et al., 1992, *PNAS* 89: 6413–6417, incorporated herein by reference). During the development of a cancer, p53 is inactivated. The course of p53 inactivation generally involves a mutation in one copy of p53 and is often followed by deletion of the other copy. After p53 is inactivated, chromosomal abnormalities begin to appear in tumors. In the best understood form of cancer, colorectal cancer, well over 50%, perhaps 80%, of all patients with tumors have p53 mutations. In addition, p53 mutations have been found in a high proportion of lung, breast, and other tumors (Rodrigues et al., 1990, *PNAS* 87: 7555–7559, incorporated herein by reference). According to data presented by David Sidransky (1992 San Diego Conference), over 400 mutations in p53 are known.

The p53 gene spans 20 kbp in humans and has 11 exons, 10 of which are protein coding (see Tominaga et al., 1992, *Critical Reviews in Oncogenesis* 3: 257–282, incorporated herein by reference). The gene produces a 53 kilodalton phosphoprotein that regulates DNA replication. The protein acts to halt replication at the G1/S boundary in the cell cycle and is believed to act as a "molecular policeman," shutting down replication when the DNA is damaged or blocking the reproduction of DNA viruses (see Lane, 1992, *Nature* 358: 15–16, incorporated herein by reference). There is substantial interest in the cancer research community in analyzing p53 mutations. The NCI is currently funding contracts to characterize the p53 mutation spectra caused by various carcinogens. In addition, there are research projects which involve sequencing p53 from spontaneously arising tumors. A major resource in these studies is the huge supply of biopsy material stored in paraffin blocks. Also, there are projects which are aimed at analyzing the relationship between the particular mutation in p53 and the functioning of the resulting protein. Furthermore, there are projects looking at the germline inheritance of p53 mutations and the development of cancer. The present invention provides useful DNA chips and methods for such studies.

In addition, the present invention also provides a diagnostic test kit and method and p53 probes immobilized on a DNA chip in an organized array. Currently available diagnostic tests for cancer typically have a sensitivity of about 50%. The present invention provides significant advantages over such tests, and in one embodiment provides a method for detecting cancer-causing mutations in p53 that involves the steps of (1) obtaining a biopsy, which is optionally fractionated by cryostat sectioning to enrich tumor cells to about 80% of the total cell population. The DNA or RNA is then extracted, amplified, and analyzed with a DNA chip for the presence of p53 mutations correlated with malignancy.

To illustrate the value of the DNA chips of the present invention in such a method, a DNA chip was synthesized by the VLSIPS™ method to provide an array of overlapping probes which represent or tile across a 60 base region of exon 6 of the p53 gene. To demonstrate the ability to detect substitution mutations in the target, twelve different single substitution mutations (wild type and three different substitutions at each of three positions) were represented on the chip along with the wild type. Each of these mutations was represented by a series of twelve 12-mer oligonucleotide probes, which were complementary to the wild type target except at the one substituted base. Each of the twelve probes was complementary to a different region of the target and contained the mutated base at a different position, e.g., if the substitution was at base 32, the set of probes would be complementary–with the exception of base 32—to regions of the target 21–32, 22–33, and 32–43). This enabled investigation of the effect of the substitution position within the probe. The alignment of some of the probes with a 12-mer model target nucleic acid is shown in FIG. 20.

To demonstrate the effect of probe length, an additional series of ten 10-mer probes was included for each mutation (see FIG. 21). In the vicinity of the substituted positions, the wild-type sequence was represented by every possible overlapping 12-mer and 10-mer probe. To simplify comparisons, the probes corresponding to each varied position were arranged on the chip in the rectangular regions with the following structure: each row of cells represents one substitution, with the top row representing the wild type. Each column contains probes complementary to the same region of the target, with probes complementary to the 3'-end of the target on the left and probes complementary to the 5'-end of the target on the right. The difference between two adjacent columns is a single base shift in the positioning of the probes. Whenever possible, the series of 10-mer probes were placed in four rows immediately underneath and aligned with the 4 rows of 12-mer probes for the same mutation.

To provide model targets, 5' fluoresceinated 12-mers containing all possible substitutions in the first position of codon 192 were synthesized (see the starred position in the target in FIG. 20). Solutions containing 10 nM target DNA in 6×SSPE, 0.25% Triton X-100 were hybridized to the chip at room temperature for several hours. While target nucleic was hybridized to the chip, the fluorophores on the chip were excited by light from an argon laser, and the chip was scanned with an autofocusing confocal microscope. The emitted signals were processed by a PC to produce an image using image analysis software. By 1 to 3 hours, the signal had reached a plateau; to remove the hybridized target and allow hybridization to another target, the chip was stripped with 60% formamide, 2×SSPE at 17° C. for 5 minutes. The washing buffer and temperature can vary, but the buffer typically contains 2-to-3×SSPE, 10-to-60% formamide (one can use multiple washes, increasing the formamide concentration by 10% each wash, and scanning between washes to determine when the wash is complete), and optionally a small percentage of Triton X-100, and the temperature is typically in the range of 15° to 18° C.

Very distinct patterns were observed after hybridization with targets with 1 base substitutions and visualization with a confocal microscope and software analysis, as shown in FIG. 22. In general, the probes which form perfect matches with the target retain the highest signal. For example, in the first image in Figure PC, the 12-mer probes that form perfect matches with the wild-type (WT) target are in the first row (top). The 12-mer probes with single base mismatches are located in the second, third, and fourth rows and have much lower signals. The data is also depicted graphically in FIG. 23. On each graph, the X ordinate is the position of the probe in its row on the chip, and the Y ordinate is the signal at that probe site after hybridization.

When a target with a different one base substitution is hybridized the complementary set of probes has the highest signal (see pictures 2, 3, and 4 in FIG. 22 and graphs 2, 3, and 4 in FIG. 23). In each case, the probe set with no mismatches with the target has the highest signals. Within a 12-mer probe set, the signal was highest at position 6 or 7. The graphs show that the signal difference between 12-mer probes at the same X ordinate tended to be greatest at positions 5 and 8 when the target and the complementary probes formed 10 base pairs and 11 base pairs, respectively. Because tumors often have both WT and mutant p53 genes, mixed target populations were also hybridized to the chip, as shown in FIG. 24. When the hybridization solution consisted of a 1:1 mixture of WT 12-mer and a 12-mer with a substitution in position 7 of the target, the sets of probes that were perfectly matched to both targets showed higher signals than the other probe sets.

The hybridization efficiency of a 10-mer probe array as compared to a 12-mer probe array was also compared. The 10-mer and 12-mer probe arrays gave comparable signals (see graphs 1–4 in FIG. 23 and graphs 1–4 in FIG. 25). However, the 10-mer probe sets, which are in rows 5–8 (see images in FIG. 22), seemed to be better in this model system than the 12-mer probe sets at resolving one target from another, consistent with the expectation that one base mismatches are more destabilizing for 10-mers than 12-mers. Hybridization results within probe sets perfectly matched to target also followed the expectation that, the more matches the individual probe formed with the target, the higher the signal. However, duplexes with two 3' dangles (see FIG. 23, position 6 in graphs 1–4) have about as much signal as the probes which are matched along their entire length (see FIG. 23, position 7, in graphs 1–4).

This illustrative model system shows that 12-mer targets that differ by one base substitutions can be readily distinguished from one another by the novel probe array provided by the invention and that resolution of the different 12-mer targets was somewhat better with the 10-mer probe sets than with the 12-mer probe sets. The value of having several overlapping probes hybridizing to a target demonstrates the value of the multiple hybridization events that take place on a DNA chip of the invention. The results also demonstrate the feasibility of constructing a probe set to sequence the entire 1.4 kbp protein coding region of p53 or alternatively the 0.6 kbp of exons 5–9 containing mutation hot spots.

For sequencing, the p53 DNA can be cloned from the sample or directly amplified from genomic DNA by PCR. If genomic PCR is used, then the DNA can be diluted prior to amplification so that a single copy of the gene is amplified. For diagnostic purposes, the genomic DNA can be isolated from a tumor biopsy in which the tumor cells may be the majority population. As noted above, the proportion of tumor cells in a sample can be enriched by cryostat sectioning. DNA can also be isolated and amplified from tumor samples stored in paraffin blocks.

The p53 DNA in the sample can be amplified by PCR (although other amplification methods can be used) using 3–4 primer pairs generating amplicons of <3 kbp each. Illustrative primers of the invention for amplifying exon 5 of the p53 gene are shown below (B is biotin; F is fluorescein).

5'-B-CACTTGTGCCCTGACTTTCAAC-3'(SEQ. ID NO:288)
5'-F-CACTTGTGCCCTGACTTTCAAC-3'
5'-ATGCAATTAACCCTCACTAAAGGGAGACACTTG-TGCCCTGACTTTCAAC-3'(SEQ. ID NO:289) (has T3 promoter)
5'-B-GACCCTGGGCAACCAGCCCTGTCGT-3'(SEQ. ID NO:290)
5'-F-GACCCTGGGCAACCAGCCCTGTCGT-3'
5'-TAATACGACTCACTATAGGGAGGACCCTGGGCA-ACCAGCCCTGTCGT-3'(SEQ. ID NO:291) (has T3 promoter)

After PCR amplification of the target (the amplified target is called the "amplicon") one strand of the amplicon can then be isolated, i.e., using a biotinylated primer that allows capture of the undesired strand on streptavidin beads. Alternatively, asymmetric PCR can be used to generate a single-stranded target. Another approach involves the generation of single stranded RNA form the PCR product by incorporating a T7 or other RNA polymerase promoter in one of the primers. The single-stranded material can optionally be fragmented to generate smaller nucleic acids with less significant secondary structure than longer nucleic acids.

In one such method, fragmentation is combined with labeling. To illustrate, degenerate 8-mers or other degenerate short oligonucleotides are hybridized to the single-stranded target material. In the next step, a DNA polymerase is added with the four different dideoxynucleotides, each labeled with a different fluorophore. Fluorophore-labeled dideoxynucleotide are available from a variety of commercial suppliers, such as ABI. Hybridized 8-mers are extended by a labeled dideoxynucleotide. After an optional purification step, i.e., with a size exclusion column, the labeled 9-mers are hybridized to the chip. Other methods of target fragmentation can be employed. The single-stranded DNA can be fragmented by partial degradation with a DNAse or partial depurination with acid. Labeling can be accomplished in a separate step, i.e., fluorophore-labeled nucleotides are incorporated before the fragmentation step or a DNA binding fluorophore, such as ethidium homodimer, is attached to the target after fragmentation.

In one embodiment, the DNA chip has an array of $10^4$ to $10^5$ probes tiling across the protein coding regions of p53, which comprise about 1200 bp; smaller arrays specific for the 600 bp mutational hot spot region are also useful. The probes overlap for N-2 to N-4 bases, where N is the length of the probe in bases. N is typically 10 to 14 bases long, but as will be seen below, probes 15 to 19 bases and longer are also useful. Every possible single base substitution occurring one at a time is represented in the array. The number of unique 10-mer probes with 7 base overlaps would be about (1200/3)×4×10 or about $1.6 \times 10^4$. To allow 3 replicates of each probe, one might have a total array size on the order of $4.8 \times 10^4$ probes. Of course, arrays of probes within the ranges of $10^2$ to $10^6$ probes are also useful for applications; for example, very large arrays of $10^6$ or more probes are useful for sequencing or sequence checking large genomic DNA fragments. Optionally fragmented and labeled target nucleic acid hybridized to the chip is detected by a confocal microscope or other imaging device. The pattern of sites "lighting up" with target is preferably analyzed with computer assistance to provide the sequence of the target from the pattern of sites producing signals.

The invention is illustrated below with examples of DNA chips comprising very large arrays of DNA probes to "resequence" p53 target nucleic acid in a sample. To analyze DNA from exon 5 of the p53 tumor suppressor gene, a set of overlapping 17-mer probes was synthesized on a chip. The probes for the WT allele were synthesized so as to tile across the entire exon with single base overlaps between probes. For each WT probe, a sets of 4 additional probes, one for each possible base substitution at position 7, were synthesized and placed in a column relative to the WT probe. Exon 5 DNA was amplified by PCR with primers flanking the exon. One of the primers was labeled with fluorescein; the other primer was labeled with biotin. After amplification, the biotinylated strand was removed by binding to streptavidin beads. The fluoresceinated strand was used in hybridization.

About ⅓ of the amplified, single-stranded nucleic acid was hybridized overnight in 5×SSPE at 60° C. to the probe chip (under a cover slip). After washing with 6×SSPE, the chip was scanned using confocal microscopy. FIG. 26 shows an image of the p53 chip hybridized to the target DNA. Analysis of the intensity data showed that 93.5% of the 184 bases of exon 5 were called in agreement with the WT sequence (see Buchman et al., 1988, *Gene* 70: 245–252, incorporated herein by reference). The miscalled bases were from positions where probe signal intensities were tied (1.6%) and where non-WT probes had the highest signal intensity (4.9%). FIG. 27 illustrates how the actual sequence was read. Gaps in the sequence of letters in the WT rows correspond to control probes or sites. Positions at which bases are miscalled are represented by letters in italic type in cells corresponding to probes in which the WT bases have been substituted by other bases.

As the diagram indicates, the miscalled bases are from the low intensity areas of the image, which may be due to secondary structure in the target or probes preventing intermolecular hybridization. To diminish the effects due to secondary structure, one can employ shorter targets (i.e., by target fragmentation) or use more stringent hybridization conditions. In addition, the use of a set of probes synthesized by tiling across the other strand of a duplex target can also provide sequence information buried in secondary structure in the other strand. It should be appreciated, however, that the pattern of low intensity areas that forms as a result of secondary structure in the target itself provides a means to identify that a specific target sequence is present in a sample. Other factors that may contribute to lower signal intensities include differences in probe densities and hybridization stabilities.

These results demonstrate the advantages provided by the DNA chips of the invention to genetic analysis. As another example, heterozygous mutations are currently sequenced by an arduous process involving cloning and repurification of DNA. The cloning step is required, because the gel sequencing systems are poor at resolving even a 1:1 mixture of DNA. First, the target DNA is amplified by PCR with primers allowing easy ligation into a vector, which is taken up by transformation of *E. coli* which in turn must be cultured, typically on plates overnight. After growth of the bacteria, DNA is purified in a procedure that typically takes about 2 hours; then, the sequencing reactions are performed, which takes at least another hour, and the samples are run on the gel for several hours, the duration depending on the length of the fragment to be sequenced. By contrast, the present invention provides direct analysis of the PCR amplified material after brief transcription and fragmentation steps, saving days of time and labor.

An interesting clinical application for the characterization of heterozygous mutations with DNA chips is as follows. Individuals with germline cancer mutations have a very high risk for secondary tumors after treatment by irradiation. About 10% of all cancer patients may have germline mutations for p53 or other tumor suppressor genes. Thus, before deciding on a treatment modality, a physician could use the method and DNA chips of the invention to test for a germline suppressor gene mutation.

DNA Chips for Rational Therapeutic Management

The present invention also provides DNA chips that can be used by physicians to determine optimum therapeutic protocols by early, rapid detection of biologically mediated resistance to a therapeutic agent in a variety of disease states. The benefits of such DNA chips are many, as the chips will help physicians recognize health care cost savings, achieve rapid therapeutic benefits, limit administration of ineffective (due to the resistance) yet toxic drugs, monitor changes in pathogen resistance, and decrease pathogen acquisition of resistance. Important applications include the treatment of HIV, other infectious diseases, and cancer.

HIV has infected a large and expanding number of people, resulting in massive health care expenditures. HIV can rapidly become resistant to drugs used to treat the infection, primarily due to the action of the heterodimeric protein (51 kD and 66 kD) HIV reverse transcriptase (RT) encoded by the 1.7 kb pol gene. The high error rate (5–10 per round) of the RT protein is believed to account for the hypermutability of HIV. The nucleoside analogues, i.e., AZT, ddI, ddC, and d4T, commonly used to treat HIV infection are converted to nucleotide analogues by sequential phosphorylation in the cytoplasm of infected cells, where incorporation of the analogue into the viral DNA results in termination of viral replication, because the 5'→3' phosphodiester linkage cannot be completed. However, within after 6 months to 1 year of treatment, HIV typically mutates the RT gene so as to become incapable of incorporating the analogue and so resistant to treatment. Several known mutations are shown in tabular form below.

| RT MUTATIONS ASSOCIATED WITH DRUG RESISTANCE | | | |
|---|---|---|---|
| ANTI-VIRAL | CODON | aa CHANGE | nt CHANGE |
| AZT | 67 | Asp –> Asn | GAC –> AAC |
| AZT | 70 | Lys –> Arg | AAA –> AGA |
| AZT | 215 | Thr –> Phe or Tyr | ACC –> TTC or TAC |
| AZT | 219 | Lys –> Gln or Glu | AAA –> CAA or GAA |
| AZT | 41 | Met –> Leu | ATG –> TTG or CTG |
| ddI and ddC | 184 | Met –> Val | ATG –> GTG |
| ddI and ddC | 74 | Leu –> Val | |
| TIBO 82150 | 100 | Leu –> Ile | |

N.B. other mutations confer resistance to other drugs in vitro

The present invention provides DNA chips for detecting the multiple mutations in the HIV RT gene associated with resistance to different therapeutics. These DNA chips will enable physicians to monitor mutations over time and to change therapeutics if resistance develops. The DNA chip will provide redundant confirmation of conserved HIV RT and other gene sequences, and the probes on the chip will tile through, with overlap, in important mutational hot spot regions. The chip will optionally have probes that span the entire coding region of the RT and optionally the genes for other HIV proteins, such as coat proteins. HIV target nucleic acid can be isolated from blood samples (peripheral blood lymphocytes or PBMC) and amplified by PCR, primers for which are shown in the table below.

AMPLIFICATION OF TARGET

| TARGET SIZE | PRIMER 1 | PRIMER 2 |
|---|---|---|
| 1, 742bp | GTAGAATTCTGTTGACTCAGATTGG (SEQ ID. NO:292) | GATAAGCTTGGGCCTTATCTATTCCAT (SEQ ID. NO:294) |
| 535bp | AAATCCATACAATACTCCAGTATTTGC (SEQ ID. NO:293) | ACCCATCCAAAGGAATGGAGGTTCTTTC (SEQ ID. NO:295) |
| 323bp | Genbank#K02013 1889–1908 | bases 2211–2192 |

The HIV RT gene chips of the invention, as well as the CF, mtDNA, and p53 DNA chips of the invention, illustrate the diverse application of the methods and probe arrays of the invention. The examples that follow describe methods for preparing nucleic acid targets from samples for application to the DNA chips of the invention and provide additional details of the methods of the invention.

EXAMPLES

I. VLSIPS™ Technology

As noted above, the VLSIPS™ technology is described in a number of patent publications and is preferred for making the oligonucleotide arrays of the invention. For completeness, a brief description of how this technology can be used to make and screen DNA chips is provided in this Example and the accompanying Figures. In the VLSIPS method, light is shone through a mask to activate functional (for oligonucleotides, typically an —OH) groups protected with a photoremovable protecting group on a surface of a solid support. After light activation, a nucleoside building block, itself protected with a photoremovable protecting group (at the 5'—OH), is coupled to the activated areas of the support. The process can be repeated, using different masks or mask orientations and building blocks, to prepare very dense arrays of many different oligonucleotide probes. The process is illustrated in FIG. 28; FIG. 29 illustrates how the process can be used to prepare "nucleoside combinatorials" or oligonucleotides synthesized by coupling all four nucleosides to form dimers, trimers, etc.

New methods for the combinatorial chemical synthesis of peptide, polycarbamate, and oligonucleotide arrays have recently been reported (see Fodor et al., 1991, *Science* 251: 767–773; Cho et al., 1993, *Science* 261: 1303–1305; and Southern et al., 1992, *Genomics* 13: 1008–10017, each of which is incorporated herein by reference). These arrays, or biological chips (see Fodor et al., 1993, *Nature* 364: 555–556, incorporated herein by reference), harbor specific chemical compounds at precise locations in a high-density, information rich format, and are a powerful tool for the study of biological recognition processes. A particularly exciting application of the array technology is in the field of DNA sequence analysis. The hybridization pattern of a DNA target to an array of shorter oligonucleotide probes is used to gain primary structure information of the DNA target. This format has important applications in sequencing by hybridization, DNA diagnostics and in elucidating the thermodynamic parameters affecting nucleic acid recognition.

Conventional DNA sequencing technology is a laborious procedure requiring electrophoretic size separation of labeled DNA fragments. An alternative approach, termed Sequencing By Hybridization (SBH), has been proposed (Lysov et al., 1988, *Dokl. Akad. Nauk SSSR* 303: 1508–1511; Bains et al., 1988, *I. Theor. Biol.* 135: 303–307; and Drmanac et al., 1989, *Genomics* 4: 114–128, incorporated herein by reference). This method uses a set of short oligonucleotide probes of defined sequence to search for complementary sequences on a longer target strand of DNA. The hybridization pattern is used to reconstruct the target DNA sequence. It is envisioned that hybridization analysis of large numbers of probes can be used to sequence long stretches of DNA. In immediate applications of this hybridization methodology, a small number of probes can be used to interrogate local DNA sequence.

The strategy of SBH can be illustrated by the following example. A 12-mer target DNA sequence, AGCCTAGCTGAA, (SEQ. ID NO:296) is mixed with a complete set of octanucleotide probes. If only perfect complementarity is considered, five of the 65,536 octamer probes -TCGGATCG, CGGATCGA, GGATCGAC, GATCGACT, and ATCGACTT will hybridize to the target. Alignment of the overlapping sequences from the hybridizing probes reconstructs the complement of the original 12-mer target:

```
       TCGGATCG
        CGGATCGA
         GGATCGAC
          GATCGACT
           ATCGACTT
       TCGGATCGACTT (SEQ. ID NO:297)
```

Hybridization methodology can be carried out by attaching target DNA to a surface. The target is interrogated with a set of oligonucleotide probes, one at a time (see Strezoska et al., 1991, *Proc. Natl. Acad. Sci. USA* 88: 10089–10093, and Drmanac et al., 1993, *Science* 260: 1649–1652, each of which is incorporated herein by reference). This approach can be implemented with well established methods of immobilization and hybridization detection, but involves a large number of manipulations. For example, to probe a sequence utilizing a full set of octanucleotides, tens of thousands, of hybridization reactions must be performed. Alternatively, SBH can be carried out by attaching probes to a surface in an array format where the identity of the probes at each site is known. The target DNA is then added to the array of probes. The hybridization pattern determined in a single experiment directly reveals the identity of all complementary probes.

As noted above, a preferred method of oligonucleotide probe array synthesis involves the use of light to direct the synthesis of oligonucleotide probes in high-density, miniaturized arrays. Photolabile 5'-protected N-acyl-deoxynucleoside phosphoramidites, surface linker chemistry, and versatile combinatorial synthesis strategies have been developed for this technology. Matrices of spatially-defined oligonucleotide probes have been generated, and the ability to use these arrays to identify complementary sequences has been demonstrated by hybridizing fluorescent labeled oligonucleotides to the DNA chips produced by the methods. The hybridization pattern demonstrates a high degree of base specificity and reveals the sequence of oligonucleotide targets.

The basic strategy for light-directed oligonucleotide synthesis (1) is outlined in FIG. 28. The surface of a solid support modified with photolabile protecting groups (X) is illuminated through a photolithographic mask, yielding reactive hydroxyl groups in the illuminated regions. A 3'-O-phosphoramidite activated deoxynucleoside (protected at the 5'-hydroxyl with a photolabile group) is then presented to the surface and coupling occurs at sites that were exposed to light. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of products is obtained.

Light directed chemical synthesis lends itself to highly efficient synthesis strategies which will generate a maximum number of compounds in a minimum number of chemical steps. For example, the complete set of 4n polynucleotides (length n), or any subset of this set can be produced in only 4×n chemical steps. See FIG. 29. The patterns of illumination and the order of chemical reactants ultimately define the products and their locations. Because photolithography is used, the process can be miniaturized to generate high-density arrays of oligonucleotide probes. For an example of the nomenclature useful for describing such arrays, an array containing all possible octanucleotides of dA and dT is written as $(A+T)^8$. Expansion of this polynomial reveals the identity of all 256 octanucleotide probes from AAAAAAAA to TTTTTTTT. A DNA array composed of complete sets of dinucleotides is referred to as having a complexity of 2. The array given by $(A+T+C+G)8$ is the full 65,536 octanucleotide array of complexity four.

To carry out hybridization of DNA targets to the probe arrays, the arrays are mounted in a thermostatically controlled hybridization chamber. Fluorescein labeled DNA targets are injected into the chamber and hybridization is allowed to proceed for ½ to 2 hours. The surface of the matrix is scanned in an epifluorescence microscope (Zeiss Axioscop 20) equipped with photon counting electronics using 50–100 $\mu$W of 488 nm excitation from an Argon ion laser (Spectra Physics model 2020). All measurements are acquired with the target solution in contact with the probe matrix. Photon counts are stored and image files are presented after conversion to an eight bit image format. See FIG. 33.

When hybridizing a DNA target to an oligonucleotide array, $N=Lt-(Lp-1)$ complementary hybrids are expected, where N is the number of hybrids, Lt is the length of the DNA target, and Lp is the length of the oligonucleotide probes on the array. For example, for an 11-mer hybridized to an octanucleotide array, $N=4$. Hybridizations with mismatches at positions that are 2 to 3 residues from either end of the probes will generate detectable signals. Modifying the above expression for N, one arrives at a relationship estimating the number of detectable hybridizations (Nd) for a DNA target of length Lt and an array of complexity C. Assuming an average of 5 positions giving signals above background: $Nd=(1+5(C-1))[Lt-(Lp-1)]$.

Arrays of oligonucleotides can be efficiently generated by light-directed synthesis and can be used to determine the identity of DNA target sequences. Because combinatorial strategies are used, the number of compounds increases exponentially while the number of chemical coupling cycles increases only linearly. For example, expanding the synthesis to the complete set of $4^8$ (65,536) octanucleotides will add only four hours to the synthesis for the 16 additional cycles. Furthermore, combinatorial synthesis strategies can be implemented to generate arrays of any desired composition. For example, because the entire set of dodecamers ($4^{12}$) can be produced in 48 photolysis and coupling cycles (b''' compounds requires b×n cycles), any subset of the dodecamers (including any subset of shorter oligonucleotides) can be constructed with the correct lithographic mask design in 48 or fewer chemical coupling steps. In addition, the number of compounds in an array is limited only by the density of synthesis sites and the overall array size. Recent experiments have demonstrated hybridization to probes synthesized in 25 $\mu$m sites. At this resolution, the entire set of 65,536 octanucleotides can be placed in an array measuring 0.64 cm square, and the set of 1,048,576 dodecanucleotides requires only a 2.56 cm array.

Genome sequencing projects will ultimately be limited by DNA sequencing technologies. Current sequencing methodologies are highly reliant on complex procedures and require substantial manual effort. Sequencing by hybridization has the potential for transforming many of the manual efforts into more efficient and automated formats. Light-directed synthesis is an efficient means for large scale production of miniaturized arrays for SBH. The oligonucleotide arrays are not limited to primary sequencing applications. Because single base changes cause multiple changes in the hybridization pattern, the oligonucleotide arrays provide a powerful means to check the accuracy of previously elucidated DNA sequence, or to scan for changes within a sequence. In the case of octanucleotides, a single base change in the target DNA results in the loss of eight complements, and generates eight new complements. Matching of hybridization patterns may be useful in resolving sequencing ambiguities from standard gel techniques, or for rapidly detecting DNA mutational events. The potentially very high information content of light-directed oligonucleotide arrays will change genetic diagnostic testing. Sequence comparisons of hundreds to thousands of different genes will be assayed simultaneously instead of the current one, or few at a time format. Custom arrays can also be constructed to contain genetic markers for the rapid identification of a wide variety of pathogenic organisms.

Oligonucleotide arrays can also be applied to study the sequence specificity of RNA or protein-DNA interactions. Experiments can be designed to elucidate specificity rules of non Watson-Crick oligonucleotide structures or to investigate the use of novel synthetic nucleoside analogs for antisense or triple helix applications. Suitably protected RNA monomers may be employed for RNA synthesis. The oligonucleotide arrays should find broad application deducing the thermodynamic and kinetic rules governing formation and stability of oligonucleotide complexes.

Other than the use of photoremovable protecting groups, the nucleoside coupling chemistry is very similar to that used routinely today for oligonucleotide synthesis. FIG. 30 shows the deprotection, coupling, and oxidation steps of a solid phase DNA synthesis method. FIG. 31 shows an illustrative synthesis route for the nucleoside building blocks used in the method. FIG. 32 shows a preferred photoremovable protecting group, MeNPOC, and how to prepare the group in active form. The procedures described below show how to prepare these reagents. The nucleoside building blocks are 5'-MeNPOC-THYMIDINE-3'-OCEP; 5'-MeNPOC-N⁴-t-BUTYL PHENOXYACETYL-DEOXYCYTIDINE-3'-OCEP; 5'-MeNPOC-N⁴-t-BUTYL PHENOXYACETYL-DEOXYGUANOSINE-3'-OCEP; and 5'-MeNPOC-N⁴-t-BUTYL PHENOXYACETYL-DEOXYADENOSINE-3'-OCEP.

A. Preparation of 4, 5-methylenedioxy-2-nitroacetophenone

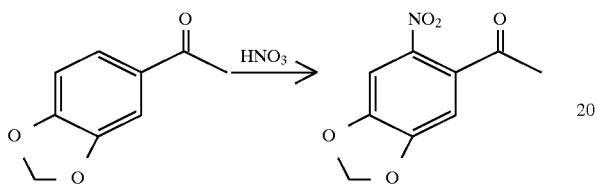

A solution of 50 g (0.305 mole) 3,4-methylenedioxyacetophenone (Aldrich) in 200 mL glacial acetic acid was added dropwise over 30 minutes to 700 mL of cold (2-4° C.) 70% HNO₃ with stirring (NOTE: the reaction will overheat without external cooling from an ice bath, which can be dangerous and lead to side products). At temperatures below 0° C., however, the reaction can be sluggish. A temperature of 3°–5° C. seems to be optimal). The mixture was left stirring for another 60 minutes at 3°–5° C., and then allowed to approach ambient temperature. Analysis by TLC (25% EtOAc in hexane) indicated complete conversion of the starting material within 1–2 hr. When the reaction was complete, the mixture was poured into ~3 liters of crushed ice, and the resulting yellow solid was filtered off, washed with water and then suction-dried. Yield ~53 g (84%), used without further purification.

B. Preparation of 1-(4,5-Methylenedioxy-2-nitrophenyl) ethanol

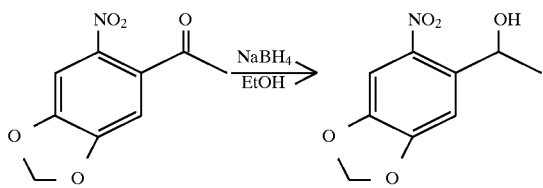

Sodium borohydride (10 g; 0.27 mol) was added slowly to a cold, stirring suspension of 53 g (0.25 mol) of 4,5-methylenedioxy-2-nitroacetophenone in 400 mL methanol. The temperature was kept below 10° C. by slow addition of the NaBH₄ and external cooling with an ice bath. Stirring was continued at ambient temperature for another two hours, at which time TLC (CH₂Cl₂) indicated complete conversion of the ketone. The mixture was poured into one liter of ice-water and the resulting suspension was neutralized with ammonium chloride and then extracted three times with 400 mL CH₂Cl₂ or EtOAc (the product can be collected by filtration and washed at this point, but it is somewhat soluble in water and this results in a yield of only ~60%). The combined organic extracts were washed with brine, then dried with MgSO₄ and evaporated. The crude product was purified from the main byproduct by dissolving it in a minimum volume of CH₂Cl₂ or THF(~175 ml) and then precipitating it by slowly adding hexane (1000 ml) while stirring (yield 51 g; 80% overall). It can also be recrystallized (eg., toluene-hexane), but this reduces the yield.

C. Preparation of 1-(4,5- methylenedioxy-2-nitrophenyl) ethyl chloroformate (MeNPOC-Cl)

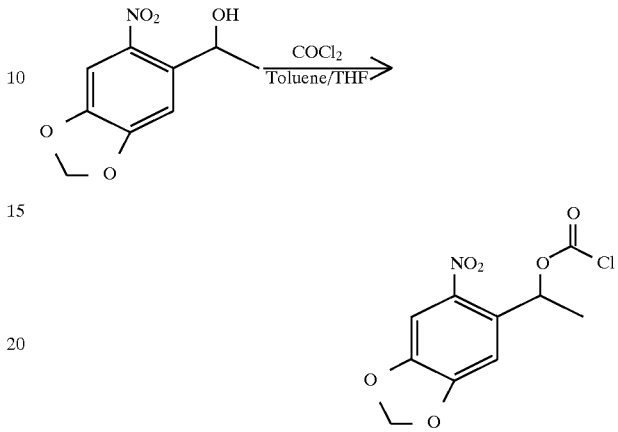

Phosgene (500 mL of 20% w/v in toluene from Fluka: 965 mmole; 4 eq.) was added slowly to a cold, stirring solution of 50 g (237 mmole; 1 eq.) of 1-(4,5-methylenedioxy-2-nitrophenyl)ethanol in 400 mL dry THF. The solution was stirred overnight at ambient temperature at which point TLC (20% Et₂O/hexane) indicated >95% conversion. The mixture was evaporated (an oil-less pump with downstream aqueous NaOH trap is recommended to remove the excess phosgene) to afford a viscous brown oil. Purification was effected by flash chromatography on a short (9×13 cm) column of silica gel eluted with 20% Et₂O/hexane. Typically 55 g (85%) of the solid yellow MeNPOC-Cl is obtained by this procedure. The crude material has also been recrystallized in 2–3 crops from 1:1 ether/hexane. On this scale, ~100 ml is used for the first crop, with a few percent THF added to aid dissolution, and then cooling overnight at –20° C. (this procedure has not been optimized). The product should be stored dessicated at –20° C.

D. Synthesis of 5'-MeNPOC-2'-DEOXYNUCLEOSIDE-3'-(N,N-DIISOPROPYL 2-CYANOETHYL PHOSPHORAMIDITES (1) 5'-MeNPOC-Nucleosides

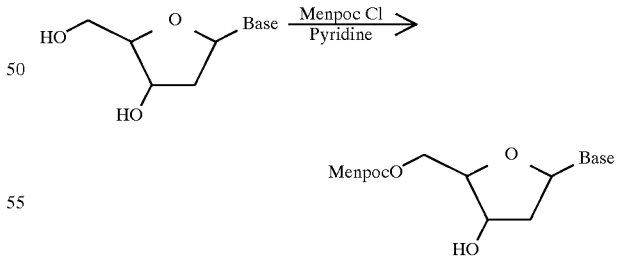

Base=THYMIDINE (T); N-4-ISOBUTYRYL 2'-DEOXYCYTIDINE (ibu-dC); N-2-PHENOXYACETYL 2'DEOXYGUANOSINE (PAC-dG); and N-6-PHENOXYACETYL 2'DEOXYADENOSINE (PAC-dA)

All four of the 5'-MeNPOC nucleosides were prepared from the base-protected 2'-deoxynucleosides by the following procedure. The protected 2'-deoxynucleoside (90 mmole) was dried by co-evaporating twice with 250 mL anhydrous pyridine. The nucleoside was then dissolved in 300 mL anhydrous pyridine (or 1:1 pyridine/DMF, for the dG$^{PAC}$ nucleoside) under argon and cooled to ~2° C. in an ice bath. A solution of 24.6 g (90 mmole) MeNPOC-Cl in 100 mL dry THP was then added with stirring over 30 minutes. The ice bath was removed, and the solution allowed to stir overnight at room temperature (TLC: 5–10% MeOH in $CH_2Cl_2$; two diastereomers). After evaporating the solvents under vacuum, the crude material was taken up in 250 mL ethyl acetate and extracted with saturated aqueous $NaHCO_3$ and brine. The organic phase was then dried over $Na_2SO_4$, filtered and evaporated to obtain a yellow foam. The crude products were finally purified by flash chromatography (9×30 cm silica gel column eluted with a stepped gradient of 2%–6% MeOH in $CH_2Cl_2$). Yields of the purified diastereomeric mixtures are in the range of 65–75%.

(2) 5'-MeNPOC-2'-DEOXYNUCLEOSIDE-3'-(N,N-DIISOPROPYL 2-CYANOETHYL PHOSPHORAMIDITES)

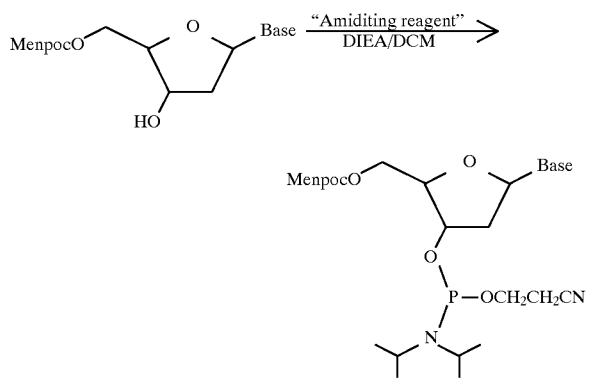

The four deoxynucleosides were phosphitylated using either 2-cyanoethyl-N,N-diisopropyl chlorophosphoramidite, or 2-cyanoethyl-N,N,N',N'-tetraisopropylphosphorodiamidite. The following is a typical procedure. Add 16.6 g (17.4 ml; 55 mmole) of 2-cyanoethyl-N,N,N',N'-tetraisopropylphosphorodiamidite to a solution of 50 mmole 5'-MeNPOC-nucleoside and 4.3 g (25 mmole) diisopropylammonium tetrazolide in 250 mL dry $CH_2Cl_2$ under argon at ambient temperature. Continue stirring for 4–16 hours (reaction monitored by TLC: 45:45:10 hexane/$CH_2Cl_2$/$Et_3N$). Wash the organic phase with saturated aqueous $NaHCO_3$ and brine, then dry over $Na_2SO_4$, and evaporate to dryness. Purify the crude amidite by flash chromatography (9×25 cm silica gel column eluted with hexane/$CH_2Cl_2$/TEA -45:45:10 for A, C, T; or 0:90:10 for G). The yield of purified amidite is about 90%.

II. PREPARATION OF LABELED DNA/HYBRIDIZATION TO ARRAY

1) PCR

PCR amplification reactions are typically conducted in a mixture composed of per reaction: 1 μl genomic DNA; 10 μl each primer (10 pmol/μl stocks); 10 μl 10×PCR buffer (100 mM Tris.Cl pH8.5, 500 mM KCl, 15 mM $MgCl_2$); 10 μl 2 mM dNTPs (made from 100 mM dNTP stocks); 2.5 U Taq polymerase (Perkin Elmer AmpliTaq™, 5 U/μl); and $H_2O$ to 100 μl. The cycling conditions are usually 40 cycles (94° C. 45 sec, 55° C. 30 sec, 72° C. 60 sec) but may need to be varied considerably from sample type to sample type. These conditions are for 0.2 mL thin wall tubes in a Perkin Elmer 9600 thermocycler. See Perkin Elmer 1992/93 catalogue for 9600 cycle time information. Target, primer length and sequence composition, among other factors, may also affect parameters.

For products in the 200 to 1000 bp size range, check 2 μl of the reaction on a 1.5% 0.5×TBE agarose gel using an appropriate size standard (phiX174 cut with HaeIII is convenient). The PCR reaction should yield several picomoles of product. It is helpful to include a negative control (i.e., 1 μl TE instead of genomic DNA) to check for possible contamination. To avoid contamination, keep PCR products from previous experiments away from later reactions, using filter tips as appropriate. Using a set of working solutions and storing master solutions separately is helpful, so long as one does not contaminate the master stock solutions.

For simple amplifications of short fragments from genomic DNA it is, in general, unnecessary to optimize $Mg^{2+}$ concentrations. A good procedure is the following: make a master mix minus enzyme; dispense the genomic DNA samples to individual tubes or reaction wells; add enzyme to the master mix; and mix and dispense the master solution to each well, using a new filter tip each time.

2) PURIFICATION

Removal of unincorporated nucleotides and primers from PCR samples can be accomplished using the Promega Magic PCR Preps DNA purification kit. One can purify the whole sample, following the instructions supplied with the kit (proceed from section IIIB, 'Sample preparation for direct purification from PCR reactions'). After elution of the PCR product in 50 μl of TE or $H_2O$, one centrifuges the eluate for 20 sec at 12,000 rpm in a microfuge and carefully transfers 45 μl to a new microfuge tube, avoiding any visible pellet. Resin is sometimes carried over during the elution step. This transfer prevents accidental contamination of the linear amplification reaction with 'Magic PCR' resin. Other methods, e.g. size exclusion chromatography, may also be used.

3) LINEAR AMPLIFICATION

In a 0.2 mL thin-wall PCR tube mix: 4 μl purified PCR product; 2 μl primer (10 pmol/μl); 4 μl 10×PCR buffer; 4 μl dNTPs (2 mM dA, dC, dG, 0.1 mM dT); 4 μl 0.1 mM dUTP; 1 μl 1 mM fluorescein dUTP (Amersham RPN 2121); 1 U Taq polymerase (Perkin Elmer, 5 U/μl); and add $H_2O$ to 40 μl. Conduct 40 cycles (92° C. 30 sec, 55° C. 30 sec, 72° C. 90 sec) of PCR. These conditions have been used to amplify a 300 nucleotide mitochondrial DNA fragment but are generally applicable. Even in the absence of a visible product band on an agarose gel, there should still be enough product to give an easily detectable hybridization signal. If one is not treating the DNA with uracil DNA glycosylase (see Section 4), dUTP can be omitted from the reaction.

4) FRAGMENTATION

Purify the linear amplification product using the Promega Magic PCR Preps DNA purification kit, as per Section 2 above. In a 0.2 mL thin-wall PCR tube mix: 40 μl purified labeled DNA; 4 μl 10×PCR buffer; and 0.5 μl uracil DNA glycosylase (BRL 1U/μl). Incubate the mixture 15 min at 37° C., then 10 min at 97° C.; store at −20° C. until ready to use.

5) HYBRIDIZATION SCANNING & STRIPPING

A blank scan of the slide in hybridization buffer only is helpful to check that the slide is ready for use. The buffer is removed from the flow cell and replaced with 1 mL of (fragmented) DNA in hybridization buffer and mixed well. The scan is performed in the presence of the labeled target. FIG. 33 illustrates an illustrative detection system for scanning a DNA chip. A series of scans at 30 min intervals using a hybridization temperature of 25° C. yields a very clear signal, usually in at least 30 min to two hours, but it may be desirable to hybridize longer, i.e., overnight. Using a laser power of 50 μW and 50 μm pixels, one should obtain maximum counts in the range of hundreds to low thousands/ pixel for a new slide. When finished, the slide can be stripped using 50% formamide. rinsing well in deionized H₂O, blowing dry, and storing at room temperature.

III. PREPARATION OF LABELED RNA /HYBRIDIZATION TO ARRAY

1) TAGGED PRIMERS

The primers used to amplify the target nucleic acid should have promoter sequences if one desires to produce RNA from the amplified nucleic acid. Suitable promoter sequences are shown below and include:

(1) the T3 promoter sequence:
5'-CGGAATTAACCCTCACTAAAGG (SEQ. ID NO:298)
5'-AATTAACCCTCACTAAAGGGAG; (SEQ. ID NO:299)
(2) the T7 promoter sequence:
5' TAATACGACTCACTATAGGGAG; (SEQ. ID NO:300)
and (3) the SP6 promoter sequence:
5' ATTTAGGTGACACTATAGAA. (SEQ. ID NO:301)

The desired promoter sequence is added to the 5' end of the PCR primer. It is convenient to add a different promoter to each primer of a PCR primer pair so that either strand may be transcribed from a single PCR product.

Synthesize PCR primers so as to leave the DMT group on. DMT-on purification is unnecessary for PCR but appears to be important for transcription. Add 25 μl 0.5M NaOH to collection vial prior to collection of oligonucleotide to keep the DMT group on. Deprotect using standard chemistry—55° C. overnight is convenient.

HPLC purification is accomplished by drying down the oligonucleotides, resuspending in 1 mL 0.1M TEAA (dilute 2.0M stock in deionized water, filter through 0.2 micron filter) and filter through 0.2 micron filter. Load 0.5 mL on reverse phase HPLC (column can be a Hamilton PRP-1 semi-prep, #79426). The gradient is 0→50% CH₃CN over 25 min (program 0.2 μmol.prep.0–50, 25 min). Pool the desired fractions, dry down, resuspend in 200 μl 80% HAc. 30 min RT. Add 200 μl EtOH; dry down. Resuspend in 200 μl H₂O, plus 20 μl NaAc pH5.5, 600 μl EtOH. Leave 10 min on ice; centrifuge 12,000 rpm for 10 min in microfuge. Pour off supernatant. Rinse pellet with 1 mL EtOH, dry, resuspend in 200 μl H2O. Dry, resuspend in 200 μl TE. Measure A260, prepare a 10 pmol/μl solution in TE (10 mM Tris.Cl pH 8.0, 0.1 mM EDTA). Following HPLC purification of a 42 mer, a yield in the vicinity of 15 nmol from a 0.2 μmol scale synthesis is typical.

2) GENOMIC DNA PREPARATION

For obtaining genomic DNA from human hair, one can extract as few as 5 hairs, including hair roots. On a clean and sterile surface, one places the hair on a piece of parafilm, and after wiping a new razor blade with EtOH cutting off the roots, the roots are transferred to a 1.5 mL microfuge tube using a pair of Millipore forceps cleaned with EtOH. Add 500 μl (10 mM Tris.Cl pH8.0, 10 mM EDTA, 100 mM NaCl, 2% (w/v) SDS, 40 mM DTT, filter sterilized) to the sample. Add 1.25 μl 20 mg/ml proteinase K (Boehringer) Incubate at 55° C. for 2 hours, vortexing once or twice. Perform 2×0.5 mL 1:1 phenol:CHCl₃ extractions. After each extraction, centrifuge 12,000 rpm 5 min in a microfuge and recover 0.4 mL supernatant. Add 35 μl NaAc pH5.2 plus 1 mL EtOH. Place sample on ice 45 min; then centrifuge 12,000 rpm 30 min, rinse, air dry 30 min, and resuspend in 100 μl TE.

3) PCR

PCR is performed in a mixture containing, per reaction: 1 μl genomic DNA; 4 μl each primer (10 pmol/μl stocks); 4 μl 10 ×PCR buffer (100 mM Tris.Cl pH8.5, 500 mM KCl, 15 mM MgCl₂); 4 μl 2 mM dNTPs (made from 100 mM dNTP stocks); 1 U Taq polymerase (Perkin Elmer, 5 U/μl); H₂O to 40 μl. About 40 cycles (94° C. 30 sec, 55° C. 30 sec, 72° C. 30 sec) are performed, but cycling conditions may need to be varied. These conditions are for 0.2 mL thin wall tubes in Perkin Elmer 9600. For products in the 200 to 1000 bp size range, check 2 μl of the reaction on a 1.5% 0.5×TBE agarose gel using an appropriate size standard. For larger or smaller volumes (20–100 μl), one can use the same amount of genomic DNA but adjust the other ingredients accordingly.

4) IN VITRO TRANSCRIPTION

Mix: 3 μl PCR product; 4 μl 5×buffer; 2 μl DTT; 2.4 μl 10 mM rNTPs (100 mM solutions from Pharmacia); 0.48 μl 10 mM fluorescein-UTP (Fluorescein-12-UTP, 10 mM solution, from Boehringer Mannheim); 0.5 μl RNA polymerase (Promega T3 or T7 RNA polymerase); and add H₂O to 20 μl. Incubate at 37° C. for 3 h. Check 2 μl of the reaction on a 1.5% 0.5×TBE agarose gel using a size standard. 5×buffer is 200 mM Tris pH 7.5, 30 mM MgCl₂, 10 mM spermidine, 50 mM NaCl, and 100 mM DTT (supplied with enzyme). The PCR product needs no purification and can be added directly to the transcription mixture. A 20 μl reaction is suggested for an initial test experiment and hybridization; a 100 μl reaction is considered "preparative" scale (the reaction can be scaled up to obtain more target). The amount of PCR product to add is variable; typically a PCR reaction will yield several picomoles of DNA. If the PCR reaction does not produce that much target, then one should increase the amount of DNA added to the transcription reaction (as, well as optimize the PCR). The ratio of fluorescein-UTP to UTP suggested above is 1:5, but ratios from 1:3 to 1:10—all work well. One can also label with biotin-UTP and detect with streptavidin-FITC to obtain similar results as with fluorescein-UTP detection.

For nondenaturing agarose gel electrophoresis of RNA, note that the RNA band will normally migrate somewhat faster than the DNA template band, although sometimes the two bands will comigrate. The temperature of the gel can effect the migration of the RNA band. The RNA produced from in vitro transcription is quite stable and can be stored for months (at least) at −20° C. without any evidence of degradation. It can be stored in unsterilized 6×SSPE 0.1% triton X- 100 at −20° C. for days (at least) and reused twice (at least) for hybridization, without taking any special precautions in preparation or during use. RNase contamination should of course be avoided. When extracting RNA from cells, it is preferable to work very rapidly and to use strongly denaturing conditions. Avoid using glassware previously contaminated with RNases. Use of new disposable plasticware (not necessarily sterilized) is preferred, as new plastic tubes, tips, etc., are essentially RNase free. Treatment with DEPC or autoclaving is typically not unnecessary.

5) FRAGMENTATION

In a 0.2 mL thin-wall PCR tube mix: 18 μl RNA (direct from transcription reaction—no purification required); 18 μl H₂O; and 4 μl 1M Tris.Cl pH9.0. Incubate at 99.9° C. for 60 min. Add to 1 mL hybridization buffer and store at −20° C. until ready to use. The alkaline hydrolysis step is very reliable. The hydrolysed target can be stored at −20° C. in 6×SSPE/0.1% Triton X-100 for at least several days prior to use and can also be reused.

6) HYBRIDIZATION SCANNING, & STRIPPING

A blank scan of the slide in hybridization buffer only is helpful to check that the slide is ready for use. The buffer is removed from the flow cell and replaced with 1 mL of (hydrolysed) RNA in hybridization buffer and mixed well. Incubate for 15–30 min at 18° C. Remove the hybridization solution, which can be saved for subsequent experiments. Rinse the flow cell 4–5 times with fresh changes of 6×SSPE/ 0.1% Triton X-100, equilibrated to 18° C. The rinses can be performed rapidly, but it is important to empty the flow cell before each new rinse and to mix the liquid in the cell thoroughly. The scan is performed in the presence of the labeled target. A series of scans at 30 min intervals using a hybridization temperature of 25° C. yields a very clear signal, usually in at least 30 min to two hours, but it may be desirable to hybridize longer, i.e., overnight. Using a laser power of 50 µW and 50 µm pixels, one should obtain maximum counts in the range of hundreds to low thousands/pixel for a new slide. When finished, the slide can be stripped using 50% to 100% formamide at 50° C. for 30 min, rinsing well in deionized H$_2$O, blowing dry, and storing at room temperature.

These conditions are illustrative and assume a probe length of ~15 nucleotides. The stripping conditions suggested are fairly severe, but some signal may remain on the slide if the washing is not stringent. Nevertheless, the counts remaining after the wash should be very low in comparison to the signal in presence of target RNA. In some cases, much gentler stripping conditions are effective. The lower the hybridization temperature and the longer the duration of hybridization, the more difficult it is to strip the slide. Longer targets may be more difficult to strip than shorter targets.

SEQUENCE LISTING ( 1 ) GENERAL INFORMATION:

( i i i ) NUMBER OF SEQUENCES: 360

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:1:

T T G C T G A C G T   C A G C C	15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:2:

T T G C T G A C A T   C A G C C	15

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:3:

T T G C T G A C C T   C A G C C	15

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:4:

TTGCTGACTT CAGCC 15

( 2 ) INFORMATION FOR SEQ ID NO:5:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:5:

CATTAAAGAA AATATCATCT TTGGTGTTTC CTATGATGA 39

( 2 ) INFORMATION FOR SEQ ID NO:6:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:6:

CATTAAAGAA AATATCATTG GTGTTTCCTA TGATGA 36

( 2 ) INFORMATION FOR SEQ ID NO:7:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

CATTAAAGAA AATATCATTG GTGTTTCCTA TGATGA 36

( 2 ) INFORMATION FOR SEQ ID NO:8:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:8:

AACACCAATG ATGAT 15

( 2 ) INFORMATION FOR SEQ ID NO:9:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:9:

CCAAAGATNA TATTT 15

( 2 ) INFORMATION FOR SEQ ID NO:10:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:10:

ACCAAAGANG ATATT    15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:11:

CACCAAAGNT GATAT    15

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:12:

ACACCAAANA TGATA    15

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:13:

AACACCAANG ATGAT    15

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:14:

AAACACCANA GATGA    15

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (i i) MOLECULE TYPE: DNA (probe)

(x i) SEQUENCE DESCRIPTION: SEQ ID NO:15:

GAAACACCNA AGATG                                                                                           15

(2) INFORMATION FOR SEQ ID NO:16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:16:

GGAAACACNA AAGAT                                                                                           15

(2) INFORMATION FOR SEQ ID NO:17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:17:

AGGAAACANC AAAGA                                                                                           15

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:18:

CCTTCAGAGG GTAAAATTAA G                                                                                    21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:19:

CCTTCAGAGT GTAAAATTAA G                                                                                    21

(2) INFORMATION FOR SEQ ID NO:20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:20:

TAATACGACT CACTATAGGG AGATGACCTA ATAATGATGG GTTT                44

( 2 ) INFORMATION FOR SEQ ID NO:21:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:21:

TAATACGACT CACTATAGGG AGTAGTGTGA AGGGTTCATA TGC                 43

( 2 ) INFORMATION FOR SEQ ID NO:22:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:22:

CTCGGAATTA ACCCTCACTA AAGGTAGTGT GAAGGGTTCA TATGC               45

( 2 ) INFORMATION FOR SEQ ID NO:23:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:23:

TAATACGACT CACTATAGGG AGAGCATACT AAAAGTGACT CTC                 43

( 2 ) INFORMATION FOR SEQ ID NO:24:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:24:

TAATACGACT CACTATAGGG AGACATGAAT GACATTTACA GCAA                44

( 2 ) INFORMATION FOR SEQ ID NO:25:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:25:

CGGAATTAAC CCTCACTAAA GGACATGAAT GACATTTACA GCAA                44

( 2 ) INFORMATION FOR SEQ ID NO:26:

( i ) SEQUENCE CHARACTERISTICS:
   ( A ) LENGTH: 12 base pairs
   ( B ) TYPE: nucleic acid
   ( C ) STRANDEDNESS: single
   ( D ) TOPOLOGY: linear ( i i ) MOLECULE TYPE: DNA (probe)

( x i ) SEQUENCE DESCRIPTION: SEQ ID NO:26:

TTTATGGGGT GA 12

( 2 ) INFORMATION FOR SEQ ID NO:27:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:27:

TTGATTTATG GG 12

( 2 ) INFORMATION FOR SEQ ID NO:28:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:28:

AACCTATTTG ATT 13

( 2 ) INFORMATION FOR SEQ ID NO:29:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:29:

GGACCAAACC TA 12

( 2 ) INFORMATION FOR SEQ ID NO:30:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:30:

AGGCTAGGAC CA 12

( 2 ) INFORMATION FOR SEQ ID NO:31:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear (i i) MOLECULE TYPE: DNA (probe)

(x i) SEQUENCE DESCRIPTION: SEQ ID NO:31:

GGTGTGTGTG TGC            13

(2) INFORMATION FOR SEQ ID NO:32:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:32:

CGGTGTGTGT GTGC            14

(2) INFORMATION FOR SEQ ID NO:33:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:33:

GGTGTGTGTG TGCT            14

(2) INFORMATION FOR SEQ ID NO:34:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:34:

CTGGGTAGGA TG            12

(2) INFORMATION FOR SEQ ID NO:35:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:35:

TGCTGGGTAG GA            12

(2) INFORMATION FOR SEQ ID NO:36:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:36:

TGTGCTGGGT AG 12

( 2 ) INFORMATION FOR SEQ ID NO:37:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:37:

GTTAGCAGCG GT 12

( 2 ) INFORMATION FOR SEQ ID NO:38:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:38:

GGGTTAGCAG CG 12

( 2 ) INFORMATION FOR SEQ ID NO:39:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:39:

AGCGGGGGAG G 11

( 2 ) INFORMATION FOR SEQ ID NO:40:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:40:

AGCGGGGGAG 10

( 2 ) INFORMATION FOR SEQ ID NO:41:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:41:

GGTTGGTTCG G 11

( 2 ) INFORMATION FOR SEQ ID NO:42:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:42:

GGGTTTGGTT GG 12

( 2 ) INFORMATION FOR SEQ ID NO:43:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:43:

GATCTTTGGG GT 12

( 2 ) INFORMATION FOR SEQ ID NO:44:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:44:

GGGTGATCTT TG 12

( 2 ) INFORMATION FOR SEQ ID NO:45:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:45:

TGTGGGGGGT GA 12

( 2 ) INFORMATION FOR SEQ ID NO:46:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:46:

TAAACTGTGG GG 12

( 2 ) INFORMATION FOR SEQ ID NO:47:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:47:

GCTACATAAA CTG                                                                                    13

( 2 ) INFORMATION FOR SEQ ID NO:48:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:48:

GAGGTAAGCT ACA                                                                                    13

( 2 ) INFORMATION FOR SEQ ID NO:49:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:49:

GAGGAGGTAA GC                                                                                     12

( 2 ) INFORMATION FOR SEQ ID NO:50:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:50:

TGCTTTGAGG AG                                                                                     12

( 2 ) INFORMATION FOR SEQ ID NO:51:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:51:

AGTGTATTGC TTT                                                                                    13

( 2 ) INFORMATION FOR SEQ ID NO:52:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:52:

CATTTTCAGT GTA 13

(2) INFORMATION FOR SEQ ID NO:53:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:53:

TAAACATTTT CAG 13

(2) INFORMATION FOR SEQ ID NO:54:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:54:

AGCCCGTCTA AA 12

(2) INFORMATION FOR SEQ ID NO:55:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:55:

GAGCCCGTCT AA 12

(2) INFORMATION FOR SEQ ID NO:56:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:56:

TGATGTGAGC CC 12

(2) INFORMATION FOR SEQ ID NO:57:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:57:

GGGGTGATGT GA 12

(2) INFORMATION FOR SEQ ID NO:58:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:58:

GAGTGGGAGG G                                                                     11

( 2 ) INFORMATION FOR SEQ ID NO:59:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:59:

GTATGGGAGT GG                                                             12

( 2 ) INFORMATION FOR SEQ ID NO:60:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:60:

GATTAGTAGT ATGG                                                        14

( 2 ) INFORMATION FOR SEQ ID NO:61:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:61:

TGAATGAGAT TAG                                                          13

( 2 ) INFORMATION FOR SEQ ID NO:62:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:62:

ATTGAATGAG ATT                                                         13

( 2 ) INFORMATION FOR SEQ ID NO:63:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:63:

GGGTTGTATT GAA                                                                                                              1 3

( 2 ) INFORMATION FOR SEQ ID NO:64:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:64:

GCGGGGGTTG                                                                                                                  1 0

( 2 ) INFORMATION FOR SEQ ID NO:65:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:65:

ATGGGCGGGG                                                                                                                  1 0

( 2 ) INFORMATION FOR SEQ ID NO:66:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:66:

TAGGATGGGC G                                                                                                                1 1

( 2 ) INFORMATION FOR SEQ ID NO:67:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:67:

TGGGTAGGAT GG                                                                                                               1 2

( 2 ) INFORMATION FOR SEQ ID NO:68:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:68:

GTGCTGGGTA GG                                                                                    12

( 2 ) INFORMATION FOR SEQ ID NO:69:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:69:

TGTGTGTGCT GG                                                                                    12

( 2 ) INFORMATION FOR SEQ ID NO:70:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:70:

GCGGTGTGTG TG                                                                                    12

( 2 ) INFORMATION FOR SEQ ID NO:71:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:71:

TAGCAGCGGT GT                                                                                    12

( 2 ) INFORMATION FOR SEQ ID NO:72:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:72:

TGGGGTTAGC AG                                                                                    12

( 2 ) INFORMATION FOR SEQ ID NO:73:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:73:

GGTATGGGGT TA                                                                                    12

( 2 ) INFORMATION FOR SEQ ID NO:74:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:74:

GTTCGGGGTA TG     12

( 2 ) INFORMATION FOR SEQ ID NO:75:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:75:

GCTGGTGTTA GG     12

( 2 ) INFORMATION FOR SEQ ID NO:76:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:76:

GGTTAGGCTG GT     12

( 2 ) INFORMATION FOR SEQ ID NO:77:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:77:

AAATCTGGTT AGG    13

( 2 ) INFORMATION FOR SEQ ID NO:78:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:78:

AAATTTGAAA TCT    13

( 2 ) INFORMATION FOR SEQ ID NO:79:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:79:

AAGATAAAAT TTG 13

( 2 ) INFORMATION FOR SEQ ID NO:80:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:80:

GCCAAAAGA TA 12

( 2 ) INFORMATION FOR SEQ ID NO:81:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:81:

CGCCAAAAG A 11

( 2 ) INFORMATION FOR SEQ ID NO:82:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:82:

CATACCGCCA A 11

( 2 ) INFORMATION FOR SEQ ID NO:83:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:83:

AAAAGTGCAT ACC 13

( 2 ) INFORMATION FOR SEQ ID NO:84:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:84:

TGTTAAAAGT GCA 13

( 2 ) INFORMATION FOR SEQ ID NO:85:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:85:

GGGTGACTGT TAA 13

( 2 ) INFORMATION FOR SEQ ID NO:86:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:86:

GGGGGTGACT GT 12

( 2 ) INFORMATION FOR SEQ ID NO:87:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:87:

AGTTGGGGGG T 11

( 2 ) INFORMATION FOR SEQ ID NO:88:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:88:

TGTGTTAGTT GGG 13

( 2 ) INFORMATION FOR SEQ ID NO:89:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:89:

AAAATAATGT GTT 13

( 2 ) INFORMATION FOR SEQ ID NO:90:

( i ) SEQUENCE CHARACTERISTICS:
   ( A ) LENGTH: 12 base pairs
   ( B ) TYPE: nucleic acid
   ( C ) STRANDEDNESS: single
   ( D ) TOPOLOGY: linear ( i i ) MOLECULE TYPE: DNA (probe)

( x i ) SEQUENCE DESCRIPTION: SEQ ID NO:90:

AGGGGAAAAT AA  12

( 2 ) INFORMATION FOR SEQ ID NO:91:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:91:

GGAGGGGAAA AT  12

( 2 ) INFORMATION FOR SEQ ID NO:92:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:92:

GGAAATTTTT TG  12

( 2 ) INFORMATION FOR SEQ ID NO:93:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:93:

GGTGGAAATT TT  12

( 2 ) INFORMATION FOR SEQ ID NO:94:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:94:

GGTTTGGTGG A  11

( 2 ) INFORMATION FOR SEQ ID NO:95:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:95:

GAGGGGGGGT T  11

( 2 ) INFORMATION FOR SEQ ID NO:96:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:96:

GCGGGGGAGG  10

( 2 ) INFORMATION FOR SEQ ID NO:97:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:97:

CAGAAGCGGG G  11

( 2 ) INFORMATION FOR SEQ ID NO:98:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:98:

GTAGGCCAGA AG  12

( 2 ) INFORMATION FOR SEQ ID NO:99:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:99:

GTGCTGTAGG CC  12

( 2 ) INFORMATION FOR SEQ ID NO:100:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:100:

TGTTTAAGTG CTG 13

(2) INFORMATION FOR SEQ ID NO:101:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:101:

TGTGTTTAAG TGC 13

(2) INFORMATION FOR SEQ ID NO:102:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:102:

GCAGAGATGT GTT 13

(2) INFORMATION FOR SEQ ID NO:103:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:103:

TTTGGCAGAG AT 12

(2) INFORMATION FOR SEQ ID NO:104:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:104:

GGGGTTTGGC A 11

(2) INFORMATION FOR SEQ ID NO:105:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:105:

TGTTTTTGGG GT 12

(2) INFORMATION FOR SEQ ID NO:106:

( i ) SEQUENCE CHARACTERISTICS:
 ( A ) LENGTH: 12 base pairs
 ( B ) TYPE: nucleic acid
 ( C ) STRANDEDNESS: single
 ( D ) TOPOLOGY: linear ( i i ) MOLECULE TYPE: DNA (probe)

( x i ) SEQUENCE DESCRIPTION: SEQ ID NO:106:

TTTGTTTTTG GG 12

( 2 ) INFORMATION FOR SEQ ID NO:107:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:107:

GGGTTCTTTG TT 12

( 2 ) INFORMATION FOR SEQ ID NO:108:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:108:

GTGTTAGGGT TCT 13

( 2 ) INFORMATION FOR SEQ ID NO:109:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:109:

TTTAGTAAGT ATGT 14

( 2 ) INFORMATION FOR SEQ ID NO:110:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:110:

AACACACTTT AGT 13

( 2 ) INFORMATION FOR SEQ ID NO:111:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:111:

AATTAATTAA CACA 14

( 2 ) INFORMATION FOR SEQ ID NO:112:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:112:

AAGCATTAAT TAA 13

( 2 ) INFORMATION FOR SEQ ID NO:113:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:113:

GTCCTACAAG CAT 13

( 2 ) INFORMATION FOR SEQ ID NO:114:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:114:

TGTCCTACAA GCA 13

( 2 ) INFORMATION FOR SEQ ID NO:115:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:115:

ATTATTATGT CCT 13

( 2 ) INFORMATION FOR SEQ ID NO:116:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:116:

TTGTTATTAT TATG 14

( 2 ) INFORMATION FOR SEQ ID NO:117:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:117:

ATTCAAATTG TTA 13

( 2 ) INFORMATION FOR SEQ ID NO:118:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:118:

GCAGACATTC AAA 13

( 2 ) INFORMATION FOR SEQ ID NO:119:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:119:

GCTGTGCAGA CA 12

( 2 ) INFORMATION FOR SEQ ID NO:120:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:120:

AAAGTGGCTG TG 12

( 2 ) INFORMATION FOR SEQ ID NO:121:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:121:

TGTGTGGAAA GTG 13

( 2 ) INFORMATION FOR SEQ ID NO:122:

( i ) SEQUENCE CHARACTERISTICS:
   ( A ) LENGTH: 13 base pairs
   ( B ) TYPE: nucleic acid
   ( C ) STRANDEDNESS: single
   ( D ) TOPOLOGY: linear ( i i ) MOLECULE TYPE: DNA (probe)

( x i ) SEQUENCE DESCRIPTION: SEQ ID NO:122:

GATGTCTGTG TGG 13

( 2 ) INFORMATION FOR SEQ ID NO:123:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:123:

ATGATGTCTG TGT 13

( 2 ) INFORMATION FOR SEQ ID NO:124:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:124:

TTTTGTTATG ATG 13

( 2 ) INFORMATION FOR SEQ ID NO:125:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:125:

TTTTTGTTA TGA 13

( 2 ) INFORMATION FOR SEQ ID NO:126:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (probe)

( x i ) SEQUENCE DESCRIPTION: SEQ ID NO:126:

ATAGGGTGCT CC 12

( 2 ) INFORMATION FOR SEQ ID NO:127:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear (i i) MOLECULE TYPE: DNA (probe)

(x i) SEQUENCE DESCRIPTION: SEQ ID NO:127:

GCGACATAGG GT                                                                                               12

(2) INFORMATION FOR SEQ ID NO:128:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:128:

TACTGCGACA TAG                                                                                              13

(2) INFORMATION FOR SEQ ID NO:129:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:129:

GACAGATACT GCG                                                                                              13

(2) INFORMATION FOR SEQ ID NO:130:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:130:

AATCAAAGAC AGA                                                                                              13

(2) INFORMATION FOR SEQ ID NO:131:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:131:

AGGAATCAAA GAC                                                                                              13

(2) INFORMATION FOR SEQ ID NO:132:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:132:

TGAGGCAGGA AT 12

( 2 ) INFORMATION FOR SEQ ID NO:133:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:133:

AGGATGAGGC AG 12

( 2 ) INFORMATION FOR SEQ ID NO:134:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:134:

AAATAATAGG ATG 13

( 2 ) INFORMATION FOR SEQ ID NO:135:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:135:

GCGATAAATA AT 12

( 2 ) INFORMATION FOR SEQ ID NO:136:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:136:

TAGGATGCGA TA 12

( 2 ) INFORMATION FOR SEQ ID NO:137:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:137:

GTAGGATGCG AT 12

( 2 ) INFORMATION FOR SEQ ID NO:138:

( i ) SEQUENCE CHARACTERISTICS:
　　　　( A ) LENGTH: 12 base pairs
　　　　( B ) TYPE: nucleic acid
　　　　( C ) STRANDEDNESS: single
　　　　( D ) TOPOLOGY: linear ( i i ) MOLECULE TYPE: DNA (probe)

( x i ) SEQUENCE DESCRIPTION: SEQ ID NO:138:

TTGAACGTAG GA						12

( 2 ) INFORMATION FOR SEQ ID NO:139:

( i ) SEQUENCE CHARACTERISTICS:
　　　　　　　　( A ) LENGTH: 13 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (probe)

( x i ) SEQUENCE DESCRIPTION: SEQ ID NO:139:

AATATTGAAC GTA						13

( 2 ) INFORMATION FOR SEQ ID NO:140:

( i ) SEQUENCE CHARACTERISTICS:
　　　　　　　　( A ) LENGTH: 13 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (probe)

( x i ) SEQUENCE DESCRIPTION: SEQ ID NO:140:

GCCTGTAATA TTG						13

( 2 ) INFORMATION FOR SEQ ID NO:141:

( i ) SEQUENCE CHARACTERISTICS:
　　　　　　　　( A ) LENGTH: 12 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (probe)

( x i ) SEQUENCE DESCRIPTION: SEQ ID NO:141:

TGTTCGCCTG TA						12

( 2 ) INFORMATION FOR SEQ ID NO:142:

( i ) SEQUENCE CHARACTERISTICS:
　　　　　　　　( A ) LENGTH: 12 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (probe)

( x i ) SEQUENCE DESCRIPTION: SEQ ID NO:142:

GTATGTTCGC CT						12

( 2 ) INFORMATION FOR SEQ ID NO:143:

( i ) SEQUENCE CHARACTERISTICS:
　　　　　　　　( A ) LENGTH: 12 base pairs
　　　　　　　　( B ) TYPE: nucleic acid
　　　　　　　　( C ) STRANDEDNESS: single
　　　　　　　　( D ) TOPOLOGY: linear (i i) MOLECULE TYPE: DNA (probe)

(x i) SEQUENCE DESCRIPTION: SEQ ID NO:143:

CTCCCGTGAG TG    12

(2) INFORMATION FOR SEQ ID NO:144:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:144:

GAGAGCTCCC GT    12

(2) INFORMATION FOR SEQ ID NO:145:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:145:

ATGGAGAGCT CC    12

(2) INFORMATION FOR SEQ ID NO:146:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:146:

AATGCATGGA GA    12

(2) INFORMATION FOR SEQ ID NO:147:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:147:

ATACCAAATG CA    12

(2) INFORMATION FOR SEQ ID NO:148:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:148:

GACGAAAATA CCA 13

( 2 ) INFORMATION FOR SEQ ID NO:149:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:149:

CCCAGACGAA A 11

( 2 ) INFORMATION FOR SEQ ID NO:150:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:150:

TACCCCCAG A 11

( 2 ) INFORMATION FOR SEQ ID NO:151:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:151:

TGCATACCCCC 11

( 2 ) INFORMATION FOR SEQ ID NO:152:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:152:

TCGCGTGCAT AC 12

( 2 ) INFORMATION FOR SEQ ID NO:153:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:153:

GACTATCGCG TG 12

( 2 ) INFORMATION FOR SEQ ID NO:154:

(    i    ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear (    i i    ) MOLECULE TYPE: DNA (probe)

(    x i    ) SEQUENCE DESCRIPTION: SEQ ID NO:154:

ATGACTATCG CG                                              12

( 2 ) INFORMATION FOR SEQ ID NO:155:

(    i    ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear (    i i    ) MOLECULE TYPE: DNA (probe)

(    x i    ) SEQUENCE DESCRIPTION: SEQ ID NO:155:

CTCGCAATGA CT                                              12

( 2 ) INFORMATION FOR SEQ ID NO:156:

(    i    ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear (    i i    ) MOLECULE TYPE: DNA (probe)

(    x i    ) SEQUENCE DESCRIPTION: SEQ ID NO:156:

CGTCTCGCAA TG                                              12

( 2 ) INFORMATION FOR SEQ ID NO:157:

(    i    ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear (    i i    ) MOLECULE TYPE: DNA (probe)

(    x i    ) SEQUENCE DESCRIPTION: SEQ ID NO:157:

CTCCAGCGTC TC                                              12

( 2 ) INFORMATION FOR SEQ ID NO:158:

(    i    ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear (    i i    ) MOLECULE TYPE: DNA (probe)

(    x i    ) SEQUENCE DESCRIPTION: SEQ ID NO:158:

TCCGGCTCCA G                                               11

( 2 ) INFORMATION FOR SEQ ID NO:159:

(    i    ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:159:

GTGCTCCGGC T 11

( 2 ) INFORMATION FOR SEQ ID NO:160:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:160:

GACCCTGAAG TAG 13

( 2 ) INFORMATION FOR SEQ ID NO:161:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:161:

TTTATGACCC TGA 13

( 2 ) INFORMATION FOR SEQ ID NO:162:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:162:

TTTAGGCTTT ATG 13

( 2 ) INFORMATION FOR SEQ ID NO:163:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:163:

GCTATTTAGG CT 12

( 2 ) INFORMATION FOR SEQ ID NO:164:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:164:

TGGGCTATTT AG                                                    12

( 2 ) INFORMATION FOR SEQ ID NO:165:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:165:

ACGTGTGGGC TA                                                    12

( 2 ) INFORMATION FOR SEQ ID NO:166:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:166:

AGGGGAACGT GT                                                    12

( 2 ) INFORMATION FOR SEQ ID NO:167:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:167:

TTTAAGGGA AC                                                     12

( 2 ) INFORMATION FOR SEQ ID NO:168:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:168:

ATGTCTTATT TAAG                                                  14

( 2 ) INFORMATION FOR SEQ ID NO:169:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:169:

CATCGTGATG TCT                                                   13

( 2 ) INFORMATION FOR SEQ ID NO:170:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:170:

TCCATCGTGA TG             12

( 2 ) INFORMATION FOR SEQ ID NO:171:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:171:

GATGATCCAT CG             12

( 2 ) INFORMATION FOR SEQ ID NO:172:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:172:

AGACCTGATG ATC            13

( 2 ) INFORMATION FOR SEQ ID NO:173:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:173:

GGGTGATAGA CCT            13

( 2 ) INFORMATION FOR SEQ ID NO:174:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:174:

ATAGGGTGAT AGA            13

( 2 ) INFORMATION FOR SEQ ID NO:175:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:175:

TGGTTAATAG GG 12

( 2 ) INFORMATION FOR SEQ ID NO:176:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:176:

GTGAGTGGTT AAT 13

( 2 ) INFORMATION FOR SEQ ID NO:177:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:177:

TGTGCGGGAT AT 12

( 2 ) INFORMATION FOR SEQ ID NO:178:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:178:

ACTCTTGTGC GG 12

( 2 ) INFORMATION FOR SEQ ID NO:179:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:179:

TAGCACTCTT GTG 13

( 2 ) INFORMATION FOR SEQ ID NO:180:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:180:

GGAGAGTAGC ACT  13

( 2 ) INFORMATION FOR SEQ ID NO:181:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:181:

GCGAGGAGAG TA  12

( 2 ) INFORMATION FOR SEQ ID NO:182:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:182:

CGGAGCGAGG A  11

( 2 ) INFORMATION FOR SEQ ID NO:183:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:183:

GGCCCGGAGC  10

( 2 ) INFORMATION FOR SEQ ID NO:184:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:184:

TTATGGGCCC G  11

( 2 ) INFORMATION FOR SEQ ID NO:185:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:185:

AGTGTTATGG GC  12

( 2 ) INFORMATION FOR SEQ ID NO:186:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:186:

TACCCCCAAG TG 12

( 2 ) INFORMATION FOR SEQ ID NO:187:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:187:

TTTAGCTACC CC 12

( 2 ) INFORMATION FOR SEQ ID NO:188:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:188:

TTCACTTTAG CTA 13

( 2 ) INFORMATION FOR SEQ ID NO:189:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:189:

TACAGTTCAC TTT 13

( 2 ) INFORMATION FOR SEQ ID NO:190:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:190:

TCGAGATACA GTT 13

( 2 ) INFORMATION FOR SEQ ID NO:191:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear (i i) MOLECULE TYPE: DNA (probe)

(x i) SEQUENCE DESCRIPTION: SEQ ID NO:191:

CAGATGTCGA GAT 13

(2) INFORMATION FOR SEQ ID NO:192:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:192:

AGGAACCAGA TG 12

(2) INFORMATION FOR SEQ ID NO:193:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:193:

GAAGTAGGAA CCA 13

(2) INFORMATION FOR SEQ ID NO:194:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:194:

GACTGTAATG TGC 13

(2) INFORMATION FOR SEQ ID NO:195:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:195:

GGGATTTGAC TGT 13

(2) INFORMATION FOR SEQ ID NO:196:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:196:

AGGGATTTGA CT 12

( 2 ) INFORMATION FOR SEQ ID NO:197:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:197:

ACGAGAAGGG AT 12

( 2 ) INFORMATION FOR SEQ ID NO:198:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:198:

TGGGGACGAG AA 12

( 2 ) INFORMATION FOR SEQ ID NO:199:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:199:

ATCCATGGGG AC 12

( 2 ) INFORMATION FOR SEQ ID NO:200:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:200:

GGTCATCCAT GG 12

( 2 ) INFORMATION FOR SEQ ID NO:201:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:201:

AGGGGGGTCA T 11

( 2 ) INFORMATION FOR SEQ ID NO:202:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:202:

TATCTGAGGG GG     12

( 2 ) INFORMATION FOR SEQ ID NO:203:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:203:

ACCCCTATCT GA     12

( 2 ) INFORMATION FOR SEQ ID NO:204:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:204:

AGGGACCCCT A     11

( 2 ) INFORMATION FOR SEQ ID NO:205:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:205:

TGGTCAAGGG AC     12

( 2 ) INFORMATION FOR SEQ ID NO:206:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:206:

GGATGGTGGT CA     12

( 2 ) INFORMATION FOR SEQ ID NO:207:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear (i i) MOLECULE TYPE: DNA (probe)

(x i) SEQUENCE DESCRIPTION: SEQ ID NO:207:

AGGATGGTGG TC  12

(2) INFORMATION FOR SEQ ID NO:208:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:208:

ACACGGAGGA TG  12

(2) INFORMATION FOR SEQ ID NO:209:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:209:

TGATTTACAC GG  12

(2) INFORMATION FOR SEQ ID NO:210:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:210:

GGGATATTGA TTT  13

(2) INFORMATION FOR SEQ ID NO:211:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:211:

GTGGCATTTG GA  12

(2) INFORMATION FOR SEQ ID NO:212:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:212:

AGGGGTGGCA T                                                                                     11

( 2 ) INFORMATION FOR SEQ ID NO:213:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:213:

GGTGAGGGGT G                                                                                     11

( 2 ) INFORMATION FOR SEQ ID NO:214:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:214:

AGTGGGTGAG GG                                                                                    12

( 2 ) INFORMATION FOR SEQ ID NO:215:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:215:

GTATCCTAGT GGG                                                                                   13

( 2 ) INFORMATION FOR SEQ ID NO:216:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:216:

TTTGTTGGTA TCC                                                                                   13

( 2 ) INFORMATION FOR SEQ ID NO:217:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:217:

GTAGGTTTGT TGG                                                                                   13

( 2 ) INFORMATION FOR SEQ ID NO:218:

(i) SEQUENCE CHARACTERISTICS:
  (A) LENGTH: 12 base pairs
  (B) TYPE: nucleic acid
  (C) STRANDEDNESS: single
  (D) TOPOLOGY: linear (ii) MOLECULE TYPE: DNA (probe)

(xi) SEQUENCE DESCRIPTION: SEQ ID NO:218:

TGGGTAGGTT TG                                                        12

(2) INFORMATION FOR SEQ ID NO:219:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:219:

TAAGGGTGGG TA                                                        12

(2) INFORMATION FOR SEQ ID NO:220:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:220:

GTACTGTTAA GGG                                                       13

(2) INFORMATION FOR SEQ ID NO:221:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:221:

TGTACTATGT ACTG                                                      14

(2) INFORMATION FOR SEQ ID NO:222:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:222:

GGCTTTATGT ACT                                                       13

(2) INFORMATION FOR SEQ ID NO:223:

(i) SEQUENCE CHARACTERISTICS:
    (A) LENGTH: 12 base pairs
    (B) TYPE: nucleic acid
    (C) STRANDEDNESS: single
    (D) TOPOLOGY: linear ( i i ) MOLECULE TYPE: DNA (probe)

( x i ) SEQUENCE DESCRIPTION: SEQ ID NO:223:

AAATGGCTTT AT  12

( 2 ) INFORMATION FOR SEQ ID NO:224:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:224:

GGTAAATGGC TT  12

( 2 ) INFORMATION FOR SEQ ID NO:225:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:225:

TGTACGGTAA ATG  13

( 2 ) INFORMATION FOR SEQ ID NO:226:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:226:

GTGCTAATGT ACG  13

( 2 ) INFORMATION FOR SEQ ID NO:227:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:227:

TAATGTGCTA ATG  13

( 2 ) INFORMATION FOR SEQ ID NO:228:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:228:

CATGGGGAGG G 11

(2) INFORMATION FOR SEQ ID NO:229:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:229:

TGTAAGCATG GG 12

(2) INFORMATION FOR SEQ ID NO:230:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:230:

TTGCTTGTAA GCA 13

(2) INFORMATION FOR SEQ ID NO:231:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:231:

TGTACTTGCT TGT 13

(2) INFORMATION FOR SEQ ID NO:232:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:232:

TTGCTGTACT TGC 13

(2) INFORMATION FOR SEQ ID NO:233:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:233:

GGTTGATTGC TG 12

(2) INFORMATION FOR SEQ ID NO:234:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:234:

TTGAGGGTTG AT     12

( 2 ) INFORMATION FOR SEQ ID NO:235:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:235:

GTGATAGTTG AGG     13

( 2 ) INFORMATION FOR SEQ ID NO:236:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:236:

TTGATGTGTG ATA     13

( 2 ) INFORMATION FOR SEQ ID NO:237:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:237:

TGCAGTTGAT GTG     13

( 2 ) INFORMATION FOR SEQ ID NO:238:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:238:

TGGAGTTGCA GT     12

( 2 ) INFORMATION FOR SEQ ID NO:239:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:239:

ATTTGGAGTT GC                                                                                    1 2

( 2 ) INFORMATION FOR SEQ ID NO:240:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:240:

TACCGTACAA TAT                                                                                   1 3

( 2 ) INFORMATION FOR SEQ ID NO:241:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:241:

TGGTACCGTA CAA                                                                                   1 3

( 2 ) INFORMATION FOR SEQ ID NO:242:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:242:

TATTTATGGT ACC                                                                                   1 3

( 2 ) INFORMATION FOR SEQ ID NO:243:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:243:

GGTCAAGTAT TTA                                                                                   1 3

( 2 ) INFORMATION FOR SEQ ID NO:244:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:244:

TACAGGTGGT CAA 13

( 2 ) INFORMATION FOR SEQ ID NO:245:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:245:

ATGTACTACA GGT 13

( 2 ) INFORMATION FOR SEQ ID NO:246:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:246:

GGTTTTTATG TAC 13

( 2 ) INFORMATION FOR SEQ ID NO:247:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:247:

GGATTGGGTT TT 12

( 2 ) INFORMATION FOR SEQ ID NO:248:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:248:

TGTAGGATTG GG 12

( 2 ) INFORMATION FOR SEQ ID NO:249:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:249:

GTTTTGATGT AGG 13

( 2 ) INFORMATION FOR SEQ ID NO:250:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:250:

GGGTTTTGAT GT 12

( 2 ) INFORMATION FOR SEQ ID NO:251:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:251:

GGAGGGGGTT T 11

( 2 ) INFORMATION FOR SEQ ID NO:252:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:252:

GTCAATACTT GGG 13

( 2 ) INFORMATION FOR SEQ ID NO:253:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:253:

GGGTGAGTCA ATA 13

( 2 ) INFORMATION FOR SEQ ID NO:254:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:254:

TGGGTGAGTC AA 12

( 2 ) INFORMATION FOR SEQ ID NO:255:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:255:

TGTTGATGGG TG                     12

( 2 ) INFORMATION FOR SEQ ID NO:256:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (probe)

( x i ) SEQUENCE DESCRIPTION: SEQ ID NO:256:

CGGTTGTTGA TG                     12

( 2 ) INFORMATION FOR SEQ ID NO:257:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (probe)

( x i ) SEQUENCE DESCRIPTION: SEQ ID NO:257:

ACATAGCGGT TG                     12

( 2 ) INFORMATION FOR SEQ ID NO:258:

( i ) SEQUENCE CHARACTERISTICS:
                ( A ) LENGTH: 13 base pairs
                ( B ) TYPE: nucleic acid
                ( C ) STRANDEDNESS: single
                ( D ) TOPOLOGY: linear ( i i ) MOLECULE TYPE: DNA (probe)

( x i ) SEQUENCE DESCRIPTION: SEQ ID NO:258:

GAAAATACAT AGC                    13

( 2 ) INFORMATION FOR SEQ ID NO:259:

( i ) SEQUENCE CHARACTERISTICS:
                ( A ) LENGTH: 13 base pairs
                ( B ) TYPE: nucleic acid
                ( C ) STRANDEDNESS: single
                ( D ) TOPOLOGY: linear ( i i ) MOLECULE TYPE: DNA (probe)

( x i ) SEQUENCE DESCRIPTION: SEQ ID NO:259:

AATGTACGAA AAT                    13

( 2 ) INFORMATION FOR SEQ ID NO:260:

( i ) SEQUENCE CHARACTERISTICS:
                ( A ) LENGTH: 13 base pairs
                ( B ) TYPE: nucleic acid
                ( C ) STRANDEDNESS: single
                ( D ) TOPOLOGY: linear ( i i ) MOLECULE TYPE: DNA (probe)

( x i ) SEQUENCE DESCRIPTION: SEQ ID NO:260:

GCAGTAATGT ACG                                              13

( 2 ) INFORMATION FOR SEQ ID NO:261:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:261:

TGGCTGGCAG TA                                               12

( 2 ) INFORMATION FOR SEQ ID NO:262:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:262:

TCATGGTGGC TG                                               12

( 2 ) INFORMATION FOR SEQ ID NO:263:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:263:

ACAATATTCA TGG                                              13

( 2 ) INFORMATION FOR SEQ ID NO:264:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:264:

TAGAATCTTA GCT                                              13

( 2 ) INFORMATION FOR SEQ ID NO:265:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:265:

TTTAAATTAG AAT                                              13

( 2 ) INFORMATION FOR SEQ ID NO:266:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:266:

GAATAAGTTT AAA 13

(2) INFORMATION FOR SEQ ID NO:267:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:267:

GAACAGAGAA TAA 13

(2) INFORMATION FOR SEQ ID NO:268:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:268:

AAAGAACAGA GAA 13

(2) INFORMATION FOR SEQ ID NO:269:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:269:

CCCATGAAAG AA 12

(2) INFORMATION FOR SEQ ID NO:270:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:270:

TTCCCCATGA AA 12

(2) INFORMATION FOR SEQ ID NO:271:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (i i) MOLECULE TYPE: DNA (probe)

(x i) SEQUENCE DESCRIPTION: SEQ ID NO:271:

ATCTGCTTCC CC 12

(2) INFORMATION FOR SEQ ID NO:272:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:272:

CAAATCTGCT TC 12

(2) INFORMATION FOR SEQ ID NO:273:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:273:

GGTACCCAAA TC 12

(2) INFORMATION FOR SEQ ID NO:274:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:274:

GGTGGTACCC AA 12

(2) INFORMATION FOR SEQ ID NO:275:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:275:

TACTTGGGTG GT 12

(2) INFORMATION FOR SEQ ID NO:276:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:276:

TGGAAAAAGG TT                                                                    12

( 2 ) INFORMATION FOR SEQ ID NO:277:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:277:

GTCCTTGGAA AA                                                                    12

( 2 ) INFORMATION FOR SEQ ID NO:278:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:278:

ATTTGTCCTT GG                                                                    12

( 2 ) INFORMATION FOR SEQ ID NO:279:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:279:

CTCTGATTTG TCC                                                                   13

( 2 ) INFORMATION FOR SEQ ID NO:280:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:280:

TTTTTCTCTG ATT                                                                   13

( 2 ) INFORMATION FOR SEQ ID NO:281:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:281:

TAAAGACTTT TTC                                                                   13

( 2 ) INFORMATION FOR SEQ ID NO:282:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:282:

GTGGAGTTAA AGA      13

( 2 ) INFORMATION FOR SEQ ID NO:283:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:283:

TGGTGGAGTT AAA      13

( 2 ) INFORMATION FOR SEQ ID NO:284:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:284:

TGCTAATGGT GG      12

( 2 ) INFORMATION FOR SEQ ID NO:285:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:285:

TTGGGTGCTA AT      12

( 2 ) INFORMATION FOR SEQ ID NO:286:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:286:

TAGCTTTGGG TG      12

( 2 ) INFORMATION FOR SEQ ID NO:287:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear (  i  i  ) MOLECULE TYPE: DNA (probe)

(  x  i  ) SEQUENCE DESCRIPTION: SEQ ID NO:287:

TCTTAGCTTT GG                                                                                                                    12

( 2 ) INFORMATION FOR SEQ ID NO:288:

(  i  ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (  i  i  ) MOLECULE TYPE: DNA (probe)

(  x  i  ) SEQUENCE DESCRIPTION: SEQ ID NO:288:

CACTTGTGCC CTGACTTTCA AC                                                                                                         22

( 2 ) INFORMATION FOR SEQ ID NO:289:

(  i  ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear (  i  i  ) MOLECULE TYPE: DNA (probe)

(  x  i  ) SEQUENCE DESCRIPTION: SEQ ID NO:289:

ATGCAATTAA CCCTCACTAA AGGGAGACAC TTGTGCCCTG ACTTTCAAC                                                                             49

( 2 ) INFORMATION FOR SEQ ID NO:290:

(  i  ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (  i  i  ) MOLECULE TYPE: DNA (probe)

(  x  i  ) SEQUENCE DESCRIPTION: SEQ ID NO:290:

GACCCTGGGC AACCAGCCCT GTCGT                                                                                                      25

( 2 ) INFORMATION FOR SEQ ID NO:291:

(  i  ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear (  i  i  ) MOLECULE TYPE: DNA (probe)

(  x  i  ) SEQUENCE DESCRIPTION: SEQ ID NO:291:

TAATACGACT CACTATAGGG AGGACCCTGG GCAACCAGCC CTGTCGT                                                                               47

( 2 ) INFORMATION FOR SEQ ID NO:292:

(  i  ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (  i  i  ) MOLECULE TYPE: DNA (probe)

(  x  i  ) SEQUENCE DESCRIPTION: SEQ ID NO:292:

```
GTAGAATTCT GTTGACTCAG ATTGG                                              25
```

(2) INFORMATION FOR SEQ ID NO:293:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:293:

```
AAATCCATAC AATACTCCAG TATTTGC                                            27
```

(2) INFORMATION FOR SEQ ID NO:294:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:294:

```
GATAAGCTTG GGCCTTATCT ATTCCAT                                            27
```

(2) INFORMATION FOR SEQ ID NO:295:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (probe)

(xi) SEQUENCE DESCRIPTION: SEQ ID NO:295:

```
ACCCATCCAA AGGAATGGAG GTTCTTTC                                           28
```

(2) INFORMATION FOR SEQ ID NO:296:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (oligonucleotide)

(xi) SEQUENCE DESCRIPTION: SEQ ID NO:296:

```
AGCCTAGCTG AA                                                            12
```

(2) INFORMATION FOR SEQ ID NO:297:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (oligonucleotide)

(xi) SEQUENCE DESCRIPTION: SEQ ID NO:297:

```
TCGGATCGAC TT                                                            12
```

(2) INFORMATION FOR SEQ ID NO:298:

( i ) SEQUENCE CHARACTERISTICS:
 ( A ) LENGTH: 22 base pairs
 ( B ) TYPE: nucleic acid
 ( C ) STRANDEDNESS: single
 ( D ) TOPOLOGY: linear ( i i ) MOLECULE TYPE: DNA (probe)

( x i ) SEQUENCE DESCRIPTION: SEQ ID NO:298:

CGGAATTAAC CCTCACTAAA GG 22

( 2 ) INFORMATION FOR SEQ ID NO:299:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:299:

AATTAACCCT CACTAAAGGG AG 22

( 2 ) INFORMATION FOR SEQ ID NO:300:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:300:

TAATACGACT CACTATAGGG AG 22

( 2 ) INFORMATION FOR SEQ ID NO:301:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:301:

ATTTAGGTGA CACTATAGAA 20

( 2 ) INFORMATION FOR SEQ ID NO:302:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: DNA (probe)

( x i ) SEQUENCE DESCRIPTION: SEQ ID NO:302:

GATNATATTT 10

( 2 ) INFORMATION FOR SEQ ID NO:303:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear (i i) MOLECULE TYPE: DNA (probe)

(x i) SEQUENCE DESCRIPTION: SEQ ID NO:303:

AGANGATATT  10

(2) INFORMATION FOR SEQ ID NO:304:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:304:

AAGNTGATAT  10

(2) INFORMATION FOR SEQ ID NO:305:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:305:

AAANATGATA  10

(2) INFORMATION FOR SEQ ID NO:306:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:306:

CAANGATGAT  10

(2) INFORMATION FOR SEQ ID NO:307:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:307:

CCANAGATGA  10

(2) INFORMATION FOR SEQ ID NO:308:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:308:

ACCNAAGATG                                                                     10

( 2 ) INFORMATION FOR SEQ ID NO:309:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:309:

CACNAAAGAT                                                                     10

( 2 ) INFORMATION FOR SEQ ID NO:310:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:310:

AGAAACNACA                                                                     10

( 2 ) INFORMATION FOR SEQ ID NO:311:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:311:

ATTTCATTCT GTATTG                                                              16

( 2 ) INFORMATION FOR SEQ ID NO:312:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:312:

CCGACTGCAG TCGTTA                                                              16

( 2 ) INFORMATION FOR SEQ ID NO:313:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:313:

CCGACTGCAG TCGTT                                                               15

( 2 ) INFORMATION FOR SEQ ID NO:314:

-continued ( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:314:

CCGACTACAG TCGTT 15

( 2 ) INFORMATION FOR SEQ ID NO:315:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:315:

CCGACTCCAG TCGTT 15

( 2 ) INFORMATION FOR SEQ ID NO:316:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:316:

CCGACTTCAG TCGTT 15

( 2 ) INFORMATION FOR SEQ ID NO:317:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:317:

GTAATTTCTT TTATAGTAGA AACCACAAAG GATAC 35

( 2 ) INFORMATION FOR SEQ ID NO:318:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:318:

CATTAAAGAA AATATCATCT TTGGTGTTTC CTATG 35

( 2 ) INFORMATION FOR SEQ ID NO:319:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear (i i) MOLECULE TYPE: DNA (oligonucleotide)

(x i) SEQUENCE DESCRIPTION: SEQ ID NO:319:

CATTAAAGAA AATATCATTG GTGTTTCCTA TG 32

(2) INFORMATION FOR SEQ ID NO:320:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:320:

CATTAAAGAA AATATCAT 18

(2) INFORMATION FOR SEQ ID NO:321:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (oligonucleotide)

(x i) SEQUENCE DESCRIPTION: SEQ ID NO:321:

TATTAAAGAA AATATCATCT TTGGTGTTTC CTATC 35

(2) INFORMATION FOR SEQ ID NO:322:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (oligonucleotide)

(x i) SEQUENCE DESCRIPTION: SEQ ID NO:322:

CCTTAAAGAA AATATCATCT TTGGTGTTTC CTAAA 35

(2) INFORMATION FOR SEQ ID NO:323:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (oligonucletide)

(x i) SEQUENCE DESCRIPTION: SEQ ID NO:323:

CTTTAAAGAA AATAAAAAAA TTGGTGTTTC CTAAA 35

(2) INFORMATION FOR SEQ ID NO:324:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:324:

GGAAGTCTCC CATTTTAATT 20

(2) INFORMATION FOR SEQ ID NO:325:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (probe)

(xi) SEQUENCE DESCRIPTION: SEQ ID NO:325:

CCTTCAGAGG GTAAAATTAA 20

(2) INFORMATION FOR SEQ ID NO:326:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (probe)

(xi) SEQUENCE DESCRIPTION: SEQ ID NO:326:

CCTTCAGAGK GTAAAATTAA 20

(2) INFORMATION FOR SEQ ID NO:327:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (probe)

(xi) SEQUENCE DESCRIPTION: SEQ ID NO:327:

CCTTCAGAGT GTAAAATTAA 20

(2) INFORMATION FOR SEQ ID NO:328:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (probe)

(xi) SEQUENCE DESCRIPTION: SEQ ID NO:328:

CCTTCAGAGG GTAAAATCA 19

(2) INFORMATION FOR SEQ ID NO:329:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (probe)

(xi) SEQUENCE DESCRIPTION: SEQ ID NO:329:

CCTTCAGAGG GTAAAATTA 19

(2) INFORMATION FOR SEQ ID NO:330:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:330:

```
GATTCAGAGT GTAAAATAC                                                    19
```

( 2 ) INFORMATION FOR SEQ ID NO:331:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:331:

```
AAAAAGAGT GTAAAATGA                                                     19
```

( 2 ) INFORMATION FOR SEQ ID NO:332:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:332:

```
CATTAAAGAA AATAACATCA TTGGTGTTTC CTATG                                  35
```

( 2 ) INFORMATION FOR SEQ ID NO:333:

( i ) SEQUENCE CHARACTERISTICS:
        ( A ) LENGTH: 648 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:333:

```
AACAAACCTA CCCACCCTTA ACAGTACATA GTACATAAAG CCATTTACCG TACATAGCAC        60
ATTACAGTCA AATCCCTTCT CGTCCCCATG GATGACCCCC CTCAGATAGG GGTCCCTTGA       120
CCACCATCCT CCGTGAAATC AATATCCCGC ACAAGAGTGC TACTCTCCTC GCTCCGGGCC       180
CATAACACTT GGGGGTAGCT AAAGTGAACT GTATCCGACA TCTGGTTCCT ACTTCAGGGT       240
CATAAGCCT  AAATAGCCCA CACGTTCCCC TTAAATAAGA CATCACGATG GATCACAGGT       300
CTATCACCCT ATTAACCACT CACGGGAGCT CTCCATGCAT TTGGTATTTT CGTCTGGGGG       360
GTATGCACGC GATAGCATTG CGAGACGCTG GAGCCGGAGC ACCCTATGTC GCAGTATCTG       420
TCTTTGATTC CTGCCTCATC CTATTATTTA TCGCACCTAC GTTCAATATT ACAGGCGAAC       480
ATACTTACTA AAGTGTGTTA ATTAATTAAT GCTTGTAGGA CATAATAATA ACAATTGAAT       540
GTCTGCACAG CCACTTTCCA CACAGACATC ATAACAAAAA ATTTCCACCA AACCCCCCCT       600
CTCCCCCGCT TCTGGCCACA GCACTTAAAC ACATCTCTGC CAAACCCC                   648
```

( 2 ) INFORMATION FOR SEQ ID NO:334:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:334:

GATGCTGAGG AG                                                                                              12

( 2 ) INFORMATION FOR SEQ ID NO:335:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (probe)

( x i ) SEQUENCE DESCRIPTION: SEQ ID NO:335:

CTCCTCCCCG GT                                                                                              12

( 2 ) INFORMATION FOR SEQ ID NO:336:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (probe)

( x i ) SEQUENCE DESCRIPTION: SEQ ID NO:336:

ACTCCTCCCC GG                                                                                              12

( 2 ) INFORMATION FOR SEQ ID NO:337:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (probe)

( x i ) SEQUENCE DESCRIPTION: SEQ ID NO:337:

GACTCCTCCC CG                                                                                              12

( 2 ) INFORMATION FOR SEQ ID NO:338:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (probe)

( x i ) SEQUENCE DESCRIPTION: SEQ ID NO:338:

CGACTCCTCC CC                                                                                              12

( 2 ) INFORMATION FOR SEQ ID NO:339:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (probe)

( x i ) SEQUENCE DESCRIPTION: SEQ ID NO:339:

ACGACTCCTC CC 12

( 2 ) INFORMATION FOR SEQ ID NO:340:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:340:

TACGACTCCT CC 12

( 2 ) INFORMATION FOR SEQ ID NO:341:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:341:

CTACGACTCC TC 12

( 2 ) INFORMATION FOR SEQ ID NO:342:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:342:

TCTACGACTC CT 12

( 2 ) INFORMATION FOR SEQ ID NO:343:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:343:

TTCTACGACT CC 12

( 2 ) INFORMATION FOR SEQ ID NO:344:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:344:

ATTCTACGAC TC 12

( 2 ) INFORMATION FOR SEQ ID NO:345:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:345:

TATTCTACGA CT 12

( 2 ) INFORMATION FOR SEQ ID NO:346:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:346:

CTATTCTACG AC 12

( 2 ) INFORMATION FOR SEQ ID NO:347:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:347:

CCTATTCTAC GA 12

( 2 ) INFORMATION FOR SEQ ID NO:348:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:348:

TCCTCCCCGG 10

( 2 ) INFORMATION FOR SEQ ID NO:349:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:349:

CTCCTCCCCG 10

( 2 ) INFORMATION FOR SEQ ID NO:350:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (probe)

( x i ) SEQUENCE DESCRIPTION: SEQ ID NO:350:

A C T C C T C C C C           10

( 2 ) INFORMATION FOR SEQ ID NO:351:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:351:

G A C T C C T C C C           10

( 2 ) INFORMATION FOR SEQ ID NO:352:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:352:

C G A C T C C T C C           10

( 2 ) INFORMATION FOR SEQ ID NO:353:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:353:

A C G A C T C C T C           10

( 2 ) INFORMATION FOR SEQ ID NO:354:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:354:

T A C G A C T C C T           10

( 2 ) INFORMATION FOR SEQ ID NO:355:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear (i i) MOLECULE TYPE: DNA (probe)

(x i) SEQUENCE DESCRIPTION: SEQ ID NO:355:

CTACGACTCC 10

(2) INFORMATION FOR SEQ ID NO:356:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:356:

TCTACGACTC 10

(2) INFORMATION FOR SEQ ID NO:357:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:357:

TTCTACGACT 10

(2) INFORMATION FOR SEQ ID NO:358:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:358:

ATTCTACGAC 10

(2) INFORMATION FOR SEQ ID NO:359:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (probe)

(x i) SEQUENCE DESCRIPTION: SEQ ID NO:359:

TATTCTACGA 10

(2) INFORMATION FOR SEQ ID NO:360:

(i) SEQUENCE CHARACTERISTICS:
        (A) LENGTH: 184 base pairs
        (B) TYPE: nucleic acid
        (C) STRANDEDNESS: single
        (D) TOPOLOGY: linear (i i) MOLECULE TYPE: DNA (oligonucleotide)

(x i) SEQUENCE DESCRIPTION: SEQ ID NO:360:

| | | | | | | |
|---|---|---|---|---|---|---|
| TACTCCCCTG | CCCTCAACAA | GATGTTTTGC | CAACTGGCCA | AGACCTGCCC | TGTGCAGCWG | 60 |
| KGGGWWGATT | CCACACCCCC | GCCCGGCACC | CGCGTCCGCG | CCATGGCCAT | CTACAAGCAG | 120 |
| TCACAGCACA | TGACGGAGGW | WGKGAGGCGC | TGCCCCACC | ATGAGCGCYG | CYCAGATAGC | 180 |
| SAYG | | | | | | 184 |

We claim:

1. An array of oligonucleotide probes immobilized on a solid support, said array having at least 100 probes and no more than 100,000 different oligonucleotide probes 9 to 20 nucleotides in length occupying separate known sites in said array, said oligonucleotide probes comprising at least four sets of probes: (1) a first set that is exactly complementary to a reference sequence and comprises probes that completely span the reference sequence and, relative to the reference sequence, overlap one another in sequence; and (2) three additional sets of probes, each of which is identical to said first set of probes but for at least one different nucleotide, which different nucleotide is located in the same position in each of the three additional sets but which is a different nucleotide in each set.

2. The array of claim 1, further comprising a fourth additional set of probes, which fourth additional set is identical to probes in the first set.

3. The array of claim 1, wherein said reference sequence is a double-stranded nucleic acid and probes complementary to both strands of said reference are in said array.

4. The array of claim 1, wherein said probes are 12 to 17 nucleotides in length.

5. The array of claim 4, wherein said probes are 15 nucleotides in length and attached by a covalent linkage to a site on a 3'-end of said probes, and said different nucleotide is located at position 7, relative to the 3'-end of said probes.

6. The array of claim 1, wherein said reference sequence is exon 10 of a CFTR gene, and said array has between 1000 and 100,000 oligonucleotide probes 10 to 18 nucleotides in length.

7. The array of claim 6, wherein said array comprises a set of probes comprising a specific nucleotide sequence selected from the group of sequences consisting of:
3'-TTTATAXTAG (SEQ ID. NO:302);
3'-TTATAGXAGA (SEQ ID. NO:303);
3'-TATAGTXGAA (SEQ ID. NO:304);
3'-ATAGTAXAAA (SEQ ID. NO:305);
3'-TAGTAGXAAC (SEQ ID. NO:306);
3'-AGTAGAXACC (SEQ ID. NO:307);
3'-GTAGAAXCCA (SEQ ID. NO:308);
3'-TAGAAAXCAC (SEQ ID. NO:309); and
3'-AGAAACXACA (SEQ ID. NO:310); wherein each set comprises 4 probes, and X is individually A, G, C, and T for each set.

8. The array of claim 6, wherein said group of sequences consists of:
3'-TTTATAXTAGAAACC (SEQ ID. NO:9);
3'-TTATAGXAGAAACCA (SEQ ID. NO:10);
3'-TATAGTXGAAACCAC (SEQ ID. NO:11);
3'-ATAGTAXAAACCACA (SEQ ID. NO:12);
3'-TAGTAGXAACCACAA (SEQ ID. NO:13);
3'-AGTAGAXACCACAAA (SEQ ID. No:14);
3'-GTAGAAXCCACAAAG (SEQ ID. NO:15);
3'-TAGAAAXCACAAAGG (SEQ ID. NO:16); and
3'-AGAAACXACAAAGGA (SEQ ID. NO:17); wherein each set comprises 4 probes, and X is individually A, G, C, and T for each set.

9. The array of claim 1, wherein said reference sequence is a sequence of a D-loop region of human mitochondrial DNA.

10. The array of claim 9, wherein said probes are 15 nucleotides in length, and said array comprises a first set of probes exactly complementary to a sequence contained in a sequence bounded by positions 16280 to 356 of the reference sequence and four additional sets of probes identical to said first set but for position 7, relative to a 3'-end of a probe, which 3'-end is covalently attached to the substrate, where, for each of the four additional probe sets, a different nucleotide is located, such that, for each probe in said first set, there is an identical probe in one of the four additional sets, and such that the array has between 2500 and 100,000 oligonucleotide probes.

11. The array of claim 1, wherein said reference sequence is a sequence from an exon of a human p53 gene.

12. The array of claim 11, wherein said reference sequence comprises at least a 60 nucleotide contiguous sequence from exon 6 of a p53 gene.

13. The array of claim 11, wherein said reference sequence is exon 5 of a p53 gene, said probes are 17 nucleotides long, and said array comprises a first set of probes exactly complementary to said sequence and at least three additional sets of probes, each set comprising probes identical to said first set but for a nucleotide at position 7, relative to a 3'-end of a probe, which 3'-end is covalently attached to the substrate, which nucleotide is different from a nucleotide at this position in a corresponding probe of said first set.

14. The array of claim 1, wherein said probes are oligodeoxyribonucleotides.

15. The array of claim 1, wherein said array has between 10,000 and 100,000 probes.

16. The array of claim 1, wherein the reference sequence is from a human immunodeficiency virus.

17. The array of claim 16, wherein the reference sequence is from a reverse transcriptase gene of the human immunodeficiency virus.

18. The array of claim 1, wherein said probes are immobilized to said solid support via a linker.

* * * * *